US011338030B2

(12) United States Patent
Volkmann et al.

(10) Patent No.: US 11,338,030 B2

(45) Date of Patent: May 24, 2022

(54) MULTIVALENT RECOMBINANT MODIFIED VACCINIA VIRUS ANKARA (MVA) VECTOR ENCODING FILOVIRUS IMMUNOGENS

(71) Applicant: Bavarian Nordic A/S, Kvistgaard (DK)

(72) Inventors: Ariane Volkmann, Andechs (DE); Robin Steigerwald, Munich (DE); Hubertus Hochrein, Munich (DE); Ulrike Dirmeier, Starnberg (DE); Henning Lauterbach, Eching (DE); Jürgen Hausmann, Gundelfingen (DE)

(73) Assignee: Bavarian Nordic A/S, Hellerup (DK)

( * ) Notice: Subject to any disclaimer, the term of this patent is extended or adjusted under 35 U.S.C. 154(b) by 42 days.

(21) Appl. No.: 16/802,805

(22) Filed: Feb. 27, 2020

(65) Prior Publication Data

US 2020/0268872 A1 Aug. 27, 2020

Related U.S. Application Data

(62) Division of application No. 15/508,851, filed as application No. PCT/EP2015/070161 on Sep. 3, 2015, now Pat. No. 10,576,141.

(Continued)

(51) Int. Cl.

*A61K 39/12* (2006.01)

*C12N 7/00* (2006.01)

(Continued)

(52) U.S. Cl.

CPC ................ *A61K 39/12* (2013.01); *C12N 7/00* (2013.01); *A61K 2039/545* (2013.01); (Continued)

(58) Field of Classification Search

CPC .......... A61K 39/12; C12N 2710/24141; C12N 2760/14134; C12N 7/00; C12N 2710/24143; C12N 2760/14234

See application file for complete search history.

(56) References Cited

U.S. PATENT DOCUMENTS 9,097,713 B2 * 8/2015 Dye ........................ A61P 37/04

10,072,274 B2 * 9/2018 Steigerwald ....... C12N 15/8613

(Continued)

FOREIGN PATENT DOCUMENTS

WO 2010057650 A1 5/2010

WO 2013155441 A1 10/2013

(Continued)

OTHER PUBLICATIONS

Swenson, D. L., et al., 2005, Virus-like particles exhibit potential as a pan-filovirus vaccine for both Ebola and Marburg viral infections, Vaccine 23:3033-3042.*

(Continued)

*Primary Examiner* — Jeffrey S Parkin

(57) ABSTRACT

The present invention relates to an improved filovirus vaccine comprising a recombinant modified vaccinia virus Ankara-based (MVA-based) vaccine against filovirus infection and to related products, methods and uses. Specifically, the present invention relates to genetically engineered (recombinant) MVA and FPV vectors comprising at least one heterologous nucleotide sequence encoding an antigenic determinant of a Marburg virus (MARV) or Ebola virus glycoprotein. Specifically, the invention relates to recombinant MVA comprising Ebola virus glycoprotein and virion protein 40. The invention also relates to products, methods and uses thereof as well as prime/boost regimens of MVA and genetically engineered (recombinant) FPV, e.g., suitable to induce a protective immune response in a subject.

12 Claims, 24 Drawing Sheets

Specification includes a Sequence Listing.

Related U.S. Application Data

(60) Provisional application No. 62/055,154, filed on Sep. 25, 2014, provisional application No. 62/045,538, filed on Sep. 3, 2014.

(51) Int. Cl.
*C07K 14/08* (2006.01)
*A61K 39/00* (2006.01)

(52) U.S. Cl.
CPC .... *C07K 14/08* (2013.01); *C12N 2710/24143* (2013.01); *C12N 2760/14134* (2013.01); *C12N 2760/14234* (2013.01)

(56) References Cited

U.S. PATENT DOCUMENTS

| | | | | |
|---|---|---|---|---|
| 10,428,314 | B2 * | 10/2019 | Towner | C12Q 1/701 |
| 2013/0101618 | A1 | 4/2013 | Sullivan et al. | |
| 2015/0361141 | A1 | 12/2015 | Buttigieg et al. | |

FOREIGN PATENT DOCUMENTS

| | | | |
|---|---|---|---|
| WO | 2014037124 | A1 | 3/2014 |
| WO | WO 2014/037124 | A1 * | 3/2014 |

OTHER PUBLICATIONS

Callendret et al., "A prophylactic multivalent vaccine against different filovirus species is immunogenic . . . ," PLOS One, 2018, pp. 1-24, vol. 13, e0192312.

Barouch et al., "Vaccine protection against acquisition of neutralization-resistant SIV challenges in rhesus monkeys," Nature, 2012, pp. 89-94, vol. 482.

Bradfute et al., "Filovirus vaccines," Human Vaccines, 2011, pp. 701-711, vol. 7.

Enterlein et al., "Rescue of recombinant Marburg virus from cDNA is dependent on nucleocapsid protein VP30," J. Virol., 2006, pp. 1038-1043, vol. 80.

Falzarano et al., "Progress in filovirus vaccine development . . . " Exp. Rev. Vaccines, 2011, pp. 63-77, vol. 10.

Geisbert et al., "Evaluation in Nonhuman Primates of Vaccines against Ebola virus," Emerging Infectious Disease, 2002, pp. 503-507, vol. 8.

Geisbert et al., "Recombinant adenovirus serotype 26 (Ad26) and Ad35 vaccine vectors bypass immunity to Ad5 and protect nonhuman primates against ebolavirus challenge," J. Virol., 2011, pp. 4222-4223, vol. 85.

Gilbert et al., "Enhanced CD8 T cell immunogenicity . . . in a mouse malaria model . . . " Vaccine, 2002, pp. 1039-1045, vol. 20.

Hodge et al., "Harnessing the unique local immunostimulatory properties of modified vaccinia Ankara (MVA) virus to generate superior tumor-specific immune responses . . . ," Vaccine, 2009, pp. 4475-4482, vol. 27.

Hoenen et al., "Ebola virus: unravelling pathogenesis to combat a deadly disease," Trends in Mol. Med., 2006, pp. 206-215, vol. 12.

Hutchings et al., "Combination of protein and viral vaccines induces potent cellular and humoral immune responses . . . ," Infection and Immunity, 2007, pp. 5819-5826, vol. 75.

Keefer et al., "A phase I trial of preventive HIV vaccination with heterologous poxviral-vectors containing matching HIV-1 inserts in healthy HIV-uninfected subjects," Vaccine, 2011, pp. 1948-1958, vol. 29.

Lauterbach et al., "Genetic adjuvantation of recombinant MVA with CD40L potentiates CD8 T cell mediated immunity," Frontiers in Immunology, 2013, pp. 1-16, vol. 4.

Mohamadzadeh et al., "How Ebola and Marburg viruses battle the immune system," Nature Rev. Immunol., 2007, pp. 556-567, vol. 7.

Nakayama and Saijo, "Animals models for Ebola and Marburg virus infections," Frontiers in Microbiol., 2013, pp. 1-20, vol. 4, Art. 267.

Ning et al., "The roles of ebolavirus glycoproteins in viral pethogenesis," Virologica Sinica, 2017, pp. 3-15, vol. 32.

Rimmelzwaan and Sutter, "Candidate influenza vaccines based on recombinant modified vaccinia virus Ankara," Expert Rev. Vaccines, 2009, pp. 447-454, vol. 8.

Roshorm et al., "T cells induced by recombinant chimpanzee adenovirus alone and in prime-boost regimens decrease chimeric EcoHIV/NDK challenge virus load," Eur. J. Immunol., 2012, pp. 3243-3255, vol. 42.

Sanchez et al., "Analysis of Human Peripheral Blood Samples . . . ," J. Virol., 2004, pp. 10370-77, vol. 78.

Soprana et al., "Joint production of prime/boost pairs of Fowlpox Virus and [MVA] recombinants carrying the same transgene," J. Virol. Meth., 2011, pp. 22-28, vol. 174.

Subbotina et al., "Genetic factors of Ebola virus virulence in guinea pigs," Virus Res., 2010, pp. 121-133, vol. 153.

Towner et al., "Marburgvirus genomics and association with a large hemorrhagic fever outbreak in Angola," J. Virol., 2006, pp. 6497-6516, vol. 80.

Wang et al., "De novo syntheses of Marburg virus antigens from adenovirus vectors induce potent humoral and cellular immune responses," Vaccine, 2006, pp. 2975-2986, vol. 24.

Warfield and Aman, "Advances in virus-like particle vaccines for filoviruses," J. Inf. Dis., 2011, pp. S1053-S1059, Suppl. 3.

Written Opinion and Search Report of the ISA for PCT/US2015/048357 dated Jan. 11, 2016.

Written Opinion and Search Report of the ISA for PCT/US2015/148388 dated Jan. 11, 2016.

Written Opinion and Search Report of the ISA for PCT/EP2015/070161 dated Apr. 19, 2016.

* cited by examiner

Figure 2

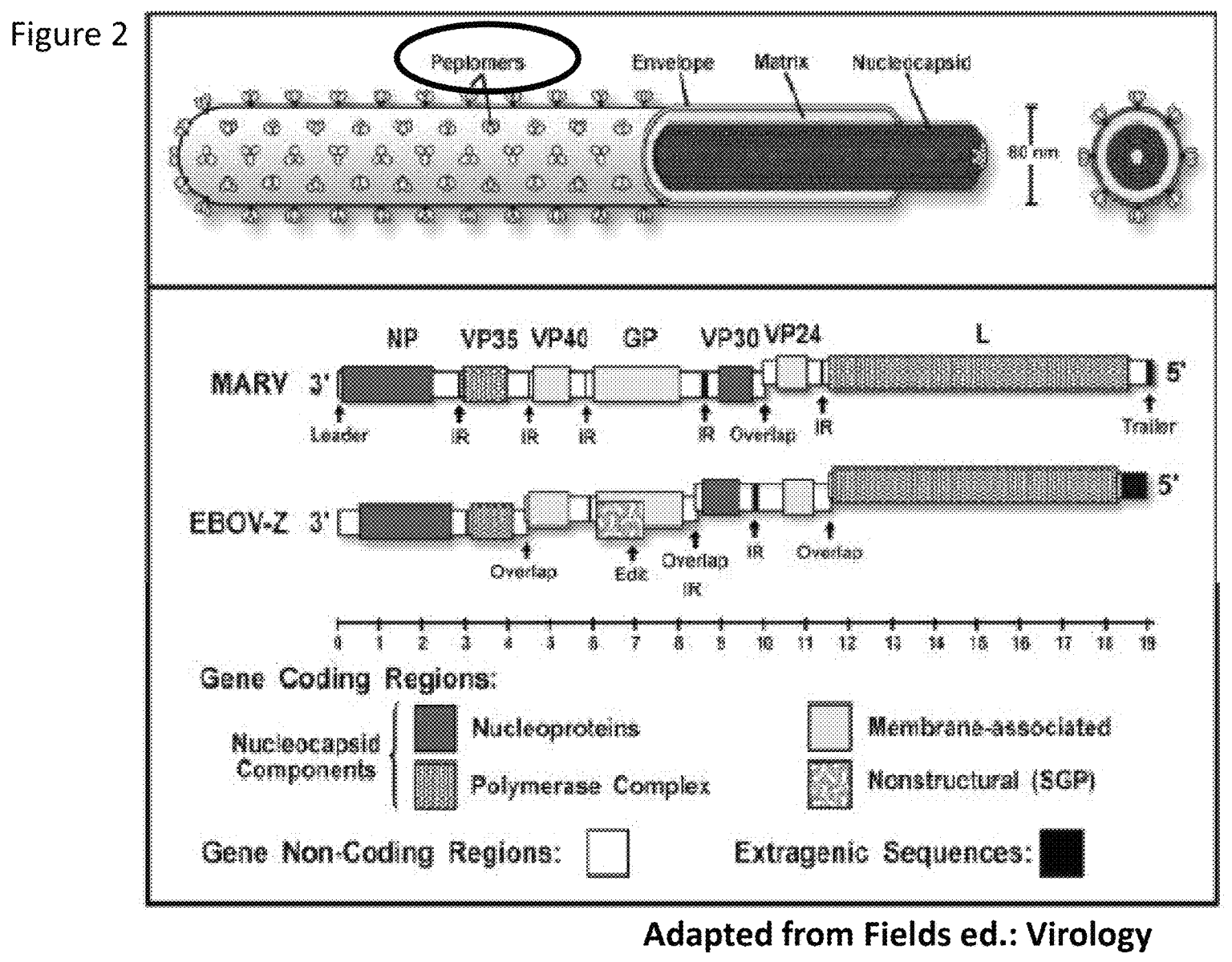

Peplomers
Envelope
Matrix
Nucleocapsid
80 nm

MARV 3' NP VP35 VP40 GP VP30 VP24 L 5'
Leader IR IR IR IR Overlap IR Trailer
EBOV-Z 3' 5'
Overlap Edit Overlap IR IR Overlap Gene Coding Regions:
Nucleocapsid Components
Nucleoproteins
Polymerase Complex
Membrane-associated
Nonstructural (SGP)
Gene Non-Coding Regions:
Extragenic Sequences:

Adapted from Fields ed.: Virology

ITR
IGR 148/149
148R
149L
GP-MARV-Musoke
PrS
MVA-mBN252B
ITR insert
1
IGR 88/89
88R
89L
2
IGR 148/149
148R
149L
ITR
GP-SEBOV
NP-CdI-EBOV
GP-ZEBOV
GP-MARV-Musoke
PrS
PrLE1
Pr7.5
PrS
MVA-mBN226B
ITR

Figure 3C

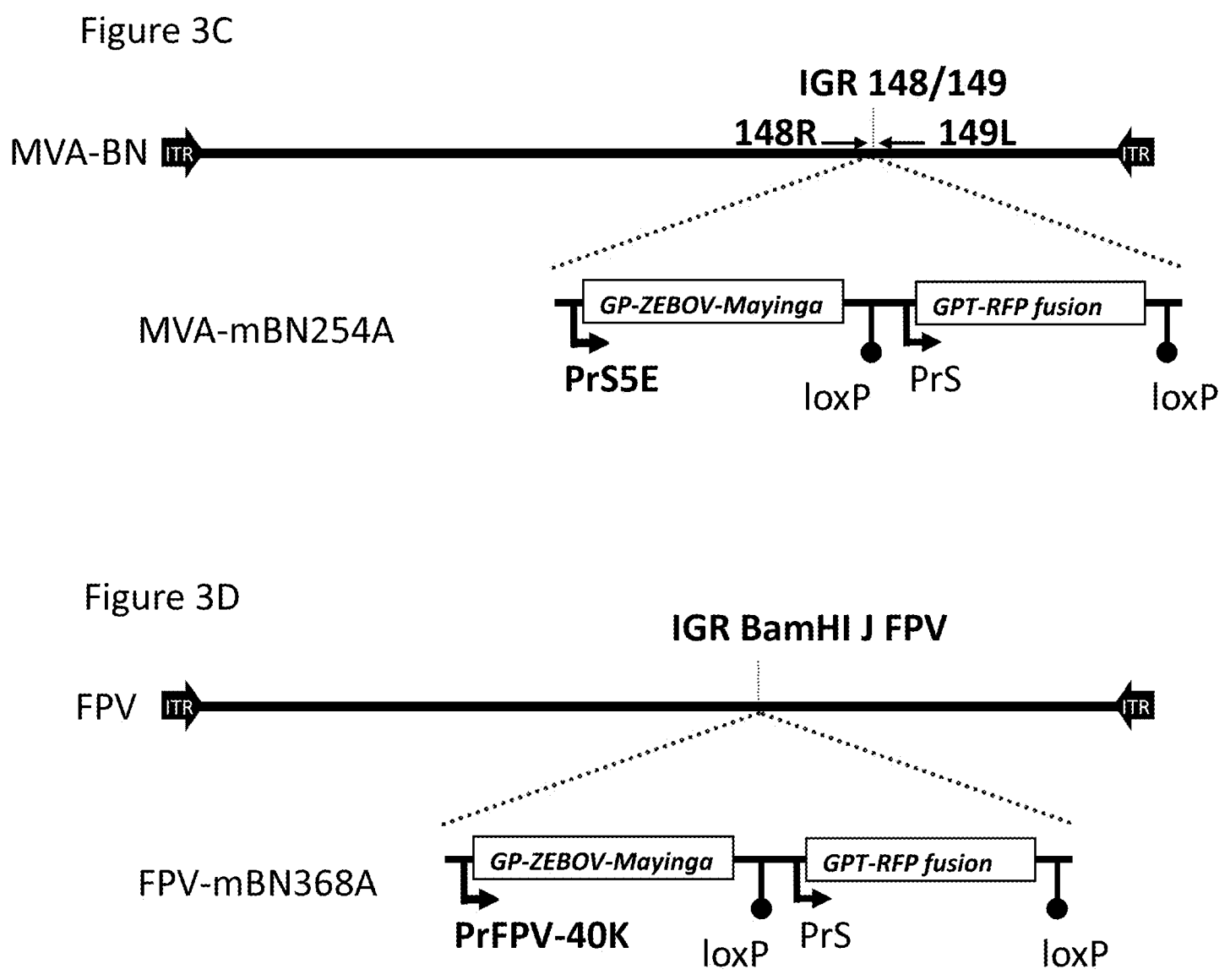

MVA-BN

ITR

IGR 148/149

148R

149L

ITR

MVA-mBN254A

PrS5E

GP-ZEBOV-Mayinga loxP

PrS

GPT-RFP fusion loxP

Figure 3D

FPV

ITR

IGR BamHI J FPV

ITR

FPV-mBN368A

PrFPV-40K

GP-ZEBOV-Mayinga loxP

PrS

GPT-RFP fusion loxP

F1 IGR 148-149
PrS
GP-MARV-Mu
pBN433
7602bp
Amp
loxP
transcription stop
PrS
GPT
RFP
loxP
F2 IGR 148-149

Figure 5A

Figure 5C:
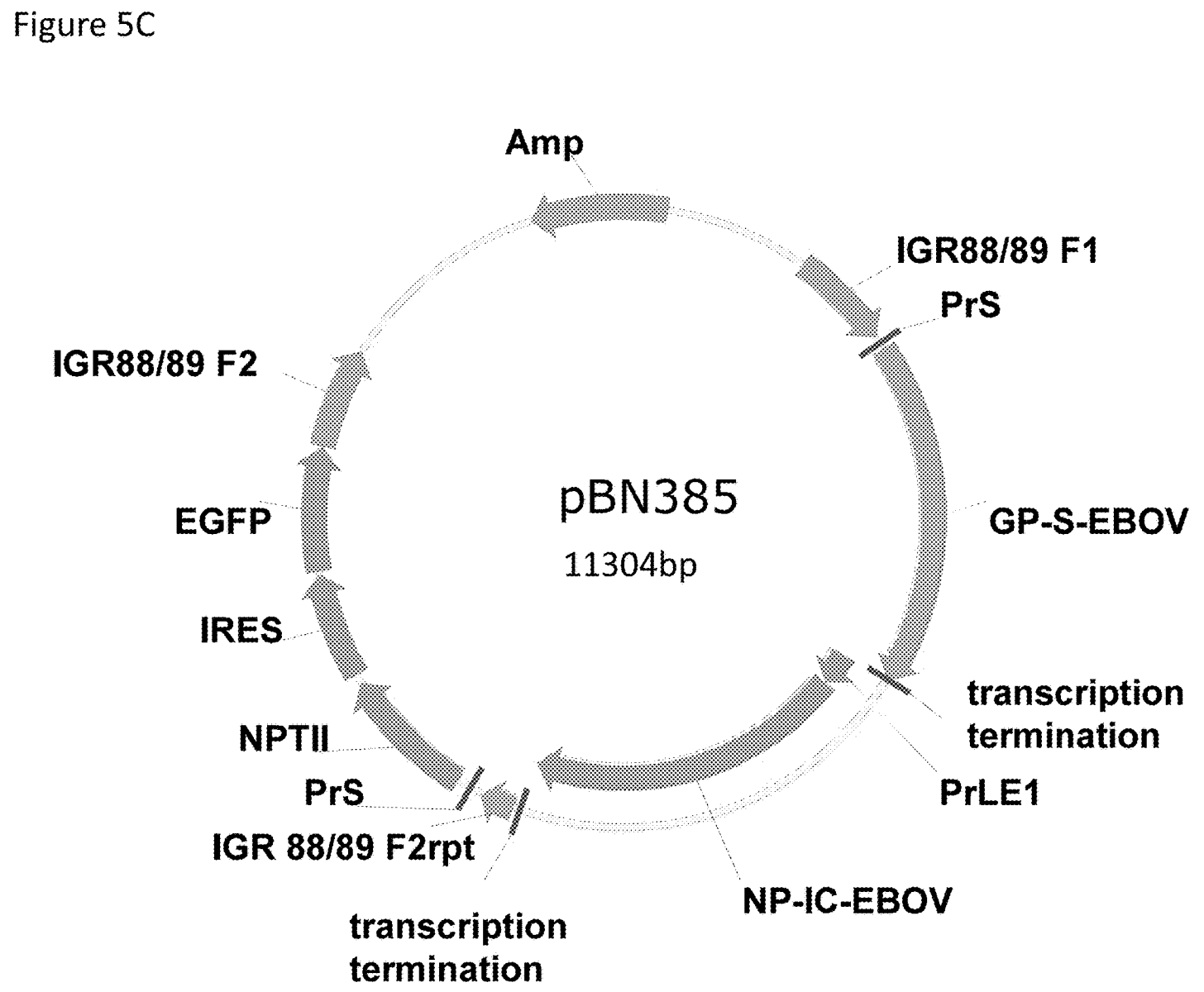

Figure 5C pBN385
11304bp

IGR88/89 F1
PrS
GP-S-EBOV
transcription termination
PrLE1
NP-IC-EBOV
transcription termination
IGR 88/89 F2rpt
PrS
NPTII
IRES
EGFP
IGR88/89 F2
Amp OD450
Anti-MARV-GP
4
3
2
1
0
10¹
10²
10³
10⁴
10⁵
10⁶ titer
a
b
c
d
OD450
Anti-Zaire-GP
4
3
2
1
0
10¹
10²
10³
10⁴
10⁵
10⁶ titer
a
b
c
d
OD450
Anti-Sudan-GP
2.0
1.5
1.0
0.5
0.0
10¹
10²
10³
10⁴
10⁵
10⁶ titer
a
b
c
d
A Pre-vaccination
B Post first vaccination
C Post booster vaccination
D Hyperimmune NHP positive control serum

Figure 7A

Survival [%]

100
80
60
40
20
0

0 5 10 15 20

Time Post MARV Challenge (Day)

TBS (control)
MVA-BN®-Filo

Figure 7B

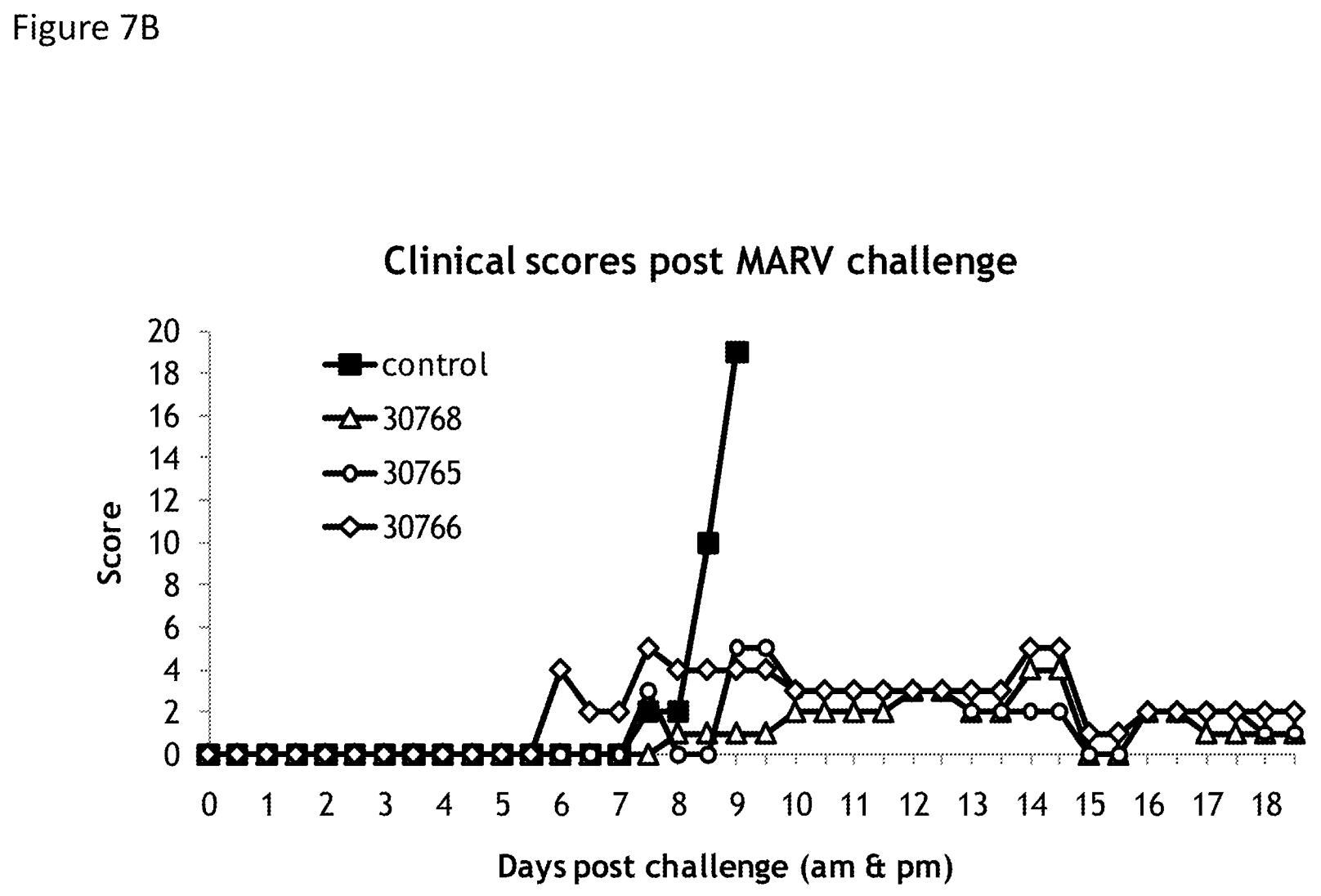

Clinical scores post MARV challenge control
30768
30765
30766

Score 20
18
16
14
12
10
8
6
4
2
0

0 1 2 3 4 5 6 7 8 9 10 11 12 13 14 15 16 17 18

Days post challenge (am & pm)

Figure 8A:
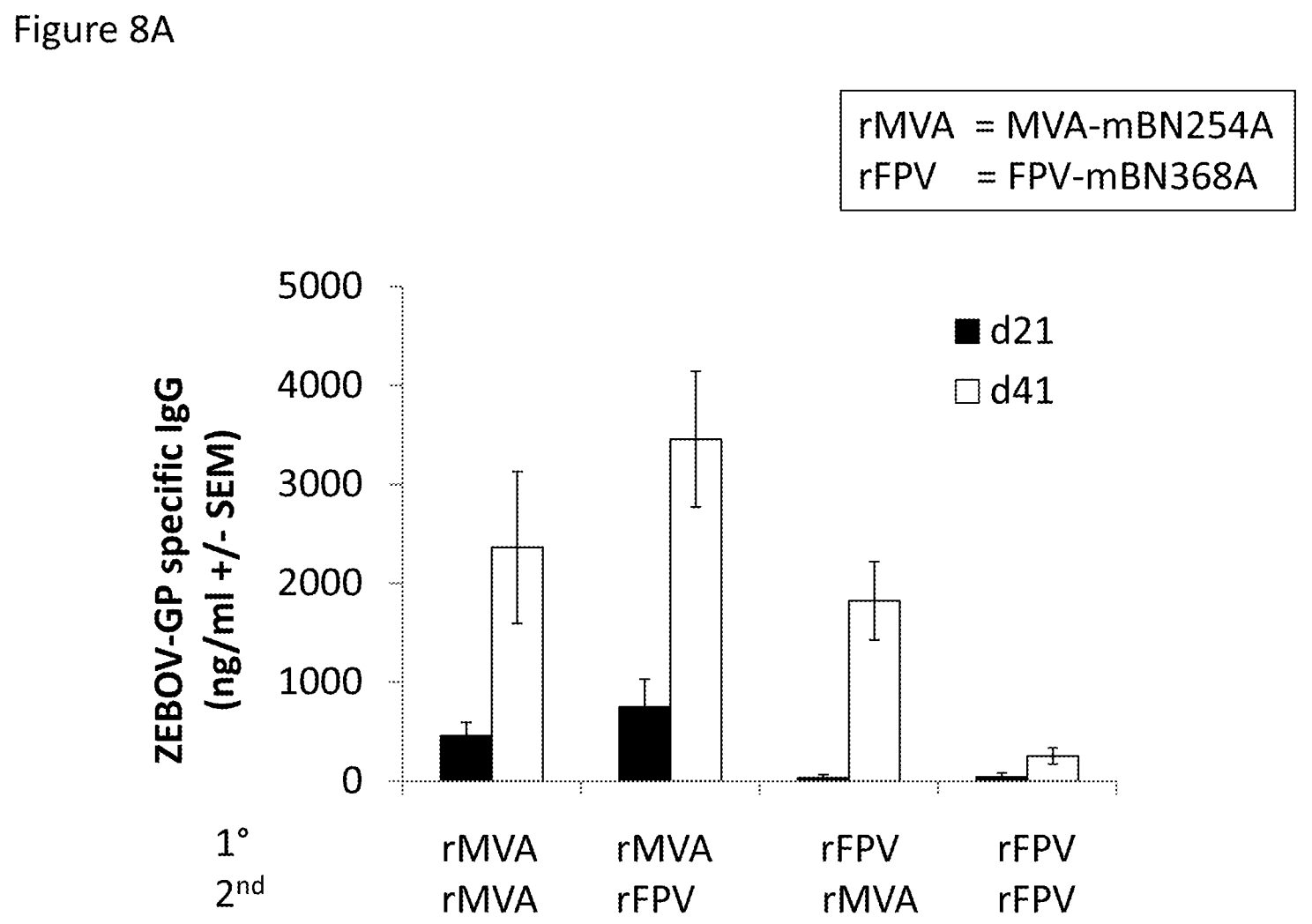

rMVA = MVA-mBN254A
rFPV = FPV-mBN368A

■ d21
□ d41

ZEBOV-GP specific IgG (ng/ml +/- SEM)

5000
4000
3000
2000
1000
0

1° rMVA rMVA rFPV rFPV
2nd rMVA rFPV rMVA rFPV

Figure 8A rMVA = MVA-mBN254A
rFPV = FPV-mBN368A
CD107a+ (cells/spleen × 10^4)
IFN-γ+ (cells/spleen × 10^4)
TNF-α+ (cells/spleen × 10^4)
30
25
20
15
10
5
0
1st
2nd
rMVA rMVA
rMVA rFPV
rFPV rMVA
rFPV rFPV CD107a+
TNF-α+
IFN-γ+
50
40
30
20
10
0
1
2
3

Figure 10

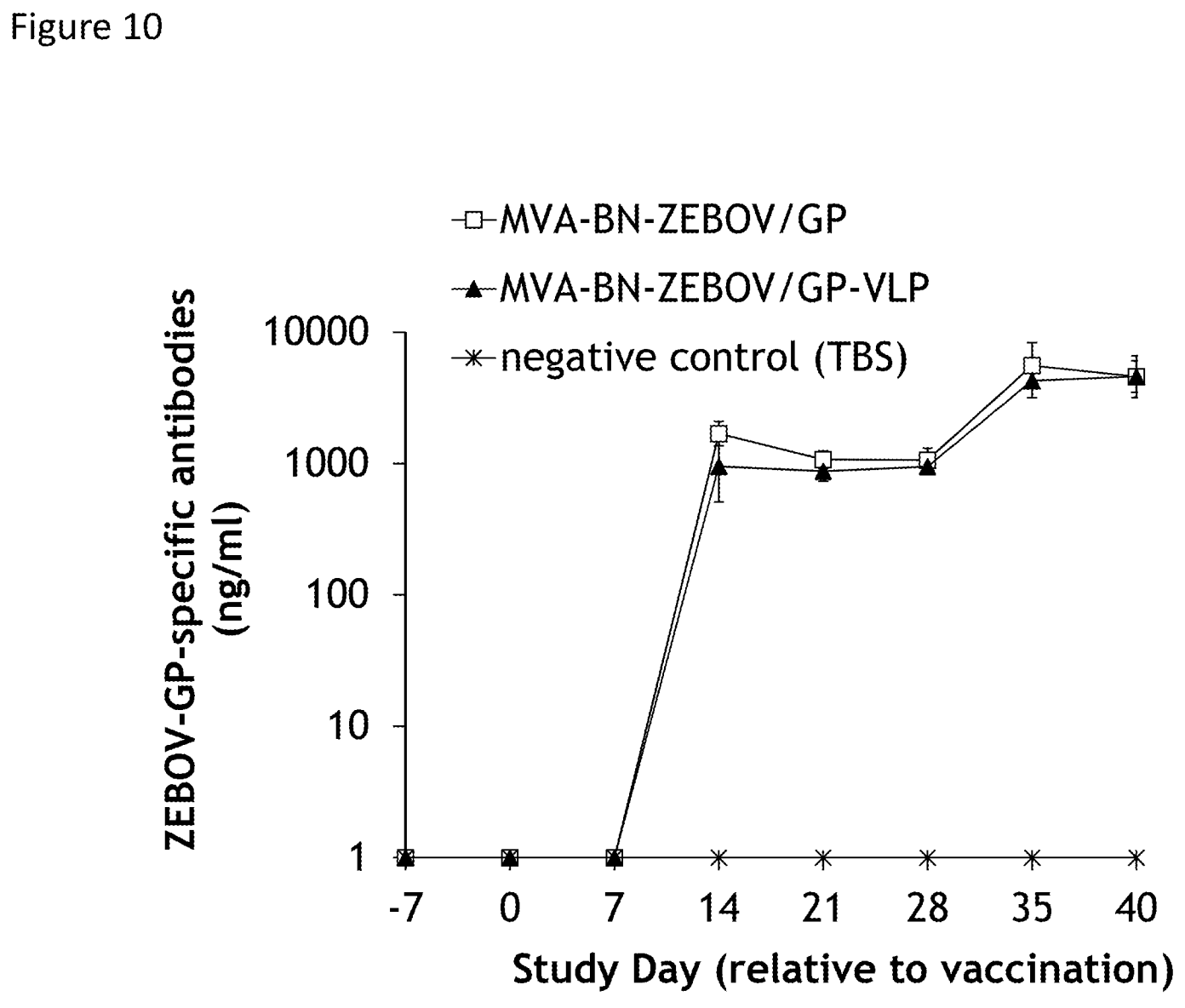

MVA-BN-ZEBOV/GP
MVA-BN-ZEBOV/GP-VLP
negative control (TBS)

ZEBOV-GP-specific antibodies (ng/ml)

10000
1000
100
10
1

-7
0
7
14
21
28
35
40

Study Day (relative to vaccination)

Figure 11

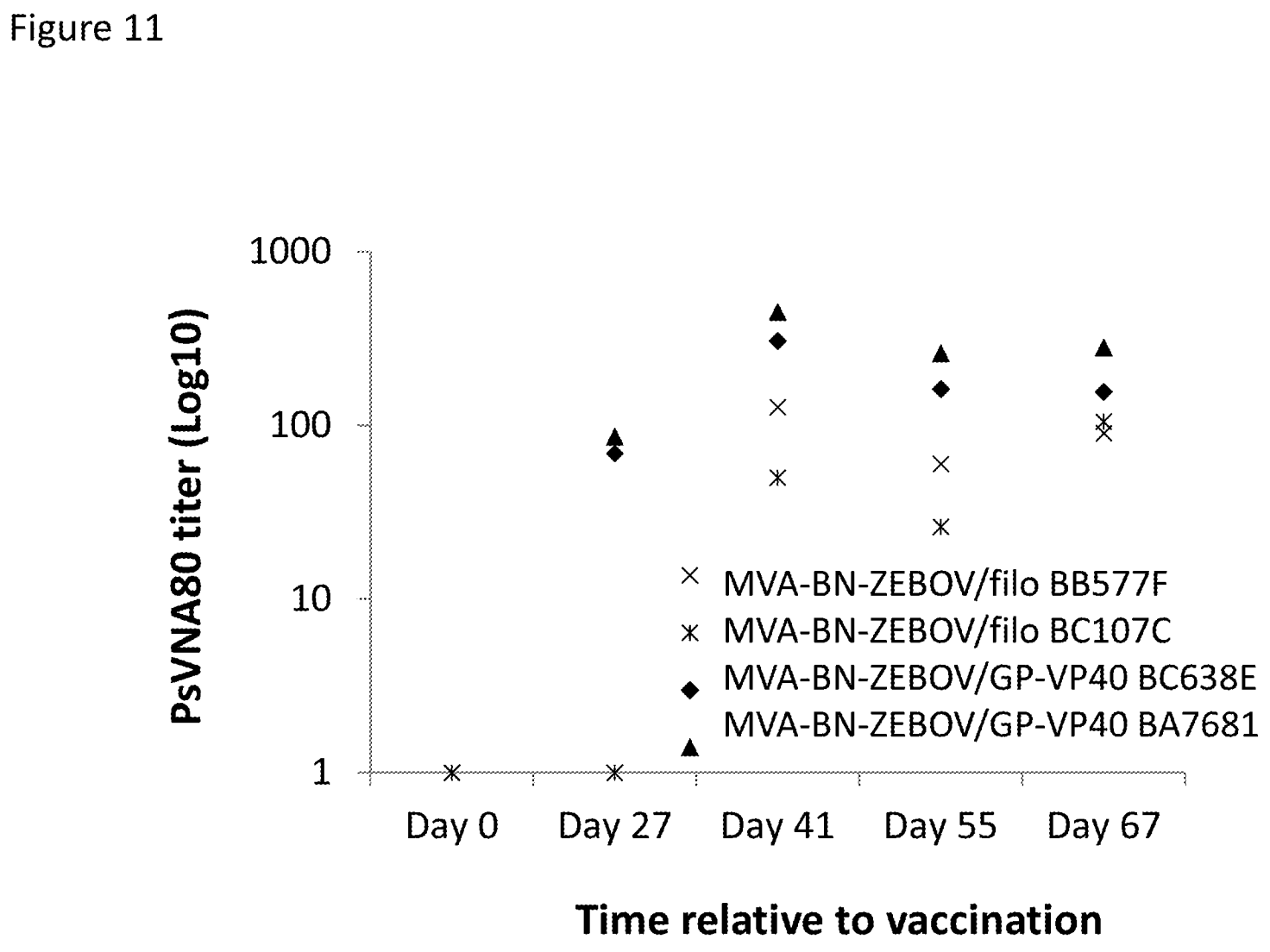

PsVNA80 titer (Log10)

1000
100
10
1

Day 0
Day 27
Day 41
Day 55
Day 67

Time relative to vaccination

MVA-BN-ZEBOV/filo BB577F
MVA-BN-ZEBOV/filo BC107C
MVA-BN-ZEBOV/GP-VP40 BC638E
MVA-BN-ZEBOV/GP-VP40 BA7681

A
B
C
lysate
UC-SN
166 254 255
166 254 255
GP
VP40
D
IP α-GP
- - + + 1 % TX-100
254 255 254 255
GP
VP40
α-GP ZEBOV
α-VP40 ZEBOV

MULTIVALENT RECOMBINANT MODIFIED VACCINIA VIRUS ANKARA (MVA) VECTOR ENCODING FILOVIRUS IMMUNOGENS

FIELD OF THE INVENTION

The present invention relates to an improved filovirus vaccine comprising a recombinant modified vaccinia virus Ankara-based (MVA-based) vaccine against filovirus disease and to related products, methods and uses. Specifically, the present invention relates to genetically engineered (recombinant) MVA vectors comprising a heterologous nucleotide sequence encoding an antigenic determinant of a filovirus protein. The present invention also relates to vaccination methods, in particular homologous and heterologous prime-boost vaccination regimes employing two viral vector compositions. More particularly, the invention relates to a recombinant MVA for use in a homologous prime-boost vaccination regime and/or a recombinant MVA and a recombinant fowlpox virus (FPV) for use in a heterologous prime-boost vaccination regime. The invention also relates to products, methods and uses thereof, e.g., suitable to induce a protective immune response in a subject.

BACKGROUND OF THE INVENTION

Filoviruses are enveloped, non-segmented, negative-strand RNA viruses of the virus family Filoviridae. Two members of this virus family have been identified to date: Marburg virus (MARV) and Ebola virus (EBOV). Filoviruses are extremely virulent, easily transmissible from person-to-person, and extraordinarily lethal, causing severe hemorrhagic fever in humans and non-human primates. Filovirus infections have a fatality rate in humans ranging from 23% to as high as 90%. Despite their transmissibility and lethality, however, no approved therapy or preventive vaccine is available.

During outbreaks, isolation of patients and use of protective clothing and disinfection procedures (together called viral hemorrhagic fever (VHF) isolation precautions or barrier nursing) has been sufficient to interrupt further transmission of Marburg or Ebola viruses, and thus to control and end the outbreak. Because there is no known effective treatment for the hemorrhagic fevers caused by filoviruses, transmission prevention through application of VHF isolation precautions is currently the only available means to control filovirus outbreaks.

The first filovirus was recognized in 1967 after a number of laboratory workers in Germany and Yugoslavia, who had been handling tissues from African green monkeys, developed severe hemorrhagic fever. A total of 31 cases and seven deaths were associated with these outbreaks. The virus was named Marburg virus (MARV) after Marburg, Germany, the site of one of the outbreaks. After the initial outbreaks the virus disappeared and did not reemerge until 1975, when a traveler, most likely exposed in Zimbabwe, became ill in Johannesburg, South Africa; the traveler's traveling companion and a nurse were also infected. A few sporadic cases of Marburg hemorrhagic fever (MHF) have been identified since that time, but the disease remains relatively rare.

The second filovirus, Ebola virus (EBOV), was first identified in 1976 when two outbreaks of Ebola hemorrhagic fever (EHF) occurred in northern Zaire (now the Democratic Republic of Congo) and southern Sudan. The outbreaks involved viruses which eventually proved to be two different species of Ebola virus, which were named after the nations in which they were discovered. Both viruses proved to be highly lethal, with 90% of the cases in Zaire and 50% of the cases in Sudan resulting in death. Since 1976, Ebola virus has appeared sporadically in Africa, with a few small-to medium-sized outbreaks confirmed between 1976 and 1979, and again in Gabon between 1994 and 1996. Larger epidemics of Ebola HF occurred in Kikwit, Zaire in 1995 and in Gulu, Uganda in 2000.

It appears that filoviruses are transmitted to humans from ongoing life cycles in one or more non-human animals. Despite numerous attempts to locate the natural reservoir or reservoirs of Ebola and Marburg viruses, however, their origins remain mysterious. Consequently, it also remains unclear just how the virus is transmitted from its natural reservoir(s) to humans. Once a human has been infected, however, further infections occur by person-to-person transmission. Specifically, transmission involves close personal contact between an infected individual or their body fluids and another person. During recorded outbreaks of hemorrhagic fever caused by filovirus infection, people who cared for (i.e., fed, washed, medicated) or worked very closely with infected individuals were especially at risk of becoming infected themselves. Nosocomial (hospital) transmission through contact with infected body fluids (i.e., via reuse of unsterilized syringes, needles, or other medical equipment contaminated with these fluids) has also been an important factor in the spread of disease. Minimizing close contact between uninfected and infected patients usually reduces the number of new filovirus infections in humans during an outbreak. Although filoviruses have displayed some capability of infection through small-particle aerosols in the laboratory, airborne spread among humans has not been clearly demonstrated.

Five strains of Ebola virus have been identified so far, and are named after their site of first appearance: Bundibugyo (BEBOV), Ivory Coast (EBOV-Cdl, also called Tai Forest virus or TAFV), Reston (EBOV-Reston), Sudan (SEBOV), and Zaire (ZEBOV); the Zaire, Sudan, and Bundibugyo strains are commonly involved in morbidity and death in humans. Ebola-Reston is the only known filovirus that does not cause severe disease in humans, although it can be fatal in monkeys. Several strains of Marburg virus have been identified so far, with the Musoke strain having the highest lethality rate. See FIG. 1.

Structurally, filovirus virions may appear in several shapes, including long, sometimes branched filaments, as well as shorter filaments shaped like a "6", the letter "U", or a circle. Viral filaments can measure up to 14 micrometers (μm) in length, have a uniform diameter of 80 nanometers (nm), and are enveloped in a lipid membrane. Each virion contains one single-stranded, negative-sense RNA molecule approximately 19 kilobase pairs (kb) in length, which contains seven sequentially arranged genes in the order of nucleoprotein (NP), virion protein 35 (VP35), virion protein 40 (VP40), envelope glycoprotein (GP), virion protein 30 (VP30), virion protein 24 (VP24), and RNA-directed RNA polymerase protein (L). Upon entry into the host cell cytoplasm, the RNA is transcribed to generate polyadenylated, subgenomic mRNA species encoding the proteins. Transcription and translation lead to the synthesis of seven structural polypeptides, with presumed identical functions for each of the different filoviruses. Four proteins (NP, VP30, VP35 and L) are associated with the viral genomic RNA in the nucleocapsid complex. The three remaining structural proteins are membrane-associated; GP is a type I transmembrane protein, while VP24 and VP40 are probably located on the inner side of the membrane. The envelope glycoprotein (GP) appears in the viral envelope as a homotrimer (also referred to as a 'peplomer') comprising three copies of a heterodimer. The heterodimer contains two fragments of the full-length GP precursor (referred to as 'GP0') known as 'GP1' and 'GP2' produced by furin cleavage. GP1 and GP2 are linked by a disulfide bond. A non-structural, secreted glycoprotein (sGP) is expressed by EBOV, but not MARV (H. Feldmann & M. P. Kiley, Curr. Top. Microbiol. Immunol. 235:1-21 (1999)). New viral particles are created by budding from the surface of host cells (see below).

The filovirus life cycle begins with virion attachment to specific cell-surface receptors, followed by fusion of the virion envelope with cellular membranes and release of the virus nucleocapsid into the cytosol. The viral RNA-directed RNA polymerase (RNAP, also known as the 'L' protein) partially uncoats the nucleocapsid and transcribes the genes into positive-stranded mRNAs, which are then translated into structural and nonstructural proteins. See FIG. 2. The RNAP binds to a single promoter located at the 3' end of the genome. Transcription either terminates after a gene or continues to the next gene downstream, meaning that genes close to the 3' end of the genome are transcribed in the greatest abundance, while those towards the 5' end of the genome are least likely to be transcribed. Gene order is therefore a simple but effective form of transcriptional regulation. The most abundant protein produced is the nucleoprotein (NP), cellular concentration of which determines when the RNAP switches from gene transcription to genome replication. Replication results in full-length, positive-stranded anti-genomes that are in turn transcribed into negative-stranded virus progeny genome copies. Newly synthesized structural proteins and genomes self-assemble and accumulate near the inside of the cell membrane. Virus particles are enveloped as they bud from the infected host cell, producing mature infectious virions.

Prior Vaccine Development

Many strategies have been evaluated during attempts to develop a safe, immunogenic vaccine capable of inducing protective immunity against infection by one or more filovirus species, with decidedly mixed results. An overview is summarized in Marzi and Feldmann (A. Marzi and H. Feldmann *Expert Rev. Vaccines* 13(4):521-531 (2014)). For instance, while a trivalent DNA vaccine comprising a mixture of three DNA plasmids, one expressing the envelope glycoprotein from ZEBOV, a second expressing the envelope glycoprotein from SEBOV, and a third expressing the nucleoprotein from ZEBOV was safe, immunogenic, and able to induce an antibody response against at least one of the three antigens in humans. CD8+ T-cell responses were detected in fewer than ⅓ of the vaccinated population (J. E. Martin et al., *Clin. Vaccine Immunol.* 13(11):1267-1277 (2006)). Similarly, a complex, pentavalent adenovirus-based 'pan-filovirus' vaccine comprising a mixture of four different recombinant adenoviruses expressing envelope glycoproteins from ZEBOV, SEBOV, Marburg-Ci67 (strain Ratayczak), Marburg-Musoke, and Marburg-Ravn, as well as nucleoproteins from ZEBOV and Marburg-Musoke, protected non-human primates from ZEBOV or MARV challenge and induced antibody responses to both types of virus, although it remains unclear whether the vaccine induced any CD8+ T-cell response (D. L. Swenson et al., *Clin. Vaccine Immunol.* 15(3):460-467 (2008)).

Intranasal administration of a recombinant paramyxovirus—human parainfluenza virus, serotype 3 (HPIV3)—expressing either the envelope glycoprotein or both the envelope glycoprotein and nucleoprotein from ZEBOV protected guinea pigs from subsequent challenge with EBOV. Rodent models are frequently poorly predictive of results in primates, with a number of previous EBOV vaccine candidates that were effective in rodents failing completely in non-human primates (A. Bukreyev et al., *J. Virol.* 80(5):2267-2279 (2006)). Intranasal administration of a recombinant HPIV3 expressing either the envelope glycoprotein or both the envelope glycoprotein and nucleoprotein from ZEBOV in rhesus monkeys showed that any construct expressing the envelope glycoprotein was moderately immunogenic and protected more than 80% of the animals against disease after post-vaccination challenge with ZEBOV (A. Bukreyev et al., *J. Virol.* 81(12):6379-6388 (2007)). Finally, a recombinant vesicular stomatitis virus (VSV) in which the VSV glycoprotein was replaced by the ZEBOV envelope glycoprotein protected 50% of guinea pigs, 100% of mice following treatment as late as 24 hours after an otherwise uniformly lethal infection. Four out of eight rhesus macaques (50%) were protected when treated 20 to 30 min after exposure providing a post-exposure treatment option for Ebola virus infection (H. Feldmann, *PLoS Pathogens* 3(1):54-61 (2007)).

Geisbert et al. evaluated the effects of vaccine strategies that had protected mice or guinea pigs from lethal EBOV infection in nonhuman primates. They used RNA replicon particles derived from an attenuated strain of Venezuelan equine virus (VEEV) expressing EBOV glycoprotein and nucleoprotein, recombinant Vaccinia virus (VACV) expressing EBOV glycoprotein, liposomes containing lipid A and inactivated EBOV, and a concentrated, inactivated whole-virion preparation. They found that none of these strategies successfully protected nonhuman primates from robust challenge with EBOV (T. H Geisbert et al., *Emerging Infectious Diseases* 8(3):503-507 (2002)).

Others have used Virus Like Particles (VLPs) expressed in mammalian, bacterial, plant or insect cells as non-replicating subunit vaccines (D. L. Swenson et al., *Vaccine* 23:3033-3042 (2005); K. L. Warfield et al., *JID* 196(2):430-437 (2007), N. Kushnir et al., *Vaccine* 31(1):58-83 (2012), K. L. Warfield ET AL., *PLOS ONE* 10(3):e0118881 (2015), K. L. Warfield and M. J. Aman *JID* 204:1053-1059 (2011), V. M. Wahl-Jensen et al., *J Virol.* 79(16):10442-10450 (2005), WO 2003/039477, WO 2006/046963, WO 2006/073422, WO 2004/042001, U.S. Pat. Nos. 8,900,595, 7,211,378) to induce antibody responses. However, filovirus VLPs require a cost-intensive and challenging production process and need to be stored at ambient temperature over time.

Thus, after expending considerable time and effort, a few promising vaccine candidates have emerged at preclinical stages, but at present no approved preventive vaccine is available. Given the transmissibility and lethality of filovirus infection, there is a pressing need for an effective vaccine.

BRIEF SUMMARY OF THE INVENTION

It is discovered in the present invention that various prime-boost combinations of replication deficient and replication incompetent vectors generate effective immune protection against filovirus infection.

Accordingly, one general aspect of the present invention relates to a combination vaccine comprising:

a) a first composition comprising an immunologically effective amount of a MVA vector comprising a nucleic acid encoding an antigenic protein of at least one filovirus subtype, together with a pharmaceutically acceptable carrier; and b) a second composition comprising an immunologically effective amount of a fowlpox vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the present invention relates to a combination vaccine comprising:

(a) a first composition comprising an immunologically effective amount of a MVA vector comprising a nucleic acid encoding an antigenic protein of at least two filovirus subtypes, together with a pharmaceutically acceptable carrier; and (b) a second composition comprising an immunologically effective amount of a MVA vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the present invention relates to a kit comprising:

(a) a first composition comprising an immunologically effective amount of a MVA vector comprising a nucleic acid encoding an antigenic protein of at least one filovirus subtypes, together with a pharmaceutically acceptable carrier; and (b) a second composition comprising an immunologically effective amount of a fowlpox vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the present invention relates to a kit comprising:

(a) a first composition comprising an immunologically effective amount of a MVA vector comprising a nucleic acid encoding antigenic proteins of at least two filovirus subtypes, together with a pharmaceutically acceptable carrier; and (b) a second composition comprising an immunologically effective amount of a MVA vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the present invention relates to a recombinant Modified Vaccinia Virus (MVA) vector comprising a nucleotide sequence encoding two or more antigenic determinants of a filovirus protein for use in the treatment and/or prevention of a filovirus-caused disease. In yet another aspect, the invention relates to a recombinant MVA vector comprising a nucleotide sequence encoding an antigenic protein of a filovirus glycoprotein and encoding a filovirus virion protein 40 (VP40) for use in the treatment and/or prevention of a filovirus-caused disease. In another embodiment, the invention relates to a recombinant MVA vector comprising a nucleotide sequence selected from the group consisting of a) SEQ ID NO:5, SEQ ID NO:19 and SEQ ID NO:30, b) SEQ ID NO:5, SEQ ID NO:19, SEQ ID NO:28 and SEQ ID NO:30 and c) SEQ ID NO:19 and SEQ ID NO:33. In a certain aspect, the invention relates to a composition comprising said recombinant MVA vector, a vaccine comprising said recombinant MVA vector, a pharmaceutical comprising said recombinant MVA vector and a pharmaceutical carrier, diluent and/or additive, and a cell comprising said recombinant MVA vector. In a certain aspect, the invention relates to said recombinant MVA vector for use as a medicament or vaccine for treating and/or preventing a filovirus-caused disease in a subject and a method for affecting an immune response in a subject comprising administering to the subject said recombinant MVA vector. In an additional aspect, the present invention relates to a kit comprising said recombinant MVA vector in a first vial or container for a first administration (priming) and in a second vial or container for a second administration (boosting).

The present invention also relates to a recombinant FPV vector comprising a nucleotide sequence encoding at least one antigenic determinant of a filovirus protein (e.g. any of the filovirus proteins as mentioned supra or infra, preferably an filovirus envelope glycoprotein) under the control of the FPV-40K promoter having SEQ ID NO:26. In an additional aspect, the invention relates to a recombinant fowlpox virus (FPV) vector comprising a nucleotide sequence encoding one, two or more antigenic determinants of a filovirus protein for use in the treatment and/or prevention of a filovirus-caused disease. In a certain aspect, the invention relates to a composition comprising said recombinant FPV vector, a vaccine comprising said recombinant FPV vector, a pharmaceutical comprising said recombinant FPV vector and a pharmaceutical carrier, diluent and/or additive and a cell comprising said recombinant FPV vector. In a certain aspect, the invention relates to said recombinant FPV vector for use as a medicament or vaccine for treating and/or preventing a filovirus-caused disease in a subject and a method for affecting an immune response in a subject comprising administering to the subject said recombinant FPV vector.

In an additional aspect, the present invention relates to a combination vaccine comprising:

(a) an immunologically effective amount of a MVA vector comprising a nucleic acid encoding antigenic proteins of at least two filovirus subtypes, together with a pharmaceutically acceptable carrier; and (b) an immunologically effective amount of a fowlpox vector comprising a nucleic acid encoding an antigenic protein of a first filovirus subtype, together with a pharmaceutically acceptable carrier;

wherein one of the vectors is a priming vaccine and the other vector is a boosting vaccine.

In an additional aspect, the present invention relates to a combination vaccine comprising:

(a) an immunologically effective amount of a MVA vector comprising a nucleic acid encoding antigenic proteins of at least two filovirus subtypes, together with a pharmaceutically acceptable carrier; and (b) an immunologically effective amount of one or more additional MVA vectors comprising a nucleic acid encoding an antigenic protein of a first filovirus subtype, together with a pharmaceutically acceptable carrier;

wherein one of the MVA vectors is a priming vaccine and the other MVA vectors is a boosting vaccine.

In an additional aspect, the present invention relates to a combination vaccine comprising:

(a) a first composition comprising an immunologically effective amount of a MVA vector comprising a nucleic acid encoding at least one antigenic determinant of a filovirus protein; and (b) a second composition comprising an immunologically effective amount of a MVA vector comprising a nucleic acid encoding at least one antigenic determinant of a filovirus protein;

OR (c) a first composition comprising an immunologically effective amount of a MVA vector comprising a nucleic acid encoding at least one antigenic determinant of a filovirus protein; and (d) a second composition comprising an immunologically effective amount of an FPV vector comprising a nucleic acid encoding at least one antigenic determinant of a filovirus protein;

wherein one of the compositions is a priming composition and the other composition is a boosting composition.

In an additional aspect, the present invention relates to a method of inducing an immune response against a filovirus in a subject, the method comprising administering to the subject:

(a) a first composition comprising an immunologically effective amount of a MVA vector comprising a nucleic acid encoding an antigenic protein of at least one filovirus subtype, together with a pharmaceutically acceptable carrier; and (b) a second composition comprising an immunologically effective amount of a fowlpox vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the present invention relates to a method of inducing an immune response against a filovirus in a subject, the method comprising administering to the subject:

(a) a first composition comprising an immunologically effective amount of a MVA vector comprising a nucleic acid encoding antigenic proteins of at least two filovirus subtypes, together with a pharmaceutically acceptable carrier; and (b) a second composition comprising an immunologically effective amount of a MVA vector comprising a nucleic acid encoding an antigenic protein of a first filovirus subtype, together with a pharmaceutically acceptable carrier;

wherein one of the compositions is a priming composition and the other composition is a boosting composition.

The invention also covers a method of generating a recombinant MVA vector for use in the treatment and/or prevention of a filovirus-caused disease comprising the steps of:

(a) infecting a host cell with a MVA virus, (b) transfecting the infected cell with a recombinant vector comprising at least one nucleotide sequence encoding an antigenic determinant of any of the filovirus proteins of any of the embodiments of the invention, said nucleic acid sequence further comprising a genomic MVA virus sequence capable of directing the integration of the at least one nucleotide sequence into the MVA virus genome, and (c) identifying, isolating and optionally purifying the generated recombinant MVA virus.

In another embodiment, the order of step a) and b) of the method of generating a recombinant MVA vector of any of the above embodiments can be changed such that step b) is the first step and a) the second.

The invention also covers a method of generating a recombinant FPV vector for use in the treatment and/or prevention of a filovirus-caused disease comprising the steps of:

(a) infecting a host cell with an FPV virus, (b) transfecting the infected cell with a recombinant vector comprising at least one nucleotide sequence encoding an antigenic determinant of any of the filovirus proteins of any of the embodiments of the invention, said nucleic acid sequence further comprising a genomic FPV virus sequence capable of directing the integration of the at least one nucleotide sequence into the FPV virus genome, and (c) identifying, isolating and optionally purifying the generated recombinant FPV virus.

In another embodiment, the order of step a) and b) of the method of generating a recombinant FPV vector of any of the above embodiments can be changed such that step b) is the first step and a) the second.

In an additional aspect, the present invention relates to a method of inducing an immune response against a filovirus in a subject comprising administering to the subject:

(a) a first composition comprising an immunologically effective amount of a MVA vector comprising a nucleic acid encoding at least one antigenic determinant of a filovirus protein; and (b) a second composition comprising an immunologically effective amount of a MVA vector comprising a nucleic acid encoding at least one antigenic determinant of a filovirus protein;

OR (c) a first composition comprising an immunologically effective amount of a MVA vector comprising a nucleic acid encoding at least one antigenic determinant of a filovirus protein; and (d) a second composition comprising an immunologically effective amount of an FPV vector comprising a nucleic acid encoding at least one antigenic determinant of a filovirus protein wherein one of the compositions is a priming composition and the other composition is a boosting composition.

In an additional aspect, the present invention relates to a method of providing protective immunity or a protective immune response in a subject, the method comprising administering to the subject:

(a) a first composition comprising an immunologically effective amount of a MVA vector comprising a nucleic acid encoding an antigenic protein of at least one filovirus subtype, together with a pharmaceutically acceptable carrier; and (b) a second composition comprising an immunologically effective amount of a fowlpox vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the present invention relates to a method of providing protective immunity or a protective immune response in a subject comprising administering to the subject:

(a) a first composition comprising an immunologically effective amount of a MVA vector comprising a nucleic acid encoding antigenic proteins of at least two filovirus subtypes, together with a pharmaceutically acceptable carrier; and (b) a second composition comprising an immunologically effective amount of a MVA vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the present inventions relates to a method for production of filovirus-like particles in a subject comprising administering to the subject:

(a) an immunologically effective amount of a MVA vector comprising a nucleic acid encoding antigenic proteins of at least one filovirus glycoprotein and a filovirus virion protein 40 (VP40), together with a pharmaceutically acceptable carrier; and (b) an immunologically effective amount of a fowlpox vector or a MVA vector comprising a nucleic acid encoding an antigenic protein of a first filovirus subtype, together with a pharmaceutically acceptable carrier;

wherein one of the vectors is a priming vaccine and the other vector is a boosting vaccine.

In an additional aspect, the present inventions relates to a method for production of filovirus-like particles in a subject comprising administering to the subject:

(a) a first composition comprising an immunologically effective amount of a MVA vector comprising a nucleic acid encoding antigenic proteins of at least one filovirus glycoprotein and a filovirus virion protein 40 (VP40), together with a pharmaceutically acceptable carrier; and (b) a second composition comprising an immunologically effective amount of a fowlpox vector or a MVA vector comprising a nucleic acid encoding an antigenic protein of a first filovirus subtype, together with a pharmaceutically acceptable carrier;

wherein one of the compositions is a priming composition and the other composition is a boosting composition.

In an additional aspect, the invention relates to a method of inducing an enhanced immune response against a filovirus in a subject, the method comprising production of filovirus-like particles in the subject by administering to the subject:

(a) an immunologically effective amount of a MVA vector comprising a nucleic acid encoding antigenic proteins of at least one filovirus glycoprotein and a filovirus virion protein 40 (VP40), together with a pharmaceutically acceptable carrier; and (b) an immunologically effective amount of a fowlpox vector or a MVA vector comprising a nucleic acid encoding an antigenic protein of a first filovirus subtype, together with a pharmaceutically acceptable carrier;

wherein one of the vectors is a priming vaccine and the other vector is a boosting vaccine.

In an additional aspect, the invention relates to a method of inducing an enhanced immune response against a filovirus in a subject, the method comprising production of filovirus-like particles in the subject by administering to the subject:

(a) a first composition comprising an immunologically effective amount of a MVA vector comprising a nucleic acid encoding antigenic proteins of at least one filovirus glycoprotein and a filovirus virion protein 40 (VP40), together with a pharmaceutically acceptable carrier; and (b) a second composition comprising an immunologically effective amount of a fowlpox vector or a MVA vector comprising a nucleic acid encoding an antigenic protein of a first filovirus subtype, together with a pharmaceutically acceptable carrier;

wherein one of the compositions is a priming composition and the other composition is a boosting composition.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 shows the structure and genetic organization of the filovirus genome.

FIG. 3C shows the structure and genetic organization of MVA-mBN254A including the selection marker. FIG. 3D shows the structure and genetic organization of MVA-mBN368A including the selection marker.

FIG. 5A shows the structure and genetic organization of plasmid pBN433. The GP-MARV-Musoke was inserted under control of the promoter PrS into the BspEI/NheI site of pBNX197. In addition the plasmid also contains MVA-BN DNA sequences flanking the IGR 148/149 of the MVA-BN genome and the loxP-flanked selection cassette. The loxP sites allow the later elimination of the selection cassette by Cre recombinase-mediated recombination. FIG. 5C shows the structure and genetic organization of plasmid pBN385. The glycoprotein gene of Ebola virus Sudan (GP-SEBOV) and the Nucleoprotein of Ebola virus Ivory Coast (NP-EBOV-Cdl) were inserted under control of the synthetic promoters PrS and PrLE1 into the MluI/NheI sites of pBNX186. In addition, the plasmid also contains MVA-BN DNA sequences flanking the IGR 148/149 of the MVA-BN genome and a selection cassette flanked by F2 and F2rpt in order to allow the later elimination of the selection cassette via homologous recombination in the absence of selective pressure.

FIG. 7A and FIG. 7B show the results of vaccination with MVA-BN-Filo (MVA-mBN226B) following challenge with MARV-Musoke. FIG. 7A shows that vaccination with MVA-BN-Filo protected 100% of animals from challenge with MARV-Musoke. FIG. 7B shows clinical scores post-challenge; vaccinated animals challenged with MARV-Musoke showed no symptoms or histological changes associated with hemorrhagic fever and harbored no virus in liver, spleen, adrenal glands, lymph nodes, or lungs.

FIG. 10 shows ZEBOV-GP specific antibodies of cynomolgus macaques which received prime-boost vaccinations on Study Day 0 and 28 with MVA-BN-ZEBOV/GP (MVA-mBN254) at a dose of $5\times10^8$ $TCID_{50}$ (n=3), with MVA-BN-ZEBOV/GP-VP40 (MVA-mBN255) at a dose of $5\times10^8$ $TCID_{50}$ (n=3) according to Example 6. Results are presented as the geometric mean concentration (ng/ml) together with the standard error of the mean (SEM).

FIG. 11 shows neutralizing antibody responses of cynomolgus macaques which received three vaccinations on Study Day 0, 28 and with MVA-BN-ZEBOV/GP at a dose of $5\times10^8$ $TCID_{50}$ (n=2), or with MVA-BN-ZEBOV/GP-VP40 ($5\times10^8$ $TCID_{50}$, n=2). Additional animals (n=2) received TBS as negative control on Study Day 0 and 56. Sera were analyzed by ZEBOV-GP-specific pseudo virion neutralizing assay. Results are presented as individual antibody titer neutralizing 80% of ZEBOV-GP expressing VSV.

DETAILED DESCRIPTION OF THE INVENTION

Figure 1:
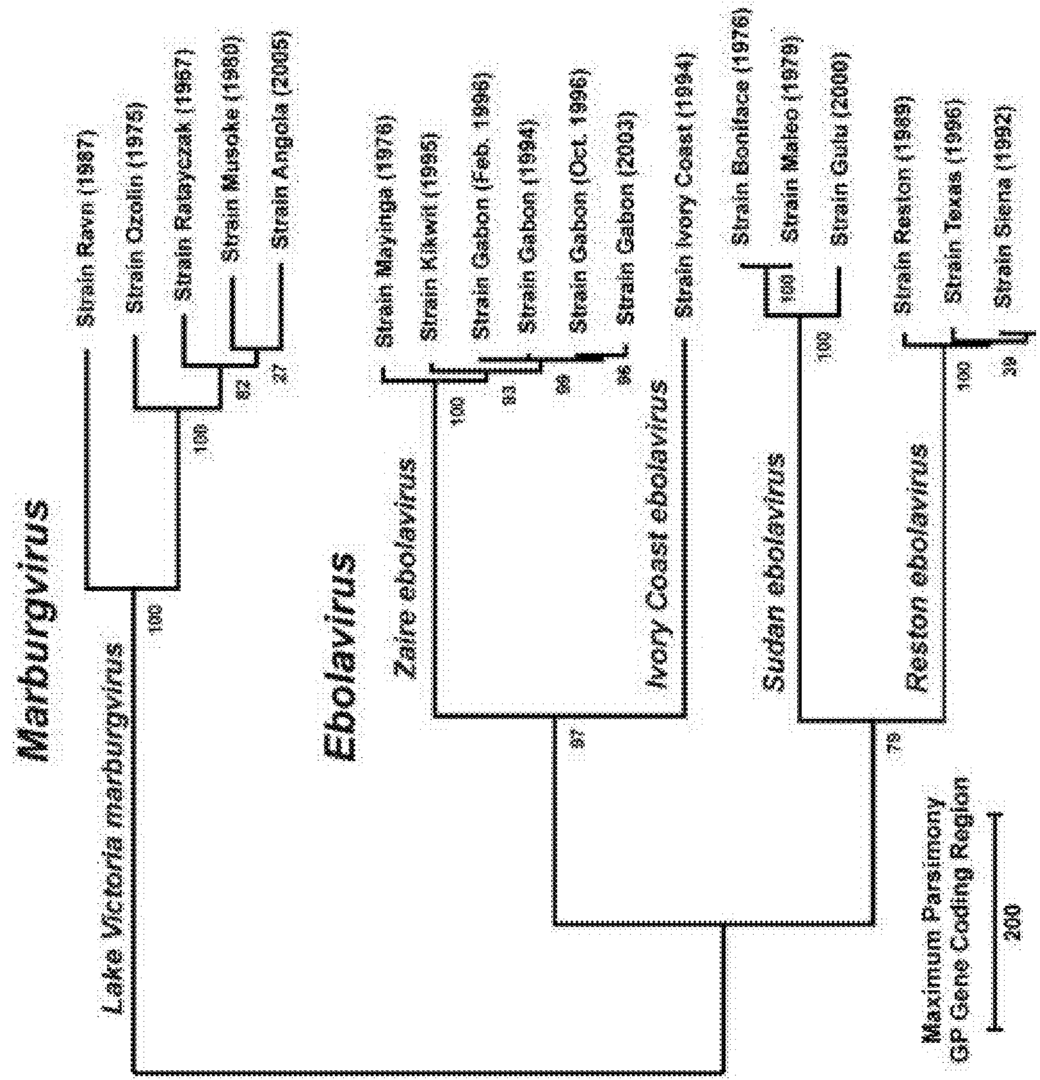
FIG. 1 shows a phylogenetic tree depicting the relationships between various identified filovirus strains. The tree was constructed using coding regions of envelope glycoprotein (GP) genes and the maximum parsimony method. Both the Ravn and Ratayczak strains of Marburg virus had a 23% fatality rate, while the Musoke and Angola strains had fatality rates ranging from 50% to 88%. The Sudan strain had a 41-65% fatality rate, and the Zaire strain had a 57-90% fatality rate. Both the Cote d'Ivoire and Reston strains have not yet caused disease in man, though Reston has caused disease in pigs.

The present inventors have found that a vaccine comprising a recombinant modified vaccinia virus Ankara (MVA) comprising a heterologous nucleotide sequence encoding an antigenic determinant of a Marburg virus (MARV) glycoprotein (GP) provides a filoviral vaccine capable of inducing both cellular and humoral responses sufficient to confer protective immunity to Marburg virus, as well as to smallpox. The insertion of additional heterologous nucleotide sequences encoding an antigenic determinant of an Ebola virus Zaire (ZEBOV) glycoprotein (GP), Ebola Virus Sudan (SEBOV) glycoprotein (GP), and/or an EBOV nucleoprotein (NP) into the recombinant MVA produces a multivalent vaccine capable of inducing immune responses to both MARV and EBOV, and even to multiple strains of MARV and/or EBOV, such as, for example Sudan Ebola virus (SEBOV) and Zaire Ebola virus (ZEBOV), the two types associated with the lethal forms of Ebola hemorrhagic fever. Thus, a recombinant MVA vector comprising a nucleotide sequence encoding an antigenic determinant of an EBOV GP reveals very good immune responses against Ebola strains. Moreover, the excellent safety profile of MVA and its derivatives (e.g., MVA-BN), as well as their ability to accommodate multiple heterologous nucleotide sequences enables the production of a safe single component multivalent pan-filovirus vaccine, in contrast to a number of multi-component vaccines in early stages of development (see below).

Given the fact that prior art attempts to generate an immune response against filoviruses, in particular in non-human primates against MARV and EBOV, failed, the present invention came as a surprise. It could not have been expected from what is taught and what was achieved in the prior art that a MVA-based vaccine would generate an immune response that confers protection in non-human primates against filovirus infection, in particular against MARV. Of course, from the data generated by the present inventors and their observations, it is more than reasonable and plausible to conclude that the MVA-based vaccine would also induce an immune response in humans. Indeed, the FDA accepts non-human primate models as proof that a vaccine which confers protection in these non-human primates is likewise suitable in humans.

The present inventors have also found that a vaccination regime comprising a recombinant modified vaccinia virus Ankara (MVA) comprising a heterologous nucleotide sequence encoding an antigenic determinant of EBOV, such as, for example Sudan Ebola virus (SEBOV) and/or Zaire Ebola virus (ZEBOV) in combination with a recombinant modified FPV comprising a heterologous nucleotide sequence encoding an antigenic determinant of EBOV, for example Sudan Ebola virus (SEBOV) and/or Zaire Ebola virus (ZEBOV) provides a filoviral vaccine capable of inducing both cellular and humoral responses sufficient to confer protective immunity.

In the study underlying the present invention it has also been found that the use of a MVA vector comprising a nucleic acid encoding an antigenic protein of at least one filovirus subtype, in particular a filovirus glycoprotein, and a fowlpox vector comprising at least one nucleic acid encoding an antigenic protein of a first filovirus glycoprotein as a heterologous prime and boost generates a protective immune response against a filovirus immunogen by induction of a high level of antibody response and an up to 5-fold higher cytotoxic CD8 T cell response, in particular wherein the MVA vector was used as at least one prime composition and the fowlpox as a boost composition.

The recombinant MVA and/or FPV may be either monovalent, i.e., comprising only one heterologous sequence encoding an antigenic determinant of EBOV, or multivalent, i.e., comprising at least two heterologous sequences encoding antigenic determinants of EBOV.

The invention thus provides vaccines or vaccine combinations for use in generating an immune response that confers dual protection or cross protection against infections by at least two filovirus subtypes in particular Marburg virus and/or Ebola virus subtypes and vaccines or vaccine combinations which can be used for manufacturing of a vaccine against at least two filovirus subtypes in particular Marburg virus and/or Ebola virus subtypes. Thus, vaccines for cross-protection against filoviruses such as Ebola Zaire-Mayinga and Zaire-Kikwit and/or Marburg-Musoke and Marburg-Angola could be provided. It is now also discovered for the first time, that immunization with a MVA vector expressing certain antigens such as the VP40 protein of ZEBOV together with other heterologous nucleotide sequences encoding for at least one surface glycoprotein of a filovirus, in particular of ZEBOV, can generate filovirus-like particles e.g., Ebola virus-like particles containing the filovirus glycoprotein on their surface. This was unexpected since it had been reported that transport of filoviral GP to the cell surface was largely inhibited by MVA (Sanger et al. J. Virol. Meth. 81, 29-35 (2001)). However, since filovirus particle budding occurs at the cell surface (Noda et al., *PLoS Pathog.* 2(9):e99 (2006)) efficient GP surface transport is required for formation of GP-containing filovirus-VLP. In the study underlying the present invention the recombinant MVA expressing filovirus virion protein 40 (VP40) and a glycoprotein e.g., GP-ZEBOV-Mayinga capable of producing VLPs induced an enhanced immune response with various prime-boost combinations and protected non-human primates against filovirus infection. The studies performed could also show that a homologous prime-boost based solely on recombinant MVA expressing a filovirus glycoprotein and a filovirus virion protein 40 (VP40) protein protected against a filovirus infection in non-human primates.

It has further been found that the use of a MVA vector comprising a nucleic acid encoding an antigenic glycoprotein of at least one filovirus subtype, in particular a glycoprotein of a Marburg virus and/or Ebola virus, and a nucleic acid encoding an antigenic protein of a virion protein 40 (VP40) as a heterologous prime boost with a fowlpox vector comprising at least one nucleic acid encoding an antigenic protein of a first filovirus glycoprotein generates an enhanced CD8 T cell response. In was further found that the use of a MVA vector comprising a nucleic acid encoding an antigenic glycoprotein of at least one filovirus subtype, in particular a glycoprotein of an Ebola virus and a nucleic acid encoding an antigenic protein of a virion protein 40 (VP40) induced a higher neutralizing antibody response in non-human primates e.g., already after priming which was further improved after boosting and thus generates an immune response against one or more filovirus infections, in particular Zaire-Mayinga and Zaire-Kikwit. It has also been shown that immunization with a MVA vector expressing certain antigens such as the filovirus virion protein 40 (VP40) together with a filovirus glycoprotein can produce VPLs that express a filovirus envelope glycoprotein lining the entire surface of the VLPs which resemble intact filovirus virions. In this way, incorporation of a nucleic acid encoding for a filovirus VP40 protein into the MVA vector was shown to enhance the immune response of the viral vector expressing the antigenic protein or proteins, in particular the MVA vector.

Reference will now be made in detail to exemplary embodiments of the invention, examples of which are illustrated in the accompanying drawings.

Recombinant MVA Virus

In one aspect, the present invention provides a recombinant modified vaccinia virus Ankara (MVA) comprising a nucleotide sequence encoding an antigenic determinant of a filovirus glycoprotein (GP), in particular an envelope glycoprotein. In another aspect, the present invention provides a recombinant MVA vector comprising a heterologous nucleotide sequence encoding an antigenic determinant of a filovirus glycoprotein, in particular an envelope glycoprotein, and a heterologous nucleotide sequence encoding an antigenic determinant of a further filovirus protein. MVA has been generated by more than 570 serial passages on chicken embryo fibroblasts of the dermal vaccinia strain Ankara (Chorioallantois vaccinia virus Ankara virus, CVA; for review see Mayr et al. (1975), *Infection* 3: 6-14) that was maintained in the Vaccination Institute, Ankara, Turkey for many years and used as the basis for vaccination of humans. However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells (Mayr et al. (1975)). It was shown in a variety of animal models that the resulting MVA was avirulent (Mayr, A. & Danner, K. (1978), *Dev. Biol. Stand.* 41:225-234). As part of the early development of MVA as a pre-smallpox vaccine, there were clinical trials using MVA-517 in combination with Lister Elstree (Stickl (1974), *Prev. Med.* 3:97-101; Stickl and Hochstein-Mintzel (1971), *Munch. Med. Wochenschr.* 113:1149-1153) in subjects at risk for adverse reactions from vaccinia. In 1976, MVA derived from MVA-571 seed stock (corresponding to the $571^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), *Zentralbl. Bacteriol.* (B) 167:375-390). MVA-572 was deposited at the European Collection of Animal Cell Cultures as ECACC V94012707.

As a result of the passaging used to attenuate MVA, there are a number of different strains or isolates, depending on the number of passages conducted in CEF cells. For example, MVA-572 was used in a small dose as a pre-vaccine in Germany during the smallpox eradication program, and MVA-575 was extensively used as a veterinary vaccine. MVA as well as MVA-BN lacks approximately 13% (26.6 kb from six regions) of the genome compared with ancestral CVA virus. The deletions affect a number of virulence and host range genes, as well as the gene for Type A inclusion bodies. MVA-575 was deposited on Dec. 7, 2000, at the European Collection of Animal Cell Cultures (ECACC) under Accession No. V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells (Blanchard et al. (1998), *J. Gen. Virol.* 79:1159-1167; Carroll & Moss (1997), *Virology* 238:198-211; U.S. Pat. No. 5,185,146; Ambrosini et al. (1999), *J. Neurosci. Res.* 55: 569). It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic: MVA was further passaged by Bavarian Nordic and is designated MVA-BN. A representative and preferred sample of MVA-BN was deposited on Aug. 30, 2000 at the European Collection of Cell Cultures (ECACC) under Accession No. V00083008. MVA-BN is further described in WO 02/42480 (US 2003/0206926) and WO 03/048184 (US 2006/0159699), both of which are incorporated by reference herein.

MVA-BN can attach to and enter human cells where virally-encoded genes are expressed very efficiently. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome (E. Harrer et al. (2005), *Antivir. Ther.* 10(2):285-300; A. Cosma et al. (2003), *Vaccine* 22(1):21-9; M. Di Nicola et al. (2003), *Hum. Gene Ther.* 14(14):1347-1360; M. Di Nicola et al. (2004), *Clin. Cancer Res.,* 10(16):5381-5390).

"Derivatives" or "variants" of MVA refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCaT (Boukamp et al (1988), *J. Cell Biol.* 106:761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699).

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO 02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

In a preferred embodiment, the recombinant MVA vector of any of the embodiments used for generating the recombinant virus is a MVA-BN virus or a derivative having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.

In another embodiment, the recombinant MVA vector of any of the embodiments used for generating the recombinant virus is MVA-BN as deposited at the European Collection of Animal Cell cultures (ECACC) under accession number V00083008.

MVA vectors useful for the present invention can be prepared using methods known in the art, such as those described in WO 02/042480 and WO 02/24224, both of which are incorporated by reference herein.

In another aspect, a MVA viral strain suitable for generating the recombinant virus may be strain MVA-572, MVA-575 or any similarly attenuated MVA strain. Also suitable may be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see WO 2011/092029).

Recombinant FPV

In one aspect, the present invention provides a recombinant FPV comprising a nucleotide sequence encoding an antigenic determinant of a filovirus glycoprotein (GP), in particular an envelope glycoprotein. In another aspect, the present invention provides a recombinant FPV comprising a heterologous nucleotide sequence encoding an antigenic determinant of a filovirus glycoprotein, in particular an envelope glycoprotein, and a heterologous nucleotide sequence encoding an antigenic determinant of a further filovirus protein.

An FPV according to the invention is a prototype species within the genus of the Avipoxvirus. Numerous FPV strains are described and are available for example from CEVA Laboratories, Cynamid Webster, Fort Dodge, Intercontinental Laboratories, Intervet (NOBILIS VARIOLE), Merial (DIFTOSEC CT strain), Schering-Plough, Select Laboratories, Solvay, Syntro-Zeon and Vineland Laboratories. FP1 is a Duvette strain modified to be used as a vaccine in one day old chickens. The strain is a commercial fowlpox virus vaccine strain designated 0 DCEP 25/CEP67/2309 October, 1980 and is available from Institute Merieux, Inc. FP5 is a commercial fowlpox virus vaccine strain of chicken embryo origin available from American Scientific Laboratories (Division of Schering Corp.) Madison, Wis., United States Veterinary License No. 165, serial No. 30321. Various attenuated strains of fowlpox virus are known such as FPV M (mild vaccine strain) and FPV S (standard vaccine strain) obtainable from Cyanamid Websters PtY, Ltd Australia. The US Department of Agriculture (USDA) challenge strain has been further described by C. L. Afonso et al., *J. Virol.*

74(8):3815-3831 (2000), 74(8):3815-3831 (2000). FP9 is a fowlpox strain used for vaccine purposes obtained in the late 1980s by Tomeley, Binns, Boursnell and Brown at the IAH Houghton Laboratories (St Ives, UK). It was derived from plaque purification of a virus that had been passaged 438 times in chicken embryo fibroblasts (CEF) culture from HP1 (A. Mayr & K. Malicki (1966), *Zentralbl Veterinarmed* (B) 13:1-13, Skinner et al. (2005), *Expert Res. Vaccines* 4(1): 63-76). Other attenuated strains are PDXVAC-TC as such described in S. Jenkins et al. (1991), *Aids Research and Human Retroviruses* 7(12):991:998. Deposited strains encompass for example fowlpox virus ATCC® VR-229 (typical fowlpox scabs from combs of chickens in New Jersey prior to 1928) and fowlpox virus ATCC® VR-250 (chicken, Kentucky, 1950).

In another aspect, a FPV viral strain suitable for generating the recombinant virus can be any strain mentioned supra or any similar FPV strain. In another aspect, the FPV is selected from the group of FP1, FP5, FP9, FPV M, FPV S, ATCC® VR-229, ATCC® VR-250, the USDA strain and PDXVAC-TC. In yet another embodiment, the FPV of any of the embodiments is an attenuated FPV.

An advantage of FPV is that the virus causes disease only in avian species, but is able to enter and express transgenes in mammalian cells, while being immunologically non-cross-reactive with vaccinia virus and can thus escape pre-existing immunity in smallpox-experienced humans.

Recombinant FPV vectors suitable for generating the recombinant FPV can be constructed by well-established methods. Live attenuated fowlpox viruses may be produced by multiple passage of the virus in avian cells. The preparation of the FPV vectors is described, for example in Michael J. P. Lawman and Patricia D. Lawman (eds.) *Cancer Vaccines*: Method and Protocols, Methods in Molecular Biology, vol. 1139, Chapter 32 Paul M. Howley, Kerrilyn R. Diener and John D. Hayball p. 407-427. The generation of recombinant FPV useful for virus-based vaccination strategy has also been described in EP 0 284 416 B1, WO 88/02022, WO 89/03429, WO 89/03879, WO89/07644, WO 89/12684, WO 90/02191, WO 91/02072, WO 89/03879 and WO 94/019014. The genome sequence and genome organization has been described by Afonso et al. and Laidlaw and Skinner (C. L. Afonso et al. (2000), *J. Virol.* 74(8):3815-3831, S. M. Laidlaw and M. A. Skinner (2004), *Journal of General Virology* 85:305-322). An exemplary genome sequence of FPV can be found in GenBank Accession No. AF198100.1.

Antigenic Determinants

The term “antigenic determinant” refers to any molecule that stimulates a host’s immune system to make an antigen-specific immune response, whether a cellular response or a humoral antibody response. Antigenic determinants may include proteins, polypeptides, antigenic protein fragments, antigens, and epitopes which still elicit an immune response in a host and form part of an antigen, homologues or variants of proteins, polypeptides, and antigenic protein fragments, antigens and epitopes including, for example, glycosylated proteins, polypeptides, antigenic protein fragments, antigens and epitopes, and nucleotide sequences encoding such molecules. Thus, proteins, polypeptides, antigenic protein fragments, antigens and epitopes are not limited to particular native nucleotide or amino acid sequences but encompass sequences identical to the native sequence as well as modifications to the native sequence, such as deletions, additions, insertions and substitutions.

The term “epitope” refers to a site on an antigen to which B- and/or T-cells respond, either alone or in conjunction with another protein such as, for example, a major histocompatibility complex (“MHC”) protein or a T-cell receptor. Epitopes can be formed both from contiguous amino acids or noncontiguous amino acids juxtaposed by secondary and/or tertiary folding of a protein. Epitopes formed from contiguous amino acids are typically retained on exposure to denaturing solvents, while epitopes formed by tertiary folding are typically lost on treatment with denaturing solvents. An epitope typically includes at least 5, 6, 7, 8, 9, 10 or more amino acids—but generally less than 20 amino acids—in a unique spatial conformation. Methods of determining spatial conformation of epitopes include, for example, x-ray crystallography and 2-dimensional nuclear magnetic resonance. See, e.g., “Epitope Mapping Protocols” in Methods in Molecular Biology, Vol. 66, Glenn E. Morris, Ed (1996).

Preferably, a homologue or variant has at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% identity with the referenced protein, polypeptide, antigenic protein fragment, antigen and epitope at the level of nucleotide or amino acid sequence.

Techniques for determining sequence identity between nucleic acids and amino acids are known in the art. Two or more sequences can be compared by determining their “percent identity.” The percent identity of two sequences, whether nucleic acid or amino acid sequences, is the number of exact matches between two aligned sequences divided by the length of the shorter sequences and multiplied by 100.

“Percent (%) amino acid sequence identity” with respect to proteins, polypeptides, antigenic protein fragments, antigens and epitopes described herein is defined as the percentage of amino acid residues in a candidate sequence that are identical with the amino acid residues in the reference sequence (i.e., the protein, polypeptide, antigenic protein fragment, antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full-length of the sequences being compared.

The same applies to “percent (%) nucleotide sequence identity”, mutatis mutandis.

For example, an appropriate alignment for nucleic acid sequences is provided by the local homology algorithm of Smith and Waterman, (1981), *Advances in Applied Mathematics* 2:482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), *Nucl. Acids Res.* 14(6):6745-6763. An exemplary implementation of this algorithm to determine percent identity of a sequence is provided by the Genetics Computer Group (Madison, Wis.) in the “BestFit” utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+ GenBank CDS translations+Swiss protein+Spupdate+PIR. Details of these programs can be found at the following internet address: http://wvw.ncbi.nlm.qov/cqi-bin/BLAST.

In some embodiments, the heterologous nucleic acid encodes antigenic domains or antigenic protein fragments rather than the entire antigenic protein. These fragments can be of any length sufficient to be antigenic or immunogenic. Fragments can be at least 8 amino acids long, preferably 10-20 amino acids, but can be longer, such as, e.g., at least 50, 100, 200, 500, 600, 800, 1000, 1200, 1600, 2000 amino acids long, or any length in between.

In some embodiments, at least one nucleic acid fragment encoding an antigenic protein fragment or immunogenic polypeptide thereof is inserted into the viral vector of the invention. In another embodiment, about 2-6 different nucleic acids encoding different antigenic proteins are inserted into one or more of the viral vectors. In some embodiments, multiple immunogenic fragments or subunits of various proteins can be used. For example, several different epitopes from different sites of a single protein or from different proteins of the same strain, or from a protein orthologue from different strains can be expressed from the vectors.

Definitions

It must be noted that, as used herein, the singular forms "a", "an", and "the", include plural references unless the context clearly indicates otherwise. Thus, for example, reference to "an antigenic determinant" includes one or more antigenic determinants and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), whenever used herein in the context of an aspect or embodiment of the present invention may be substituted with the term "consisting of", though less preferred.

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

The term "substantially similar" in the context of the filovirus antigenic proteins of the invention indicates that a polypeptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "subtype" herein can be replaced with "species". It includes strains, isolates, clades or variants of any filovirus such as Marburg or Ebola virus. The terms "strain" "clade" or "isolate" are technical terms, well known to the practitioner, referring to the taxonomy of microorganisms. The taxonomic system classifies all so far characterised microorganisms into the hierarchic order of Families, Genera, Species, Strains (Fields Virology, ed. by Fields B. N., Lippincott-Raven Publishers, 4th edition 2001). While the criteria for the members of a Family is their phylogenetic relationship, a Genera comprises all members which share common characteristics, and a Species is defined as a polythetic class that constitutes a replicating lineage and occupies a particular ecological niche. The term “strain” or “clade” describes a microorganism, i.e., virus, which shares common characteristics, like basic morphology or genome structure and organization, but varies in biological properties, like host range, tissue tropism, geographic distribution, attenuation or pathogenicity. For example there are five Ebola virus subtypes known, i.e., Zaire Ebola virus, Sudan Ebola virus, Reston Ebola virus, Bundibugyo Ebola virus and Ivory Coast Ebola virus. Zaire Ebola virus strains are for example Zaire-Mayinga, Zaire-Kikwit, Zaire-Gabon (1994), Zaire-Gabon (February 1996), Zaire-Gabon (October 1996). There is only one Marburg virus subtype or species i.e., Lake Victoria marburgvirus know so far with the strains including Marburg-Musoke and Marburg-Angola. For further strains or isolates see also FIG. 1.

The term “$TCID_{50}$” is the abbreviation of “tissue culture infectious dose”, that amount of a pathogenic agent that will produce pathological change in 50% of cell cultures inoculated, expressed as $TCID_{50}$/ml. A method for determining $TCID_{50}$ is well known to the person skilled in the art. It is for example described in e.g., Example 2 of WO 03/053463.

The term “subject” as used herein is a living multi-cellular vertebrate organisms, including, for example, humans, non-human mammals and (non-human) primates. The term “subject” may be used interchangeably with the term “animal” herein.

The term “filovirus-caused disease” referred to in any of the embodiments can be any disease caused by an infection of any filovirus strain, isolate or variant thereof as mentioned herein or any combination of any filovirus strain, isolate or variant (as mentioned anywhere supra or infra and/or in any of the embodiments supra or infra) thereof.

As used herein, the term “enhanced” when used with respect to an immune response against a filovirus, such as an antibody response (e.g., neutralizing antigen specific antibody response or ZEBOV-GP-specific antibody response), a cytokine response or a CD8 T cell response (e.g., immunodominant CD8 T cell response), refers to an increase in the immune response in an animal administered with a homologous prime-boost combination vaccine of MVA relative to the corresponding immune response observed from the animal administered with a homologous prime-boost combination vaccine of MVA vectors, wherein the MVA vectors do not express any filovirus virion protein 40 or refers to an increase in the immune response in an animal administered with a heterologous prime-boost combination vaccine of MVA and FPV vectors according to the invention, relative to the corresponding immune response observed from the animal administered with a heterologous prime-boost combination vaccine of MVA and FPV vectors according to the invention, wherein the MVA vector does not express any filovirus virion protein 40. Preferably, “enhanced” when used with respect to an immune response, such as an antibody response e.g., neutralizing antibody response, a cytokine response or a CD8 T cell response, refers to an increase in the immune response in an animal administered with a heterologous prime-boost combination vaccine of MVA as a prime and FPV vectors as boost according to the invention, relative to the corresponding immune response observed from the animal administered with a reverse prime-boost combination, wherein the FPV vector is provided as a prime and the MVA vector is provided to boost the immune response, using the same prime-boost interval.

In the context of this invention, an “immunodominant CD8 T cell response” means the major CD8 T cell response of a host against a recombinant antigen encoded by a MVA and/or FPV vector. Thus, an immunodominant CD8 T cell response against a recombinant antigen encoded by a homologous prime-boost of recombinant MVA or heterologous prime-boost of recombinant MVA and FPV can be generated that is greater than the CD8 T cell response against any recombinant antigen of the recombinant MVA or FPV, wherein the MVA vector does not express any filovirus virion protein 40.

The level of the CD8 T cell response can be determined by methods well known in the art such as but not limited to an ELISPOT assay (e.g., interferon gamma (IFN-γ) ELISPOT. Protocols are for examples described in Current Protocols in Immunology (John Wiley & Son, Inc. (1994) (see, e.g., Chapter 6, Section 19: ELISPOPT Assay to Detect Cytokine-secreting Murine and Human Cells, Supplement 10) or by Schneider, et al., *Nat. Med.* 4:397-402 (1998)) and, for example, by the techniques set forth in the examples for a specific virus of the invention. Other suitable assays comprise an ICS assay, which analyzes levels of intracellular cytokine for CD8 T cell activity. For example, the CD8 T cell response can comprise an antigen specific CD8 T cell response that is more than 50%, such as 51%, 60%, 70%, 80%, 90% or 100% of the total antigen specific T-cell responses in the animal subject. Preferably, the CD8 T cell response also represents 0.1% or more, such as 0.1%, 0.2%, 0.3%, 0.4%, 0.5%, or more of the total cytokine responses in the animal subject. In some embodiments, after the second or third boost, the recombinant viral vectors according to the invention induce a CD8 T cell response in the host against the encoded antigen that is at least 0.5%, 1%, 5%, 10%, 15%, 20%, 25%, or 30% of the total CD8 T cell compartment.

The level of antibody responses can be determined by methods known in the art. Any suitable plaque reduction neutralization titer (PRNT) assay can be used to determine whether a polypeptide (or polynucleotide expressing such a polypeptide) induces one or more neutralizing antibodies against one or more filovirus antigens of one or more filovirus subtype. An exemplary plaque reduction neutralization titer assay for filoviruses is described in the examples. Other PRNT methods and formats are well known to those of ordinary skill in the art.

Filovirus Proteins

As used interchangeably herein, the terms “glycoprotein gene” or “GP gene” refer to the gene, or to a homologue or variant of the gene, encoding the glycoprotein, in particular the transmembrane envelope glycoprotein, in any filovirus strain or isolate, even though the exact sequence and/or genomic location of the glycoprotein gene may differ between strains or isolates. For example, in the Maleo strain of SEBOV (SEBOV-Maleo), the glycoprotein gene (GP-SEBOV-Maleo gene) comprises nucleotides 120-1004 and 1004-2149 (endpoints included) as numbered in GenBank Accession Number U23069.1. The EBOV transcripts undergo editing during transcription such that some nucleotides are read twice. The GP-SEBOV-Maleo gene further comprises a protein coding open reading frame (ORF) spanning nucleotides 120-1004 and 1004-2149 (endpoints included) as numbered in GenBank Accession Number U23069.1. The nucleotide sequence of the GP-SEBOV-Maleo gene is set forth in SEQ ID NO:1 (GenBank Accession No. U23069.1).

As used herein, a “homologue” or “variant” preferably has at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% nucleotide sequence identity with the referenced gene, protein, polypeptide, antigenic protein fragment, antigen and epitope. The term "homologue" or "variant" also encompasses deleted, truncated or otherwise mutated versions of the genes and proteins, respectively. By way of example, encompassed are, e.g., soluble forms of the GP-EBOV or GP-MARV proteins lacking the signal peptide as well as the transmembrane and/or cytoplasmic domains of the full-length GP-EBOV or GP-MARV proteins.

As used interchangeably herein, the terms "glycoprotein" or "GP" refer to the glycoprotein, in particular the transmembrane envelope glycoprotein, or to a homologue or variant of the glycoprotein.

The amino acid sequence of GP-EBOV-Maleo is set forth in SEQ ID NO:2 (amino acid sequence of GenBank Accession No. U23069.1). The GP-SEBOV-Maleo protein comprises a signal peptide, an extracellular domain, a transmembrane domain, and a cytoplasmic domain (see, e.g., UniProtKB/Swiss-Prot Accession No. Q66798). The signal peptide of GP-SEBOV-Maleo protein consists of amino acids 1-32 of SEQ ID NO:2; the extracellular domain of GP-SEBOV-Maleo protein consists of amino acids 33-650 of SEQ ID NO:2 or amino acids 1-650 of SEQ ID NO:2; the transmembrane domain of GP-SEBOV-Maleo protein consists of amino acids 651-671 of SEQ ID NO:2; and the cytoplasmic domain of GP-SEBOV-Maleo protein consists of amino acids 672-676 of SEQ ID NO:2.

The nucleic acid encoding the amino acid sequence of GP-ZEBOV-Mayinga is set forth in SEQ ID NO:19. The GP-ZEBOV-Mayinga comprises a protein as set forth in SEQ ID NO:20 (GenBank Accession Number ABX75367.1).

Likewise, also the terms "nucleoprotein gene" or "NP gene", as used interchangeably herein, refer to the gene, or to a homologue or variant of the gene, encoding the nucleoprotein in any filovirus strain or isolate, even though the exact sequence and/or genomic location of the nucleoprotein gene may also differ between strains or isolates. For example, in the Boniface strain of SEBOV (SEBOV-Boniface), the nucleoprotein gene (NP-SEBOV-Boniface gene) comprises nucleotides 383-2599 (endpoints included) as numbered in GenBank Accession Number AF173836.1. The NP-SEBOV-Boniface gene further comprises a protein coding open reading frame (ORF) spanning nucleotides 383-2599 (endpoints included) as numbered in GenBank Accession Number AF173836.1. The nucleotide sequence of the NP-SEBOV-Boniface gene is set forth in SEQ ID NO:3 (GenBank Accession No. AF173836.1).

The amino acid sequence of NP-EBOV-Boniface is set forth in SEQ ID NO:4 (amino acid sequence of GenBank Accession No. AF173836.1). The NP-SEBOV-Boniface protein comprises a coiled coil domain (see, e.g., UniProtKB/Swiss-Prot Accession No. Q9QP77). The coiled coil domain of NP-SEBOV-Boniface protein consists of amino acids 334-363 of SEQ ID NO:4.

In certain embodiments, the nucleic acid encoding an antigenic determinant, preferably an antigenic protein, more preferably of any of the proteins as mentioned supra or infra is a full-length protein.

Recombinant MVA and FPV

Provided herein are recombinant poxviruses (e.g., MVA or MVA-BN or FPV) comprising heterologous or foreign nucleic acid sequences derived from EBOV and/or MARV incorporated in a variety of insertion sites in the poxviral (e.g., MVA or MVA-BN or FPV) genome. The heterologous nucleic acids can encode one or more foreign proteins and/or foreign antigens including, for example, viral antigens.

Generally, a "recombinant" MVA or FPV as described herein refers to MVAs/FPVs that are produced by standard genetic engineering methods, i.e., MVAs/FPVs of the present invention are thus genetically engineered or genetically modified MVAs/FPCs. The term "recombinant MVA or FPV" thus includes MVAs/FPVs which have stably integrated recombinant nucleic acid, preferably in the form of a transcriptional unit, in their genome. A transcriptional unit may include a promoter, enhancer, terminator and/or silencer. Recombinant MVAs/FPVs of the present invention may express heterologous antigenic determinants, polypeptides or proteins (antigens) upon induction of the regulatory elements. The term "MVA/FPV" in the context of any of the embodiments of the invention encompasses both individual and combined options for MVA, FPV or MVA and FPV.

As used herein, a "heterologous" gene, nucleic acid, antigen, or protein is understood to be a nucleic acid or amino acid sequence which is not present in the wild-type poxviral genome (e.g., MVA or MVA-BN or FPV). The skilled person understands that a "heterologous gene", when present in a poxvirus such as MVA or MVA-BN or FPV, is to be incorporated into the poxviral genome in such a way that, following administration of the recombinant poxvirus to a host cell, it is expressed as the corresponding heterologous gene product, i.e., as the "heterologous antigen" and/or "heterologous protein." Expression is normally achieved by operatively linking the heterologous gene to regulatory elements that allow expression in the poxvirus-infected cell. Preferably, the regulatory elements include a natural or synthetic poxviral promoter.

In one aspect, the recombinant MVA/FPV vector according to the invention comprises a heterologous nucleotide sequence encoding an antigenic determinant of a filovirus protein selected from an Ebola virus (EBOV) and/or a Marburg virus (MARV). In another embodiment, the recombinant MVA/FPV vector according to the invention comprises a heterologous nucleotide sequence encoding an antigenic determinant of one or more antigenic determinant(s) of the filovirus protein (e.g., EBOV protein) which is selected from one or more EBOV subtypes selected from the group consisting of Zaire Ebola virus (ZEBOV), Sudan Ebola virus (SEBOV), Cote d'Ivoire Ebola virus (EBOV-Cdl, also called Tai Forest virus or TAFV), Reston Ebola virus (REBOV) and Bundibugyo Ebola virus (BEBOV).

According to another embodiment, the recombinant MVA/FPV vector according to the invention comprises one or more antigenic determinant(s) of a filovirus protein, preferably EBOV protein, MARV protein or full-length protein thereof, selected from the group of Zaire-Mayinga, Zaire-Kikwit, Zaire-Gabon, Cote d'Ivoire Ebola virus, Sudan-Boniface, Sudan-Maleo, Sudan-Gulu, Marburg-Ravn, Marburg-Ozolin, Marburg-Ratayczak, Marburg-Musoke, Marburg-Angola.

Preferably, the antigenic determinant of the filovirus protein (e.g., selected from the group of Zaire-Mayinga, Zaire-Kikwit, Zaire-Gabon, Cote d'Ivoire Ebola virus, Sudan-Boniface, Sudan-Maleo, Sudan-Gulu, Marburg-Ravn, Marburg-Ozolin, Marburg-Ratayczak, Marburg-Musoke, Marburg-Angola) is selected from the group consisting of an envelope glycoprotein (GP), nucleoprotein (NP), virion protein 35 (VP35), virion protein 40 (VP40), virion protein 30 (VP30), virion protein 24 (VP24), and RNA-directed RNA polymerase protein (L).

In another embodiment, the antigenic determinant of the filovirus protein is an envelope glycoprotein (GP), preferably at least an envelope glycoprotein (GP) and a virion protein 40 (VP40).

In another embodiment, the antigenic determinant of the filovirus protein is an envelope glycoprotein (GP) selected from the group of ZEVOV and SEBOV, preferably at least an envelope glycoprotein (GP) and a virion protein 40 (VP40), wherein the GP and VP40 are derived from the same strain, preferably wherein the same strain is selected from the group of ZEBOV and SEBOV.

In another embodiment, the antigenic determinant of the filovirus protein is at least an envelope glycoprotein (GP) and a virion protein 40 (VP40), wherein the GP and VP40 are derived from a different isolate or the same isolate, preferably wherein the different or the same isolate is selected from the group of Zaire-Mayinga, Zaire-Kikwit, Zaire-Gabon, Cote d'Ivoire Ebola virus, Sudan-Boniface, Sudan-Maleo, Sudan-Gulu, Marburg-Ravn, Marburg-Ozolin, Marburg-Ratayczak, Marburg-Musoke and Marburg-Angola, preferably wherein the isolate is selected from the group of Zaire-Mayinga, Sudan-Gulu, Marburg-Musoke and Marburg-Angola, most preferably wherein the isolate is selected from the group of Zaire-Mayinga, Sudan-Gulu and Marburg-Musoke.

In another preferred embodiment, the recombinant MVA/FPV vector according to the invention comprises a nucleotide sequence encoding an antigenic determinant of two, three, four or more Ebola and/or Marburg subtypes.

Another preferred embodiment covers the recombinant MVA/FPV vector according to any of the embodiments of the invention which comprises an antigenic determinant of two, three, four or more filovirus proteins selected from the group consisting of envelope glycoprotein (GP), nucleoprotein (NP), virion protein 35 (VP35), virion protein 40 (VP40), virion protein 30 (VP30), virion protein 24 (VP24), and RNA-directed RNA polymerase protein (L).

In a preferred embodiment, the recombinant MVA/FPV vector according to any of the embodiments of the invention comprises an antigenic determinant of one, two, three, four or more filovirus protein selected from the group consisting of SEQ ID NO:2, SEQ ID NO:4, SEQ ID NO:6, SEQ ID NO:20, SEQ ID NO:29, SEQ ID NO:31, SEQ ID NO:34 and SEQ ID NO:37.

In a preferred embodiment, the recombinant MVA/FPV vector according to any of the embodiments of the invention comprises an antigenic determinant of a filovirus protein selected from the group consisting of SEQ ID NO:2, SEQ ID NO:4, SEQ ID NO:6, SEQ ID NO:20, SEQ ID NO:29, SEQ ID NO:31, SEQ ID NO:34 and SEQ ID NO:37.

In another embodiment, the recombinant MVA/FPV vector according to any of the embodiments of the invention comprises an antigenic determinant of a filovirus protein consisting of SEQ ID NO: 20.

In another embodiment, the recombinant MVA/FPV vector according to any of the embodiments of the invention comprises an antigenic determinant of a filovirus protein selected from the group consisting of SEQ ID NO: 20 and SEQ ID NO: 34.

In another embodiment, the recombinant MVA/FPV vector according to any of the embodiments of the invention comprises an antigenic determinant of a filovirus protein selected from the group consisting of SEQ ID NO:6, SEQ ID NO:20, SEQ ID NO:31 and SEQ ID NO:34.

In another embodiment, the recombinant MVA/FPV vector according to any of the embodiments of the invention comprises an antigenic determinant of a filovirus protein selected from the group consisting of SEQ ID NO:6, SEQ ID NO: 20, SEQ ID NO:29, SEQ ID NO:31 and SEQ ID NO:34.

In another preferred embodiment, the recombinant MVA/FPV vector according to any of the embodiments of the invention comprises an antigenic determinant of a filovirus protein selected from the group consisting of SEQ ID NO:6, SEQ ID NO:20, SEQ ID NO:29, SEQ ID NO:31, SEQ ID NO:34 and SEQ ID NO:37.

In another preferred embodiment, the MVA vector according to any of the embodiments of the invention comprises a heterologous nucleotide sequence encoding an antigenic determinant of a filovirus protein consisting of SEQ ID NO:29 and/or SEQ ID NO:6, SEQ ID NO:20, SEQ ID NO:31.

In another preferred embodiment, the MVA vector according to any of the embodiments of the invention comprises a nucleotide sequence comprising SEQ ID NO:28 and/or SEQ ID NO:5, SEQ ID NO:19, SEQ ID NO:30.

In another preferred embodiment, the MVA vector according to any of the embodiments of the invention comprises a nucleotide sequence encoding an antigenic protein of a filovirus virion protein 40 (VP40) comprising SEQ ID NO:33 or a nucleotide sequence encoding the protein sequence comprising SEQ ID NO:34.

In another preferred embodiment, the recombinant MVA vector according to any of the embodiments of the invention comprising a nucleotide sequence selected from the group of a) SEQ ID NO:5, SEQ ID NO:19 and SEQ ID NO:30, b) SEQ ID NO:5, SEQ ID NO:19, SEQ ID NO:28 and SEQ ID NO:30 and c) SEQ ID NO:19 and SEQ ID NO:33.

In another aspect, the present invention comprises a recombinant MVA vector or FPV vector comprising a heterologous nucleotide sequence encoding an antigenic determinant of a filovirus glycoprotein, in particular a filovirus envelope glycoprotein.

The filovirus glycoprotein may encode a GP-MARV or a GP-EBOV.

For the embodiments as described herein the glycoprotein of MARV may be derived from MARV-Musoke, preferably the full-length MARV-Musoke, which, in turn, may be derived from the Lake Victoria strain or isolate of MARV-Musoke. The GP-MARV may also be derived from MARV-Ravn MARV-Ozolin, MARV-Ratayczak or from MARV-Angola. A nucleotide sequence encoding a full-length GP-MARV-Musoke is shown in SEQ ID NO:5 encoding amino acids 1 to 681 or 19 to 681 of SEQ ID NO:6. In a preferred embodiment, the GP-MARV-Musoke comprises the nucleotide sequence of SEQ ID NO:5 preferably encoding the protein of SEQ ID NO:6. In certain embodiments, the GP-MARV-Musoke is truncated wherein the truncated GP-MARV-Musoke may comprise only the extracellular domain of the envelope glycoprotein, comprising amino acids 1 to 648 or amino acids 19 to 648 of SEQ ID NO:6 (GenBank Accession No. ABA87127.1). In other embodiments as described herein the glycoprotein of MARV may be derived from MARV-Angola, preferably the full-length GP-MARV-Angola. In a preferred embodiment, the GP-MARV-Angola comprises the nucleotide sequence of SEQ ID NO:36 encoding amino acids of SEQ ID NO:37.

The glycoprotein of EBOV may be GP-SEBOV or may be derived from GP-ZEBOV, in particular from the Mayinga strain of GP-ZEBOV (GP-ZEBOV-Mayinga). The full-length GP-ZEBOV-Mayinga comprises the nucleotide sequence of SEQ ID NO:19 encoding the amino acid sequence of SEQ ID NO:20. In a preferred embodiment, the GP-ZEBOV-Mayinga comprises the nucleotide sequence of SEQ ID NO:19 preferably encoding the protein of SEQ ID NO:20. The GP-EBOV may also be GP-BEBOV, GP-EBOV-Cdl or GP-EBOV-Reston. The GP-ZEBOV may be truncated and may comprise the nucleotide sequence of SEQ ID NO:19 modified to encode amino acids 1-636 of SEQ ID NO:20 or modified to delete the mucin domain spanning amino acids 314 to 464 of SEQ ID NO:20.

The GP-SEBOV may be derived from the Gulu strain of GP-SEBOV (GP-SEBOV-Gulu). In certain embodiments, the GP-SEBOV comprises the nucleotide sequence of SEQ ID NO:30, preferably encoding the amino acid sequence of SEQ ID NO:31.

The recombinant MVA/FPV according to the present invention can also further comprise tetanus toxoid fragment C sequence. In a preferred embodiment, GP-MARV-Musoke, in particular the full-length MARV-Musoke GP, further comprises tetanus toxoid fragment C. A tetanus toxoid fragment C may comprise the nucleotide sequence of SEQ ID NO:7 encoding the amino acid sequence of SEQ ID NO:8. In certain embodiments, the truncated GP-MARV-Musoke further comprises tetanus toxoid fragment C (TTC) which may comprise the nucleotides 2281-3642 of the nucleotide sequence of SEQ ID NO:7 encoding amino acids 760-1213 of the amino acid sequence of SEQ ID NO:8.

The recombinant MVA/FPV vector according to the present invention can additionally comprise an immunostimulatory or co-stimulatory molecule. In a preferred embodiment, the heterologous nucleotide sequence encoding an antigenic determinant of a GP-MARV-Musoke further comprises one or more immunostimulatory molecules. In certain embodiments, the one or more immunostimulatory molecules is human CD40 ligand (hCD40L) which may comprise SEQ ID NO:9 encoding the amino acid sequence of SEQ ID NO:10. In certain embodiments, the one or more immunostimulatory molecule(s) is a fusion protein comprising the sushi domain of human interleukin-15 receptor (hIL15R-Sushi) which may comprise SEQ ID NO:11 encoding the amino acid sequence of SEQ ID NO:12.

The one or more immunostimulatory molecules may also be lymphocyte function-associated antigen 3 (LFA-3, or CD58), intercellular adhesion molecule 1 (ICAM-1, or CD54) and B7.1 (CD80), collectively known as the triad of costimulatory molecules (i.e., 'TRICOM'). "TRICOM" as used herein is an abbreviation for Triad of COstimlatory Molecules consisting of B7-1 (also known as CD80), intracellular adhesion molecule-1 (ICAM-1, also known as CD54) and lymphocyte function-associated antigen-3 (LFA-3, also known as CD58), included in the recombinant viral vectors (e.g., poxviral vectors) expressing a specific antigen in order to increase the antigen-specific immune response. The individual components of TRICOM can be under the control of the same or different promoters, and can be provided on the same vector with the specific antigen or on a separate vector. Exemplary vectors are disclosed, for example, in Hodge et al., "A Triad of Costimulatory Molecules Synergize to Amplify T-Cell Activation," *Cancer Res.* 59:5800-5807 (1999) and U.S. Pat. No. 7,211,432 B2, both of which are incorporated herein by reference. The LFA-3 may comprise the nucleotide sequence of SEQ ID NO:13 encoding the amino acid sequence of SEQ ID NO:14, the ICAM-1 may comprise the nucleotide sequence of SEQ ID NO:15 encoding the amino acid sequence of SEQ ID NO:16, and the B7.1 may comprise the nucleotide sequence of SEQ ID NO:17 encoding the amino acid sequence of SEQ ID NO:18.

The recombinant MVA/FPV according to the present invention may also additionally comprise a membrane anchor sequence such as the vaccinia virus gene B5m comprising the nucleotide sequence of SEQ ID NO:21 encoding the amino acid sequence of SEQ ID NO:22. In particular, the antigenic determinant as described herein may preferably be operably linked to a membrane anchor such as the B5m. Thus, when used herein that the recombinant MVA/FPV comprises a membrane anchor sequence, it is meant that an antigenic determinant comprised by the recombinant MVA/FPV is preferably operably linked to the membrane anchor. A membrane anchor refers to any polypeptide capable of anchoring heterologous polypeptides to the outer face of the cell membrane. Preferably, the membrane anchor comprises the cytoplasmic and transmembrane domains of Vaccinia virus B5R protein, termed herein as the "B5R anchor" or "B5m" As defined, a B5R anchor refers to the 42-amino-acid C-terminal segment of the B5R protein from any type of Vaccinia virus, for example, the WR strain (Katz et al. *J Virol.* 71(4):3178-87 (1997)) or more preferably a MVA. In addition, B5R anchor variants having at least 80%, such as at least 85%, for example at least 90%, or at least 95%, such as at least 98% sequence identity with respect to the reference B5R anchor sequence are also included in the present invention. A preferred anchor sequence is shown in SEQ ID NO: 21, its translation product is also shown in SEQ ID NO: 22.

In a preferred embodiment, the full-length and/or truncated GP-ZEBOV further comprises vaccinia virus gene B5m.

In another aspect, the present invention comprises a recombinant MVA/FPV vector comprising a heterologous nucleotide sequence encoding an antigenic determinant of a filovirus glycoprotein as described above, and further comprises heterologous nucleotide sequences encoding additional filovirus proteins required to form virus-like particles (VLP). In one embodiment, the additional heterologous nucleotide sequence encoding filovirus protein required to form VLPs can be VP40. In certain embodiments, the additional filovirus proteins required to form virus-like particles or enhancing formation of VLPs are NP-EBOV and VP40-EBOV wherein these proteins may be derived from the strains as indicated above. Preferably, the filovirus nucleoprotein (e.g., NP-EBOV) and a filovirus virion protein 40 (e.g., VP40-EBOV) are derived from the same filovirus strain. By vaccinating non-human primates with a recombinant MVA expressing GP and VP40 (either in addition or without expressing NP) and which is capable of generating GP-containing EBOV-VLPs from infected cells the inventors could achieve protection against filovirus challenge in non-human primates. The production of virus-like particles in the animals being vaccinated creates an additional vaccine modality closely mimicking the viral particles present in a bona fide filoviral infection. Such recombinant MVA filo VLP vaccination stimulated both the humoral and cellular immune response and thus protected against filovirus challenge. A further advantage of vaccination with an attenuated MVA virus providing filoviral VLPs is to circumvent the need for purification of virus-like particles for inoculation and the additional MVA mediated immune stimulation. The use of a filovirus nucleoprotein (e.g., NP-EBOV) and a filovirus virion protein 40 (e.g., VP40-EBOV) derived from the same strain is of advantage for enhancing the formation of VLPs, preferably for generating homogenous GP spike decorated VLPs with a homogenous diameter for closely mimicking the viral particles and improving protection against a filovirus infection.

The present invention also relates to a recombinant MVA/FPV vector comprising a heterologous nucleotide sequence encoding an antigenic determinant of a filovirus glycoprotein and a heterologous nucleotide sequence encoding an antigenic determinant of a further filovirus protein. The nucleotide sequence encoding an antigenic determinant of a further filovirus protein may encode one or more filovirus proteins selected from the group consisting of nucleoprotein (NP), virion protein 35 (VP35), virion protein 40 (VP40), virion protein 30 (VP30), virion protein 24 (VP24), and RNA-directed RNA polymerase protein (L). Said genes and proteins, respectively, can be derived from the one or more filovirus strains described above. The NP-EBOV-Cdl of certain embodiments comprises the nucleotide sequence of SEQ ID NO:28 encoding the amino acid sequence of SEQ ID NO:29.

In certain embodiments, VP40 is selected from MARV or EBOV, preferably VP40 is selected from one or more EBOV subtypes selected from the group consisting of Zaire Ebola virus (ZEBOV), Sudan Ebola virus (SEBOV), Cote d'Ivoire Ebola virus (EBOV-Cdl, also called Tai Forest virus or TAFV), Reston Ebola virus (EBOV-Reston) and Bundibugyo Ebola virus (BEBOV). In a preferred embodiment, VP40 is selected from one or more of ZEBOV, SEBOV and MARV. In certain embodiments, the filovirus glycoprotein and the filovirus VP40 are selected from the same filovirus strain. In a further preferred embodiment, VP40 and/or the filovirus glycoprotein are selected from one or more of Zaire-Mayinga, Zaire-Kikwit, Zaire-Gabon, Cote d'Ivoire Ebola virus, Sudan-Boniface, Sudan-Maleo, Sudan-Gulu, Marburg-Ravn, Marburg-Ozolin, Marburg-Ratayczak, Marburg-Musoke and Marburg-Angola, more preferably selected from one or more of Zaire-Mayinga (VP40-ZEBOV-Mayinga), Sudan-Gulu (VP40-SEBOV-Gulu), Marburg-Musoke (VP40-MARV-Musoke) and Marburg-Angola (VP40-MARV-Angola). In a further embodiment, the MVA vector of any of the embodiments further comprises a filovirus nucleoprotein (NP), preferably wherein the filovirus nucleoprotein and the filovirus VP40 are derived from the same filovirus strain. In a further embodiment, VP40 comprises the nucleic sequence encoding VP40-ZEBOV-Mayinga or VP40-MARV-Musoke. In other embodiments, filovirus VP40 comprises the nucleotide sequence of SEQ ID NO:33. In a further embodiment, VP40 comprises a nucleic acid encoding the protein sequence of SEQ ID NO:34. In a further preferred embodiment, VP40 comprises the nucleotide sequence of SEQ ID NO:33 encoding the amino acid sequence of SEQ ID NO:34.

In a further preferred embodiment, the recombinant MVA/FPV vector comprises two heterologous nucleotide sequences encoding an antigenic determinant of a filovirus envelope glycoprotein and at least one heterologous nucleotide sequence encoding an antigenic determinant of a further filovirus protein. In certain embodiments, the first heterologous nucleotide sequence encoding an antigenic determinant of a filovirus envelope glycoprotein encodes a GP-MARV, and the second heterologous nucleotide sequence encoding an antigenic determinant of a filovirus envelope glycoprotein encodes a GP-EBOV. The recombinant MVA/FPV vector comprises, according to a further preferred embodiment of the present invention, three heterologous nucleotide sequences encoding an antigenic determinant of a filovirus envelope glycoprotein and at least one heterologous nucleotide sequence encoding an antigenic determinant of a further filovirus protein. Preferably, the first heterologous nucleotide sequence encoding an antigenic determinant of a filovirus envelope glycoprotein encodes a GP-MARV, the second heterologous nucleotide sequence encoding an antigenic determinant of a filovirus envelope glycoprotein encodes a GP-EBOV, and the third heterologous nucleotide sequence encoding an antigenic determinant of a filovirus envelope glycoprotein encodes a GP-EBOV derived from an EBOV strain or isolate different than the GP-EBOV encoded by the second heterologous nucleotide sequence. Accordingly, one heterologous nucleotide sequence encoding an antigenic determinant of a filovirus envelope glycoprotein may encode GP-SEBOV-Gulu and the other one GP-ZEBOV-Mayinga.

In another embodiment, the recombinant MVA/FPV vector comprises two heterologous nucleotide sequences encoding an antigenic determinant of a GP-EBOV from an EBOV strain or isolate and two heterologous nucleotide sequence encoding an antigenic determinant of a GP-MARV from an MARV strain or isolate, preferably the MARV strain is MARV-Angola and MARV-Musoke and the EBOV strain is ZEBOV and/or SEBOV, preferably ZEBOV-Mayinga and SEBOV-Gulu. Of course, the further nucleotide sequence encoding an antigenic determinant of a further filovirus protein may encode also filovirus proteins selected from the group consisting of nucleoprotein (NP), virion protein 35 (VP35), virion protein 40 (VP40), virion protein 30 (VP30), virion protein 24 (VP24), and RNA-directed RNA polymerase protein (L), as already mentioned above which may also be derived from the different strains as already indicated above.

The recombinant MVA/FPV vector according to a further preferred embodiment of the present invention comprises two heterologous nucleotide sequences encoding an antigenic determinant of a filovirus envelope glycoprotein of GP-MARV and GP-EBOV and a third heterologous nucleotide sequence encoding an antigenic determinant of VP40. Such VP40 can be any of the VP40 as described supra or infra. Accordingly one heterologous nucleotide sequence encoding an antigenic determinant of a filovirus envelope glycoprotein may encode GP-SEBOV-Gulu, the other one GP-ZEBOV-Mayinga and the third heterologous nucleotide sequence may encode an antigenic determinant of filovirus protein VP40-ZEBOV, VP40-SEBOV or VP40-MARV, preferably VP40-ZEBOV-Mayinga or VP40-MARV-Musoke.

In a further preferred embodiment, the recombinant MVA/FPV vector comprises two heterologous nucleotide sequences encoding an antigenic determinant of a filovirus envelope glycoprotein GP-EBOV, preferably GP-ZEBOV and/or GP-SEBOV, more preferably GP-ZEBOV-Mayinga and GP-SEBOV-Gulu, one filovirus envelope glycoprotein of GP-MARV, preferably GP-MARV-Musoke or GP-MARV-Angola and at least one filovirus nucleoprotein, preferably selected from the group of NP-EBOV-Cdl, NP-ZEBOV and NP-MARV, preferably NP-MARV-Musoke or NP-MARV-Angola.

Integration Sites into MVA/FPV

Heterologous nucleotide sequences encoding antigenic determinants of a filovirus glycoprotein, optionally further comprising at least one heterologous nucleotide sequence encoding a further filovirus protein may be inserted into one or more intergenic regions (IGR) of the MVA. In certain embodiments, the IGR is selected from IGR07/08, IGR 44/45, IGR 64/65, IGR 88/89, IGR 136/137, and IGR 148/149. In certain embodiments, less than 5, 4, 3, or 2 IGRs of the recombinant MVA comprise heterologous nucleotide sequences encoding antigenic determinants of a filovirus envelope glycoprotein and/or a further filovirus protein. The heterologous nucleotide sequences may, additionally or alternatively, be inserted into one or more of the naturally occurring deletion sites, in particular into the main deletion sites I, II, III, IV, V, or VI of the MVA genome. In certain embodiments, less than 5, 4, 3, or 2 of the naturally occurring deletion sites of the recombinant MVA comprise heterologous nucleotide sequences encoding antigenic determinants of a filovirus envelope glycoprotein and/or a further filovirus protein.

The number of insertion sites of MVA comprising heterologous nucleotide sequences encoding antigenic determinants of a filovirus protein can be 1, 2, 3, 4, 5, 6, 7, or more. In certain embodiments, the heterologous nucleotide sequences are inserted into 4, 3, 2, or fewer insertion sites. Preferably, two insertion sites are used. In certain embodiments, three insertion sites are used. Preferably, the recombinant MVA comprises at least 2, 3, 4, 5, 6, or 7 genes inserted into 2 or 3 insertion sites.

Heterologous nucleotide sequences encoding antigenic determinants of a filovirus glycoprotein, optionally further comprising at least one heterologous nucleotide sequence encoding a further filovirus protein may be inserted into one or more intergenic regions (IGR) of the FPV. In a preferred embodiment, the IGR is situated between ORFs 7 and 9 of the 1.3-kbp HindIII fragment of the genome (see Drillien et al, Virology 160:203-209 (1987) (U.S. Pat. No. 5,180,675) and Spehner et al, *J. Virol.* 64:527-533 (1990)). In certain embodiments, heterologous nucleotide sequences may be inserted in fowlpox insertion sites as described in EP 0 538 496 A1 and WO 05/048957 incorporated by reference herewith. Also preferred fowlpox insertion sites of the present invention are the LUS insertion site, the FP14 insertion site, and the 43K insertion site. These sites are also referred to sometimes as FPN006/FPN007 (LUS insertion site), FPN254/FPN255 (LUS insertion site), FPV060/FPV061 (FP14 insertion site), and FPV107/FPV108 (43K insertion site).

In one preferred embodiment, the insertion site in fowlpox is the LUS insertion site. There are two long unique sequences (LUS) at each end of the fowlpox viral genome (Genbank Accession NO: AF 198100.1), and thus two LUS insertion sites in each genome. The LUS insertion site at the left end of the genome lies 3' of FPV006 and 5' of FPV007 125L, preferably between position 7470 and 7475 in the fowlpox genomic sequence as annotated in GenBank Accession No. AF198100.1. The LUS insertion site at the right end of the genome lies 3' of FPV254 and 5' of FPV255, preferably between position 281065 and 281070 in the fowlpox genomic sequence e.g., of GenBank Accession No. AF198100.1. In one embodiment, the heterologous nucleotide sequence can be inserted at any position within the nucleotide position 281065 and 281070.

In another preferred embodiment, the insertion site in fowlpox is the FP14 insertion site. This site lies 3' of FPV060 and 5' of FPV061 in the fowlpox genomic sequence, preferably between position 67080 and 67097 of the fowlpox genome e.g., of GenBank Accession No. AF198100.1. In one embodiment, the nucleotides between position 67080 and 67097 of the DNA sequence are deleted in the recombinant virus and replaced with defined inserts representing a sequence of interest. In one embodiment, the FP14 insertion site is between the orthologue of the FPV060 gene and the orthologue of FPV061 e.g., of AF198100.1. The term “FPV060, FPV061, FPV254” etc. refers to the position of the corresponding coding sequence (i.e., CDS) of the respective gene numbered from 5' to 3' as annotated in GenBank Accession No. AF198100.1. In a preferred embodiment, the FP14 insertion site is between position 67091 and 67092 in the fowlpox genomic sequence (referred to also as IGR60/61 insertion site as annotated in GenBank Accession No. AF198100.1).

In yet another preferred embodiment, the insertion site in fowlpox is designated the 43K insertion site. This site lies 3' of FPV107 and 5' of FPV108, preferably at position 128178 of the fowlpox genomic sequence as annotated in GenBank Accession No. AF198100.1.

In a preferred embodiment, the integration site is FP14 (IGR60/61) and/or the BamHI J region. The BamH1 J region is further described in S. Jenkins et al. (1991), *Aids Research and Human Retroviruses* 7(12):991:998 incorporated by reference herewith.

In a certain embodiment, the IGR is IGR BamHI J FPV.

The number of insertion sites of the FPV comprising heterologous nucleotide sequences encoding antigenic determinants of a filovirus protein can be one or two. Preferably, two insertion sites are used. In another preferred embodiment, the recombinant FPV comprises at least 1, 2, 3, 4 or 5 genes inserted into one or two insertion sites.

The recombinant MVA/FPV viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) (J. Sambrook et al., Cold Spring Harbor Laboratory Press (1989)), and techniques for the handling and manipulation of viruses are described in Virology Methods Manual (B. W. J. Mahy et al. (eds.), Academic Press (1996)). Similarly, techniques and know-how for the handling, manipulation and genetic engineering of MVA are described in Molecular Virology: A Practical Approach (A. J. Davison & R. M. Elliott (Eds.), The Practical Approach Series, IRL Press at Oxford University Press, Oxford, UK (1993) (see, e.g., Chapter 9: Expression of genes by Vaccinia virus vectors)) and Current Protocols in Molecular Biology (John Wiley & Son, Inc. (1998) (see, e.g., Chapter 16, Section IV: Expression of proteins in mammalian cells using vaccinia viral vector)).

For the generation of the various recombinant MVAs/FPVs disclosed herein, different methods may be applicable. The DNA sequence to be inserted into the virus can be placed into an *E. coli* plasmid construct into which DNA homologous to a section of DNA of the MVA/FPV has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA/FPV DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate a MVA modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign or heterologous gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, coinfect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

Expression of Heterologous Filovirus Genes

A heterologous nucleotide sequence encoding an antigenic determinant of a filovirus protein can be expressed as a single transcriptional unit. For example, a heterologous nucleotide sequence encoding an antigenic determinant of a filovirus protein can be operably linked to a poxvirus e.g., vaccinia virus promoter and/or linked to a poxvirus e.g., vaccinia virus transcriptional terminator.

In certain embodiments, the "transcriptional unit" is inserted by itself into an insertion site in the MVA/FPV genome. In certain embodiments, the "transcriptional unit" is inserted with other transcriptional unit(s) into an insertion site in the MVA/FPV genome. The "transcriptional unit" is not naturally occurring (i.e., it is heterologous, exogenous or foreign) in the MVA/FPV genome and is capable of transcription in infected cells.

Preferably, the recombinant MVA/FPV comprises 1, 2, 3, 4, 5, or more transcriptional units inserted into the MVA/FPV genome. In certain embodiments, the recombinant MVA/FPV stably expresses heterologous nucleotide sequences encoding antigenic determinants of a filovirus protein encoded by 1, 2, 3, 4, 5, or more transcriptional units. In certain embodiments, the recombinant MVA/FPV comprises 2, 3, 4, 5, or more transcriptional units inserted into the MVA/FPV genome at 1, 2, 3, or more insertion sites in the MVA/FPV genome.

In certain embodiments, expression of one, more, or all of the heterologous nucleotide sequences encoding antigenic determinants of a filovirus protein is under the control of one or more poxvirus promoters. In certain embodiments, the poxvirus promoter is a Pr7.5 promoter, a hybrid early/late promoter, a PrS promoter, a PrS5E promoter, a synthetic or natural early or late promoter, or a cowpox virus ATI promoter. Suitable promoters are further described in WO 2010/060632, WO 2010/102822, WO 2013/189611 and WO 2014/063832 incorporated fully by reference herewith. In certain embodiments, the poxvirus promoter is selected from the group consisting of the PrS promoter (SEQ ID NO:23), the PrS5E promoter (SEQ ID NO:24), the Pr7.5 (SEQ ID NO:25), the PrLE1 promoter (SEQ ID NO:27), the Pr13.5 long promoter (SEQ ID NO:35) and the FPV-40K promoter (SEQ ID NO:26), more preferably selected from the group consisting of the PrS promoter (SEQ ID NO:23), the PrS5E promoter (SEQ ID NO:24), the Pr7.5 (SEQ ID NO:25) and the PrLE1 promoter (SEQ ID NO:27).

In certain embodiments, the nucleotide sequence encoding the antigenic determinant of the filovirus protein preferably the ZEBOV, SEBOV, EBOV-Cdl, MARV and NP-ZEBOV protein, more preferably the GP-ZEBOV-Mayinga, GP-SEBOV-Gulu, GP-MARV and NP-ZEBOV, most preferably the GP-MARV-Musoke or GP-MARV-Angola are under the control of the promoter selected from the group consisting of PrS, PrLE1 and Pr7.5. In a preferred embodiment, the nucleotide sequence encoding the antigenic determinant of the filovirus protein GP-SEBOV and GP-MARV-Musoke are expressed under the control of the PrS promoter (e.g., SEQ ID NO:23), NP-EBOV-Cdl is expressed under the control of the PrLE1 or modified PrLE1 promoter (e.g., SEQ ID NO:27 and SEQ ID NO:32), and GP-ZEBOV-Mayinga is expressed under the control of the Pr7.5 promoter (e.g., SEQ ID NO:25).

In another preferred embodiment, the nucleotide sequence encoding the antigenic determinant of the filovirus protein of the FPV of any of the embodiments is under the control of the promoter, preferably including or having SEQ ID NO:26.

Filovirus Vaccines and Pharmaceutical Compositions

Since the recombinant MVA viruses described herein are highly replication restricted and, thus, highly attenuated, they are ideal candidates for the treatment of a wide range of mammals including humans and even immune-compromised humans. Hence, provided herein are pharmaceutical compositions and vaccines for inducing an immune response in a living animal body, including a human. Additionally provided is a recombinant MVA vector comprising a nucleotide sequence encoding an antigenic determinant of a filovirus glycoprotein for use in the treatment and/or prevention of a filovirus-caused disease.

The vaccine preferably comprises any of the recombinant MVA viruses described herein formulated in solution in a concentration range of $10^4$ to $10^9$ $TCID_{50}$/ml, $10^5$ to $5\times10^8$ $TCID_{50}$/ml, $10^6$ to $10^8$ $TCID_{50}$/ml, or $10^7$ to $10^8$ $TCID_{50}$/ml. A preferred vaccination dose for humans comprises between $10^6$ to $10^9$ $TCID_{50}$, including a dose of $10^6$ $TCID_{50}$, $10^7$ $TCID_{50}$, or $10^8$ $TCID_{50}$.

The pharmaceutical compositions provided herein may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the recombinant MVA viruses provided herein can be converted into a physiologically acceptable form. This can be done based on experience in the preparation of poxvirus vaccines used for vaccination against smallpox as described by H. Stickl et al., *Dtsch. med. Wschr.* 99:2386-2392 (1974).

For example, purified viruses can be stored at −80° C. with a titer of $5\times10^8$ $TCID_{50}$/ml formulated in about 10 mM Tris, 140 mM NaCl pH 7.4. For the preparation of vaccine shots, e.g., $10^2$-$10^8$ or $10^2$-$10^9$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. The glass ampoule is then sealed and can be stored between 4° C. and room temperature for several months. However, as long as no need exists, the ampoule is stored preferably at temperatures below −20° C.

For vaccination or therapy, the lyophilisate can be dissolved in an aqueous solution, preferably physiological saline or Tris buffer, and administered either systemically or locally, i.e., parenteral, subcutaneous, intravenous, intramuscular, intranasal, or any other path of administration known to the skilled practitioner. The mode of administration, the dose and the number of administrations can be optimized by those skilled in the art in a known manner. However, most commonly a patient is vaccinated with a second shot about one month to six weeks after the first vaccination shot.

Combination Vaccines Using Homologous/Heterologous Prime-Boost Regimens

The Combination Vaccines and methods described herein may also be used as part of a homologous prime-boost regimen. In the homologous prime-boost, a first priming vaccination is given followed by one or more subsequent boosting vaccinations. The boosting vaccinations are configured to boost the immune response generated in the first vaccination by administration of the same recombinant poxvirus that was used in the first vaccination.

In one exemplary embodiment a homologous prime-boost regimen may be employed wherein a MVA viral vector as defined herein is administered in a first dosage. One or more subsequent administrations of a MVA viral vector as defined herein can be given to boost the immune response provided in the first administration. Preferably, the one or more antigenic determinants are the same or similar to those of the first administration.

The MVA and FPV recombinant viral vectors according to the present invention may also be used in heterologous prime-boost regimens in which one or more of the initial prime vaccinations are done with either the MVA or the FPV vector as defined herein and one or more subsequent boosting vaccinations are done with the poxviral vector not used in the prime vaccination, e.g., if a MVA vector defined herein is given in a prime boost, then subsequent boosting vaccinations would be FPV vectors and vice versa.

In a preferred embodiment the prime vaccination is done with the MVA vector and the boosting vaccination with the FPV. Accordingly, one aspect of the invention relates to a combination vaccine comprising:

a) a first composition comprising an immunologically effective amount of a MVA vector comprising a nucleic acid encoding an antigenic protein of at least one filovirus subtype, together with a pharmaceutically acceptable carrier; and
b) a second composition comprising an immunologically effective amount of a fowlpox vector comprising a nucleic acid encoding an antigenic protein of a first filovirus subtype, together with a pharmaceutically acceptable carrier;

wherein the first compositions is a priming composition and the second composition is a boosting composition, preferably wherein the boosting composition comprises two or more doses of the vector of the boosting composition.

Vaccines and Kits Comprising Recombinant MVA and FPV Viruses

Also provided herein are vaccines and kits comprising any one or more of the recombinant FPVs and/or MVAs described herein. The kit can comprise one or multiple containers or vials of the recombinant MVA or FPV, together with instructions for the administration of the recombinant MVA and FPV to a subject at risk of filovirus infection. In certain embodiments, the subject is a human. In certain embodiments, the instructions indicate that the recombinant MVA is administered to the subject in a single dose, or in multiple (i.e., 2, 3, 4, etc.) doses. In certain embodiments, the instructions indicate that the recombinant MVA or FPV virus is administered in a first (priming) and second (boosting) administration to naïve or non-naïve subjects. Preferably, a kit comprises at least two vials for prime/boost immunization comprising the recombinant MVAs as described herein for a first inoculation ("priming inoculation") in a first vial/container and for an at least second and/or third and/or further inoculation ("boosting inoculation") in a second and/or further vial/container.

In a preferred embodiment the vaccines and kits provided herein comprise a first composition which comprises a MVA vector comprising a nucleic acid encoding an antigenic protein of a second filovirus subtype, of a third filovirus subtype or at least four filovirus subtypes.

In a preferred embodiment, the vaccines and kits provided herein comprise a MVA vector in the first composition, which comprises a nucleic acid encoding an antigenic protein selected from the group consisting of SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In a further embodiment the vaccines and kits provided herein comprise a MVA vector in the first composition comprising a nucleic acid encoding an antigenic protein selected from the group having SEQ ID NO:2, SEQ ID NO:4, SEQ ID NO:6, SEQ ID NO:20, SEQ ID NO:29 and SEQ ID NO:31, preferably comprising a nucleic acid encoding an antigenic protein selected from the group having: SEQ ID NO:6, SEQ ID NO:20, SEQ ID NO:29 and SEQ ID NO:31.

In a further embodiment the vaccines and kits provided herein comprise a first composition which comprises a MVA vector comprising a nucleic acid encoding an antigenic protein of at least four filovirus subtypes, preferably wherein the four different filovirus subtypes are selected from the group having SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In a further preferred embodiment the vaccines and kits provided herein are for use in generating a protective immune response against at least one filovirus subtype, wherein the first composition is used for priming said immune response and the second composition is used for boosting said immune response or for use in generating a protective immune response against at least one filovirus subtype, wherein the second composition is used for priming said immune response and the first composition is used for boosting said immune response. In any of the vaccines and kits provided herein the boosting composition can comprise two or more doses of the vector of the boosting composition.

As discussed previously above, the present invention also relates to heterologous vaccination regimes using two different non-replicating viral vectors.

For heterologous vaccine programs, the present invention provides a combination vaccine and/or vaccination kit which comprises:

(a) a first composition comprising an immunologically effective amount of a MVA vector comprising a nucleic acid encoding antigenic proteins of at least two filovirus subtypes, together with a pharmaceutically acceptable carrier; and (b) a second composition comprising an immunologically effective amount of a fowlpox vector comprising a nucleic acid encoding an antigenic protein of a first filovirus subtype, together with a pharmaceutically acceptable carrier;

wherein one of the compositions is a priming composition and the other composition is a boosting composition.

The present invention also provides a combination vaccine and/or vaccination kit which comprises:

(a) a first composition comprising an immunologically effective amount of a MVA vector comprising a nucleic acid encoding antigenic proteins of at least two filovirus subtypes, together with a pharmaceutically acceptable carrier; and (b) a second composition comprising an immunologically effective amount of a MVA vector comprising a nucleic acid encoding an antigenic protein of a first filovirus subtype, together with a pharmaceutically acceptable carrier;

wherein one of the compositions is a priming composition and the other composition is a boosting composition.

In this embodiment, the combination vaccines and/or kit comprises at least two vials for prime/boost immunization comprising the recombinant MVAs/FPVs as described herein for a first inoculation ("priming inoculation") in a first vial/container and for an at least second and/or third and/or further inoculation ("boosting inoculation") in a second and/or further vial/container.

The combination vaccine and/or kit can comprise multiple containers or vials of the recombinant MVA/FPV, together with instructions for the administration of the recombinant MVA/FPV to a subject at risk of filovirus infection. In certain embodiments, the subject is a human. In certain embodiments, the instructions indicate that the recombinant MVA/FPV is administered to the subject in a single dose, or in multiple (i.e., 2, 3, 4, etc.) doses. In certain embodiments, the instructions indicate that the recombinant MVA/FPV virus is administered in a first (priming) and second (boosting) administration to naïve or non-naïve subjects.

The first and/or second composition or MVA and/or FPV of any combination vaccine, vaccination kit and/or any heterologous vaccine program of the invention can comprise any of the MVA and/or FPV vector described herein or as further defined under "Recombinant MVA and FPV" and any combination thereof.

In a preferred embodiment, the combination vaccines as provided herein comprise a first composition comprising a MVA vector comprising a nucleic acid encoding an antigenic protein of a second filovirus subtype, an antigenic determinant of a third filovirus subtype, an antigenic determinant of four filovirus subtypes or an antigenic determinant of at least four filovirus subtypes.

In another embodiment, the combination vaccines as provided herein comprise a filovirus subtype selected from an Ebola virus (EBOV) or a Marburg virus (MARV).

In another embodiment, the combination vaccines as provided herein comprises an antigenic determinant from one or more EBOV subtypes selected from the group consisting of Zaire Ebola virus (ZEBOV), Sudan Ebola virus (SEBOV), Cote d'Ivoire Ebola virus (EBOV-Cdl), Reston Ebola virus (EBOV-Reston) and Bundibugyo Ebola virus (BEBOV).

In another embodiment, the combination vaccines as provided herein comprise an antigenic determinant of the filovirus protein is selected from the group consisting of an envelope glycoprotein (GP), nucleoprotein (NP), virion protein 35 (VP35), virion protein 40 (VP40), virion protein 30 (VP30), virion protein 24 (VP24), and RNA-directed RNA polymerase protein (L).

In a further preferred embodiment, the combination vaccines as provided herein comprise a MVA vector in the first composition comprising a nucleic acid encoding an antigenic protein selected from the group consisting of SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In a further embodiment, the combination vaccines provided herein comprise a first composition which comprises a MVA vector comprising a nucleic acid encoding an antigenic protein of at least four filovirus subtypes, preferably wherein the four different filovirus subtypes are selected from the group having SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In a further preferred embodiment, the combination vaccines provided herein comprise a first composition which comprises a MVA vector comprising a nucleic acid encoding antigenic proteins from four different filovirus subtypes selected from the group having: SEQ ID NO:6, SEQ ID NO:20, SEQ ID NO:29 and SEQ ID NO:31.

In another embodiment, the combination vaccines provided herein are for use in generating a protective immune response against at least one filovirus subtype, preferably at least two, more preferably at least four filovirus subtype.

In another embodiment of the present invention, the present invention relates to a combination vaccine or the recombinant MVA of any of the embodiments for use as a medicament or vaccine for generating a protective immune response or for inducing an enhanced immune response against at least one filovirus subtype, at least two filovirus subtypes, at least three or at least four filovirus subtypes, wherein the MVA is capable of producing filovirus-like particles in the subject to be treated, preferably, wherein the MVA is producing filovirus-like particles in the subject to be treated.

Methods and Uses of Recombinant MVA/FPV Viruses

Also provided herein are methods and/or any of the recombinant MVAs/FPVs as described herein for use in a method of immunizing a subject animal or for affecting an immune response in a subject. Also covered are uses of the recombinant MVAs/FPVs described herein for the preparation of a medicament or pharmaceutical for the immunization of a subject animal, in particular for the preparation of a medicament or vaccine for treating and/or preventing a filovirus-caused disease in a subject. Provided are also recombinant MVA/FPV according to any embodiment herein for use in priming or boosting an immune response against a filovirus, preferably wherein the recombinant MVA and/or recombinant FPV is administered once, twice, three times or four times.

Further covered herein are vaccine combinations or recombinant MVA of any of the embodiments for use as a medicament or vaccine for inducing an enhanced immune response against a filovirus infection wherein the MVA is capable of producing filovirus-like particles in the subject to be treated, preferably, wherein the MVA is producing filovirus-like particles in the subject to be treated. Also covered are vaccine combinations or recombinant MVA of any of the embodiments for use as a medicament or vaccine for treating and/or preventing a filovirus disease, wherein the MVA is capable of producing filovirus-like particles in the subject to be treated, preferably, wherein the MVA is producing filovirus-like particles in the subject to be treated.

Accordingly, in one embodiment, the present invention provides a method of inducing an immune response against filovirus in a subject, the method comprising administering to the subject:

(a) a first composition comprising an immunologically effective amount of a MVA vector comprising a nucleic acid encoding antigenic proteins of at least two filovirus subtypes, together with a pharmaceutically acceptable carrier; and (b) a second composition comprising an immunologically effective amount of a fowlpox vector comprising a nucleic acid encoding an antigenic protein of a first filovirus subtype, together with a pharmaceutically acceptable carrier;

wherein one of the compositions is a priming composition and the other composition is a boosting composition.

In another embodiment, the invention provides a method of inducing an immune response against a filovirus in a subject, the method comprising administering to the subject:

(a) a first composition comprising an immunologically effective amount of a MVA vector comprising a nucleic acid encoding antigenic proteins of at least two filovirus subtypes, together with a pharmaceutically acceptable carrier; and (b) a second composition comprising an immunologically effective amount of a MVA vector comprising a nucleic acid encoding an antigenic protein of a first filovirus subtype, together with a pharmaceutically acceptable carrier;

wherein one of the compositions is a priming composition and the other composition is a boosting composition.

In another embodiment, the method of inducing an immune response against a filovirus, the uses of the recombinant MVAs/FPVs described herein for the preparation of a medicament for immunization of a subject animal, in particular for the preparation of a medicament or vaccine for treating and/or preventing a filovirus-caused disease in a subject or the combination vaccine of any of the embodiments for use of providing a protective immune response against a filovirus infection as provided herein comprises a first composition which comprises a MVA vector comprising a nucleic acid encoding an antigenic protein of a second filovirus subtype, of a third filovirus subtype or of at least four filovirus subtypes.

In another embodiment, the method of inducing an immune response against a filovirus, the uses of the recombinant MVAs/FPVs described herein for the preparation of a medicament for immunization of a subject animal, in particular for the preparation of a medicament or vaccine for treating and/or preventing a filovirus-caused disease in a subject or the combination vaccine of any of the embodiments for use of providing a protective immune response against a filovirus infection as provided herein comprise a MVA vector in the first composition which comprises a nucleic acid encoding an antigenic protein selected from the group consisting of SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In a further embodiment, the method of inducing an immune response against a filovirus, the uses of the recombinant MVAs/FPVs described herein for the preparation of a medicament for immunization of a subject animal, in particular for the preparation of a medicament or vaccine for treating and/or preventing a filovirus-caused disease in a subject or the combination vaccine of any of the embodiments for use of providing a protective immune response against a filovirus infection as provided herein comprises a first composition which comprises a MVA vector comprising a nucleic acid encoding an antigenic protein of at least four filovirus subtypes, preferably wherein the four different filovirus subtypes are selected from the group having SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In another embodiment, the present invention provides a method of providing protective immunity and/or a protective immune response against a filovirus infection in a subject. In another embodiment, the invention provides a method of providing protective immunity and/or a protective immune response against a filovirus infection in a subject:

(a) a first composition comprising an immunologically effective amount of a MVA vector comprising a nucleic acid encoding antigenic proteins of at least two filovirus subtypes, preferably at least three or at least four different filovirus subtypes, together with a pharmaceutically acceptable carrier; and (b) a second composition comprising an immunologically effective amount of a FPV vector comprising a nucleic acid encoding an antigenic protein of a first filovirus subtype, together with a pharmaceutically acceptable carrier;

wherein one of the compositions is a priming composition and the other composition is a boosting composition, preferably wherein the second composition is a boosting composition, preferably to be administered once, twice, three times or four times.

In another embodiment, the method of providing protective immunity and/or a protective immune response against a filovirus infection of any of the embodiments comprises a MVA vector in the first composition comprising a nucleic acid encoding an antigenic protein selected from the group consisting of SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In another embodiment, the method of providing protective immunity and/or a protective immune response against a filovirus infection of any of the embodiments comprises a MVA vector in the first composition comprising a nucleic acid encoding antigenic proteins from four different filovirus subtypes having SEQ ID NO:2, SEQ ID NO:4, SEQ ID NO:6, SEQ ID NO: 20, SEQ ID NO:29, SEQ ID NO:31, SEQ ID NO:34 and SEQ ID NO:37.

In another embodiment, the present invention provides a method for production of filovirus-like particles or a method of inducing an enhanced immune response against a filovirus in a subject, the method comprising production of filovirus-like particles in the subject of any of the embodiments, wherein the filovirus VP40 is selected from the group consisting of Zaire Ebola virus (ZEBOV), Sudan Ebola virus (SEBOV), Cote d'Ivoire Ebola virus (EBOV-Cdl), Reston Ebola virus (EBOV-Reston) and Bundibugyo Ebola virus (BEBOV), preferably wherein the filovirus VP40 is selected from one or more ZEBOV, SEBOV and MARV.

In another embodiment, the present invention provides a method for production of filovirus-like particles or a method of inducing an enhanced immune response against a filovirus in a subject, the method comprising production of filovirus-like particles in the subject of any of the embodiments, wherein the filovirus glycoprotein and the filovirus VP40 are selected from the same filovirus strain.

In another embodiment, the present invention provides a method for production of filovirus-like particles or a method of inducing an enhanced immune response against a filovirus in a subject, the method comprising production of filovirus-like particles in the subject of any of the embodiments, wherein the MVA vector further comprises a nucleic acid encoding a filovirus nucleoprotein (NP), preferably wherein the filovirus nucleoprotein and the filovirus VP40 are derived from the same filovirus strain.

In another embodiment, the filovirus strain of any of the above methods is selected from the group of Zaire-Mayinga, Zaire-Kikwit, Zaire-Gabon, Cote d'Ivoire Ebola virus, Sudan-Boniface, Sudan-Maleo, Sudan-Gulu, Marburg-Ravn, Marburg-Ozolin, Marburg-Ratayczak, Marburg-Musoke, Marburg-Angola, preferably Zaire-Mayinga or Cote d'Ivoire Ebola virus, preferably wherein the filovirus VP40 is selected from the group of Zaire-Mayinga or Marburg-Musoke, more preferably wherein the filovirus VP40 comprises a nucleic acid encoding the protein sequence of SEQ ID NO:34 or wherein the nucleic acid encoding the antigenic protein of the filovirus VP40 comprises SEQ ID NO:33.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent. In certain embodiments, the subject animal is a mammal. The mammal may be an adult cow, a calf, in particular a juvenile calf, a rat, rabbit, pig, mouse, but preferably a human, and the method comprises administering a dose of any one or more of the recombinant MVAs/FPVs provided herein to the subject.

In certain embodiments, the subject is a human. In certain embodiments, the subject is an adult. In certain embodiments, the adult is immune-compromised. In certain embodiments, the adult is over the age of 10, 15, 20, 25, 30, 25, 40, 45, 50, 55, 60, 65, 70, 75, 80, or 85 years. In certain embodiments, the subject's age is less than 5 years, less than 3 years, less than 2 years, less than 15 months, less than 12 months, less than 9 months, less than 6, or less than 3 months. In certain embodiments, the subject's age is from 0-3 months, 3-6 months, 6-9 months, 9-12 months, 1-2 years, or 2-5 years.

Any of the recombinant MVAs/FPVs provided herein may be administered to the subject at a dose of $10^6$ to $10^{10}$ $TCID_{50}$, preferably $10^8$ to $10^9$ $TCID_{50}$ as, e.g., at a dose of $10^6$ to $10^9$ $TCID_{50}$, $10^6$ to $5\times10^8$ $TCID_{50}$, $10^7$ to $10^8$ $TCID_{50}$, $5\times10^7$ $TCID_{50}$ to $5\times10^8$ $TCID_{50}$, $10^7$ $TCID_{50}$ or $10^8$ $TCID_{50}$. In a certain embodiment, the recombinant MVA/FPV vector is administered in an amount of $1\times10^8$ $TCID_{50}$ to $1\times10^{10}$ $TCID_{50}$. In another embodiment, the recombinant MVA/FPV is administered in an amount of $1\times10^8$ $TCID_{50}$ to $5\times10^9$, preferably in an amount of $5\times10^8$ $TCID_{50}$ to $6\times10^9$. In certain embodiments, any of the recombinant MVAs provided herein are administered to a human subject at a dose of $10^7$ $TCID_{50}$ or $10^8$ $TCID_{50}$ or $5\times10^8$ $TCID_{50}$. In certain embodiments, any of the recombinant FPVs provided herein is administered to a human subject at a dose of $5\times10^8$, $6.3\times10^8$ or $1\times10^9$ $TCID_{50}$.

In another embodiment, the recombinant MVAs provided herein are administered to a human subject at a dose lower than the recombinant FPVs. In certain embodiments, any of the recombinant MVAs/FPVs provided herein are administered to the subject at any of the doses provided herein prior to filovirus exposure as, e.g., 1, 2, 3, or 4 weeks or 1, 2, 3, 4, 5, 6, 7, 8, 9, 10, 11, or 12 months before filovirus exposure. In certain embodiments, any of the recombinant MVAs/FPVs provided herein is administered to the subject at any of the doses provided herein after filovirus exposure as, e.g., 1, 2, 3, 4, 5, 6, 7, 8, 9, 10, 11, 12, 13, 14, 15, 16, 17, 18, 19, 20, 21, 22, 23, or 24 hours or 1, 2, 3, 4, 5, 6, or 7 days after filovirus exposure.

In certain embodiments, the recombinant MVAs/FPVs provided herein are administered to the subject in a single dose, or in multiple (i.e., 2, 3, 4, etc.) doses. In certain embodiments, the recombinant MVAs/FPVs provided herein are administered in a first (priming) and second (boosting) administration. The first dose may comprise $10^7$ to $10^8$ $TCID_{50}$ of recombinant MVA/FPV virus and the second dose may comprise $10^7$ to $10^8$ $TCID_{50}$ of recombinant MVA/FPV virus.

Boosting compositions are generally administered once or multiple times weeks or months after administration of the priming composition, for example, about 1 or 2 weeks or 3 weeks, or 4 weeks, or 6 weeks, or 8 weeks, or 16 weeks, or 20 weeks, or 24 weeks, or 28 weeks, or 32 weeks or one to two years.

Preferably, the initial boosting inoculation is administered 1-12 weeks or 2-12 weeks after priming, more preferably 1, 2, 4 or 8 weeks after priming. In a preferred embodiment, the initial boosting inoculation is administered 4 or 8 weeks after priming. In additional preferred embodiments, the initial boosting is conducted at least 2 weeks or at least 4 weeks after priming. In still another preferred embodiment, the initial boosting is conducted 4-12 weeks or 4-8 weeks after priming.

The recombinant MVAs/FPVs provided herein can be administered systemically or locally. In certain embodiments, the recombinant MVAs/FPVs are administered parenterally, subcutaneously, intravenously, intramuscularly, or intranasally, in particular subcutaneously. Preferably, the recombinant MVAs/FPVs are administered intranasally. In other embodiments, the recombinant MVAs/FPVs are administered by any other path of administration known to the skilled practitioner. In a further preferred embodiment, the recombinant MVA/FPV is administered intramuscularly, preferably the recombinant MVA/FPV is administered intramuscularly in a volume ranging between about 100 μl to about 10 ml preferably containing concentrations of e.g., about $10^4$ to $10^{10}$ virus particles/ml. Preferably, the recombinant MVA/FPV vector is administered in a volume ranging between 0.25 and 1.0 ml. More preferably, the recombinant MVA/FPV vector is administered in a volume of about 0.5 ml.

Method for Producing a Recombinant MVA/FPV Vector

Further embodiments comprise a method for producing a recombinant MVA vector of any of the embodiments of the invention or the antigenic determinant expressed from the genome of said recombinant MVA vector, comprising the steps of (a) infecting a host cell with the recombinant MVA virus of any of the embodiments or transfecting the cell with the recombinant DNA of the recombinant MVA virus of any of the embodiments preferably with the addition of a helper virus for production of MVA virus particles,
(b) cultivating the infected or transfected cell, and
(c) isolating the MVA virus and/or the antigenic determinant from said cell.

In another embodiment, the invention relates to a recombinant MVA virus and/or an antigenic determinant obtained from the method for producing a recombinant vector.

Further embodiments comprise a method for producing a recombinant FPV vector of any of the embodiments of the invention or the antigenic determinant expressed from the genome of said recombinant FPV vector, comprising the steps of (a) infecting a host cell with the recombinant FPV virus of any of the embodiments or transfecting the cell with the recombinant DNA of the recombinant FPV virus of any of the embodiments preferably with the addition of a helper virus for production of FPV virus particles,
(b) cultivating the infected or transfected cell, and
(c) isolating the FPV virus and/or the antigenic determinant from said cell.

In another embodiment, the invention relates to a recombinant FPV virus and/or an antigenic determinant obtained from the method for producing a recombinant vector.

In another embodiment, the invention relates to a method of generating a recombinant MVA vector comprising the steps of:

(a) infecting a host cell with a MVA virus,
(b) transfecting the infected cell with a recombinant vector comprising at least one nucleotide sequence encoding an antigenic determinant of any of the proteins, said nucleic acid sequence further comprising a genomic MVA virus sequence capable of directing the integration of the at least one nucleotide sequence into the MVA virus genome, and
(c) identifying, isolating and optionally purifying the generated recombinant MVA virus.

In another embodiment, the invention relates to a method of generating a recombinant FPV vector comprising the steps of:

(a) infecting a host cell with an FPV virus,
(b) transfecting the infected cell with a recombinant vector comprising at least one nucleotide sequence encoding an antigenic determinant of any of the proteins, said nucleic acid sequence further comprising a genomic FPV virus sequence capable of directing the integration of the at least one nucleotide sequence into the FPV virus genome, and
(c) identifying, isolating and optionally purifying the generated recombinant FPV virus.

Other embodiments of the invention will be apparent to those skilled in the art from consideration of the specification and practice of the invention disclosed herein. It is intended that the specification and examples be considered as exemplary only, with a true scope and spirit of the invention being indicated by the appended claims.

EXAMPLES

The detailed examples which follow are intended to contribute to a better understanding of the present invention. However, the invention is not limited by the examples. Other embodiments of the invention will be apparent to those skilled in the art from consideration of the specification and practice of the invention disclosed herein.

Example 1: Construction of Recombinant MVA

The following sections describe construction of recombinant MVAs comprising one or more heterologous nucleic acids expressing an antigenic determinant of a filovirus envelop glycoprotein and/or a further filovirus protein. All other constructs described herein are made using similar methods.

Construction of MVA-mBN252B (PrS-GP-MARV-Musoke)

The full-length DNA sequence of the naturally-occurring GP-MARV-Musoke gene (Lake Victoria isolate) served as reference sequence for construction of MARV vaccine candidate MVA-mBN252B. A nucleotide sequence encoding full-length GP-MARV-Musoke was synthesized by Geneart AG (Regensburg, Germany) with codon usage optimized for expression in humans and to minimize or prevent internal homologous recombination events. Although the codon optimization changed the wild-type DNA sequence, the codon-optimized sequence encodes an amino acid sequence identical to the wild-type GP-MARV-Musoke (SEQ ID NO:6; NCBI accession number ABA87127.1). Expression of GP-MARV-Musoke is driven by the promoter PrS, a synthetic promoter designed from early and late elements of vaccinia virus promoters (SEQ ID NO:23; see also S. Chakrabarti et al., "Compact, Synthetic Vaccinia Virus Early/Late Promoter for Protein Expression", *BioTechniques* 23(6):1094-1097 (1997)). The codon-optimized GP-MARV-Musoke gene was inserted into the MVA-BN genome by standard methods (see below) using one of several customized recombination plasmids targeting different specific regions of the MVA-BN genome, including the deletion sites or the intergenic (non-coding) regions (IGR).

Figure 4A:
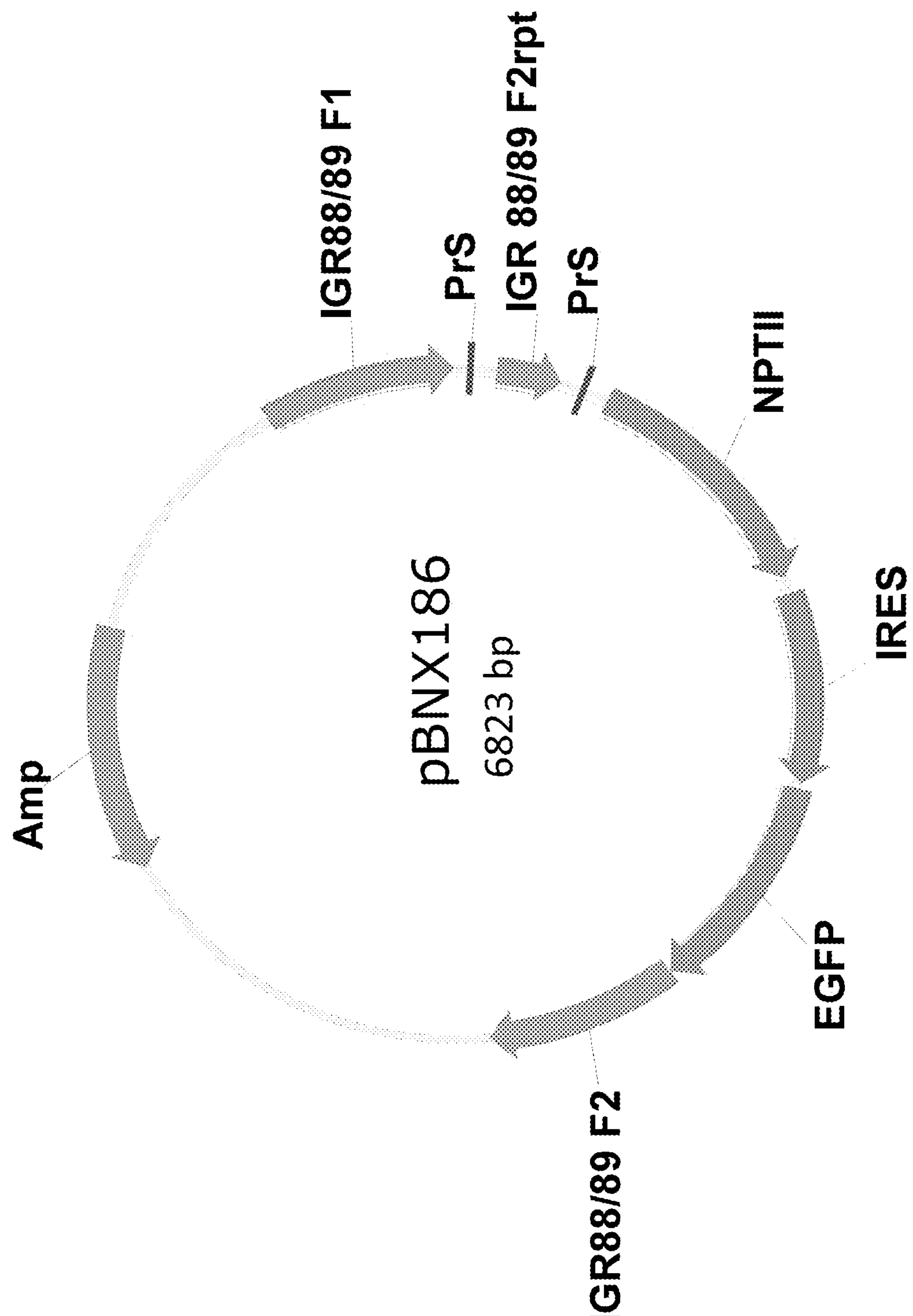
FIG. 4A shows the structure and genetic organization of plasmid pBNX186. Flank 1 (F1 IGR 88/89) and flank 2 (F2 IGR 88/89) are sequences of MVA-BN surrounding IGR 88/89. F1 IGR 88/89 and F2 IGR 88/89 are used for insertion of the expression cassette and the selection cassette (NPT II and eGFP) into MVA-BN in a homologous recombination event. The *E. coli* drug selection gene Neomycin Phosphotransferase (NPT II) and an enhanced Green Fluorescent Protein (eGFP) were connected via an internal ribosomal entry site (IRES) and inserted under the control of a strong synthetic poxvirus promoter (PrS) in order to allow selection for recombinant viruses. F2 and F2-repeat sequences of IGR 88/89 flank the selection cassette enabling the removal of the selection cassette via homologous recombination in the absence of selective pressure.
Figure 4B:
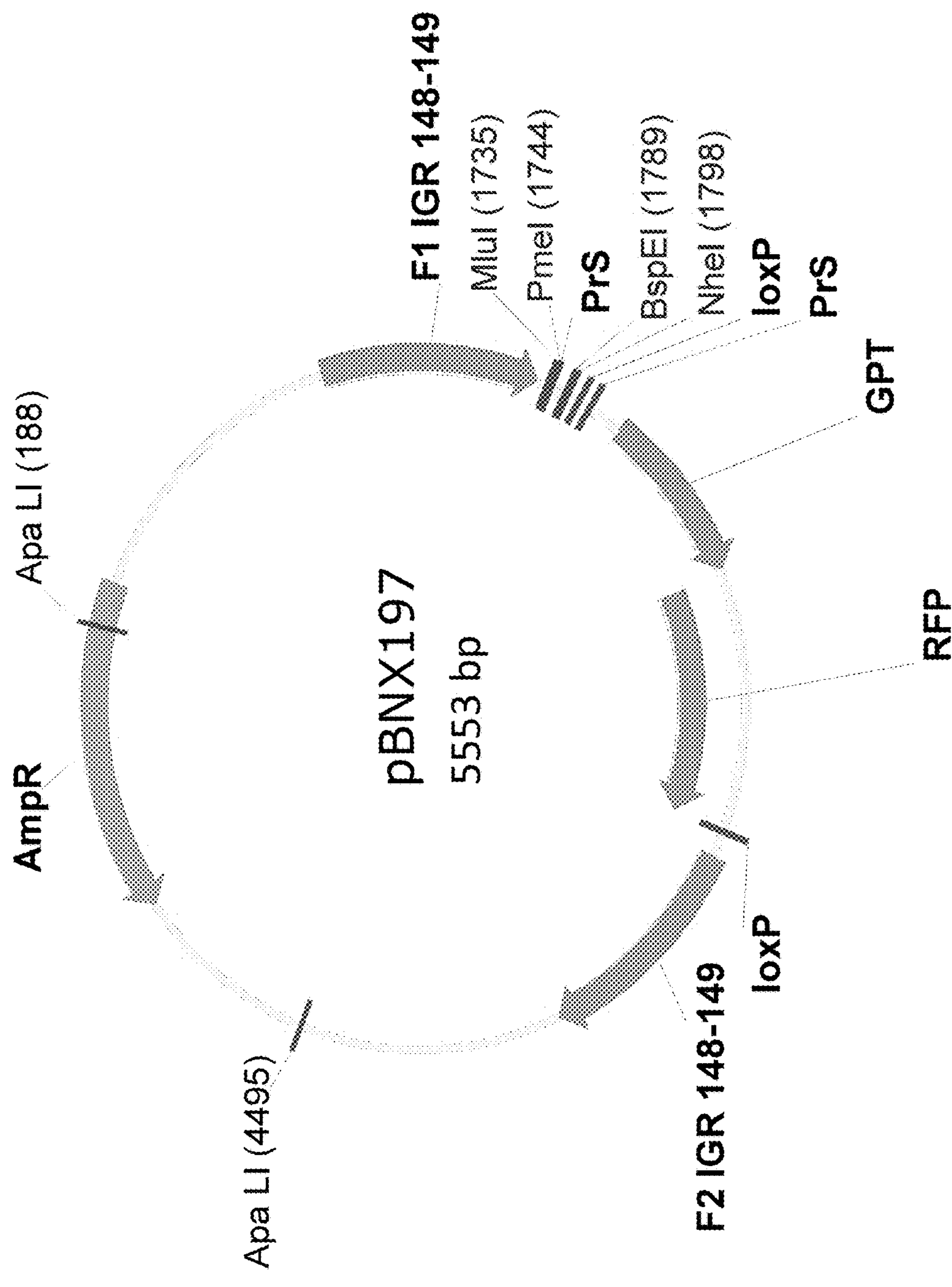
FIG. 4B shows the structure and genetic organization of plasmid pBNX197. Flank 1 (F1 IGR 148/149) and flank 2 (F2 IGR 148/149) are sequences of MVA-BN surrounding IGR 148/149. F1 IGR 148/149 and F2 IGR 148/149 are used for insertion of the expression cassette and the selection cassette (GPT and RFP) into MVA-BN in a homologous recombination event. The *E. coli* Guanine-Xanthine-Phosphoribosyl-Transferase drug selection gene (GPT) and a Red Fluorescence Protein gene (RFP) were inserted as a fusion gene under the control of a strong synthetic poxvirus promoter (PrS) in order to allow selection for recombinant viruses. LoxP sequences flank the selection cassette enabling the Cre recombinase-mediated removal of the selection cassette.
Figure 5A:
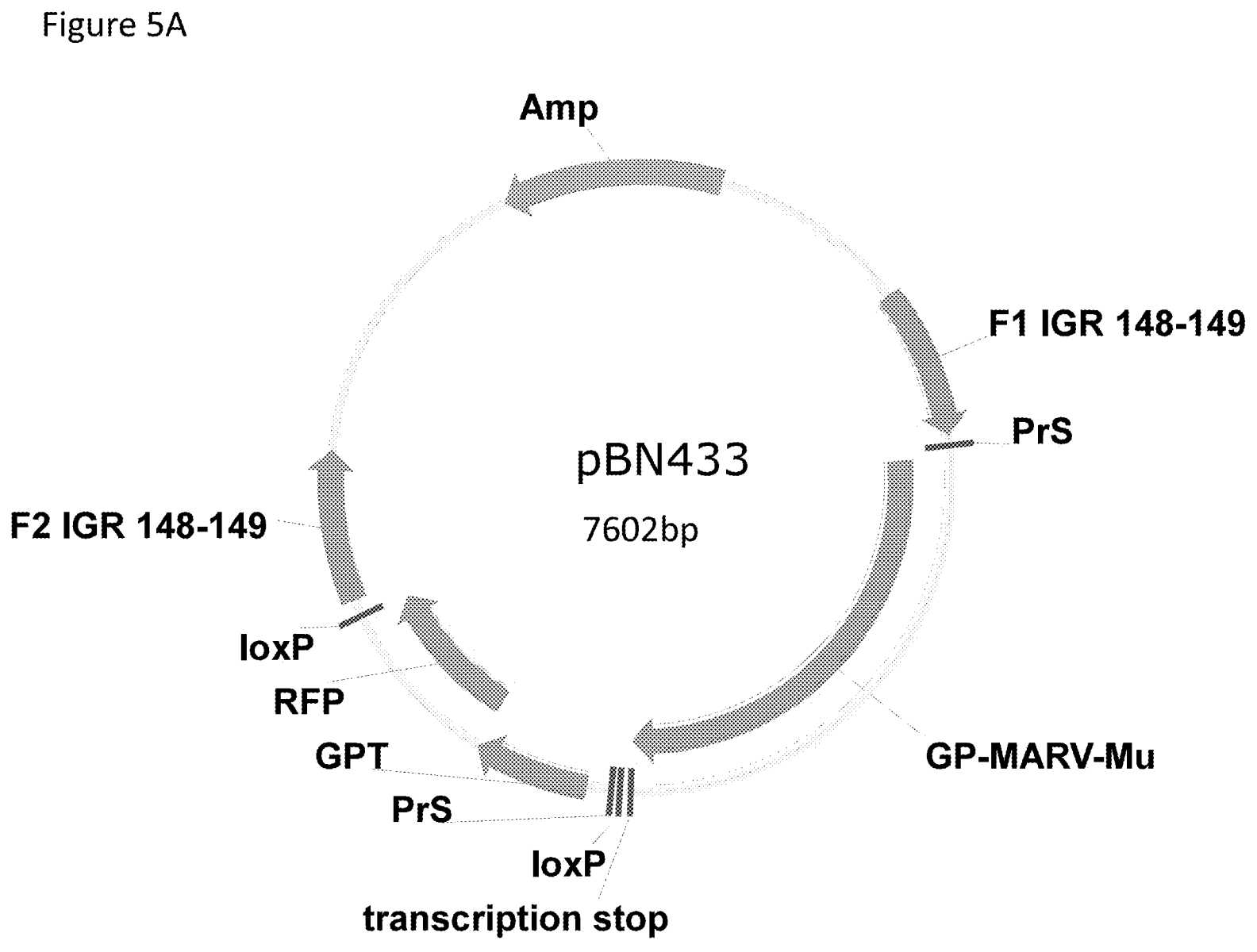

To insert the codon-optimized GP-MARV-Musoke gene into the MVA-BN genome, chicken embryonic fibroblast cells (CEF cells) were infected with MVA-BN and subsequently transfected with the recombination plasmid pBN433 (FIG. 5A). pBN433 contained the codon-optimized GP-MARV-Musoke gene (SEQ ID NO:5 (DNA) encoding SEQ ID NO:6 (amino acid)) under control of the synthetic PrS promoter inserted via BspEI/NheI restriction into plasmid pBNX197 (FIG. 4B). Plasmid pBN433 also contains MVA-BN DNA sequences flanking IGR 148/149 in the MVA-BN genome and a selection cassette flanked by loxP sites, which allows later elimination of the selection cassette by Cre recombinase-mediated recombination. Following homologous recombination between flanking sequences in the plasmid and homologous sequences at the desired insertion site in the MVA-BN genome (i.e., IGR 148/149), the coding portion of the plasmid was inserted into the desired site in the MVA-BN genome.

After amplification and plaque purification (nine passages; three of them including plaque purification) under selective conditions (mycophenolic acid/xanthine and hypoxanthine), the recombinant MVA-BN product designated MVA-mBN252A (PreMaster A), containing the gene for GP-MARV-Musoke was obtained. Recombinant MVA-mBN252A PreMaster virus stock was examined for elimination of MVA-BN (parental virus; data not shown), for correct sequence of the inserted gene together with the insertion flanking regions (by gene-specific PCR using primers specific for the MVA-BN genomic sequence into which the foreign gene was inserted; data not shown), for absence of microbes (sterility test; data not shown), and for the presence and correct size of the insert (by sequencing; data not shown). The titer of the MVA-mBN252A PreMaster virus stock was also determined.

Figure 4C:
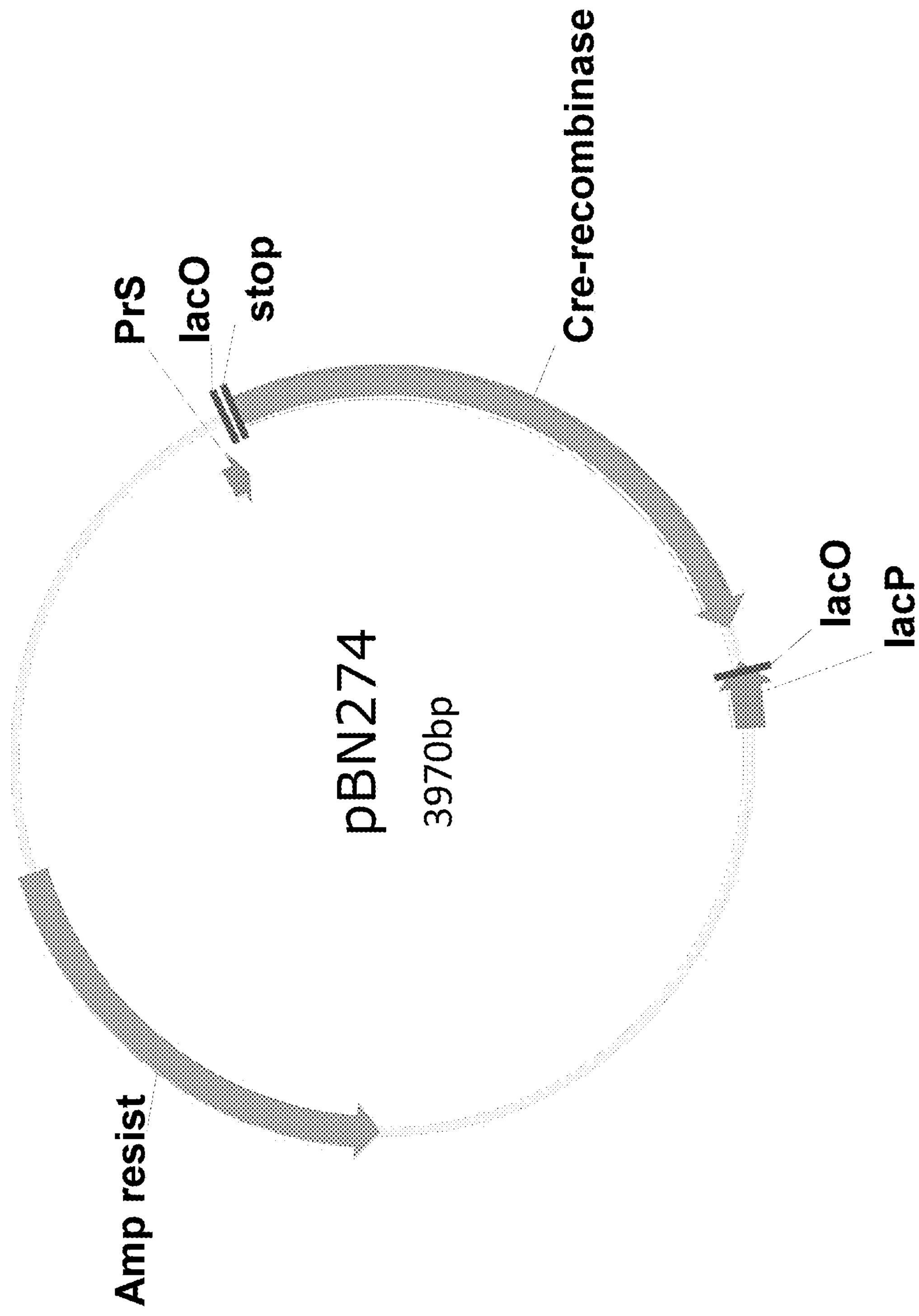
FIG. 4C shows the structure and genetic organization of plasmid pBN274, which expresses Cre recombinase.

The presence of a selection cassette in the inserted sequence permits positive selection for recombinant MVA-BN viruses in culture. To generate the final recombinant MVA-mBN252B, the selection cassette was removed from MVA-mBN252A PreMaster virus stock using the Cre/loxP system. To remove the selection cassette, CEF cells infected with recombinant MVA-BN containing the insert of plasmid pBN433 (i.e., GP-MARV-Musoke under the control of the PrS promoter, plus a selection cassette flanked by loxP sites) were further transfected with pBN274, an expression plasmid encoding the CRE recombinase (FIG. 4C). The site-specific Cre-recombinase catalyzed the precise excision of the selection cassette DNA sequences flanked by the target loxP sequence, completely removing the selection cassette. The resulting virus was plaque purified under non-selective conditions (twenty seven passages; nine of them including plaque purification), and the recombinant virus MVA-mBN252B devoid of selection cassette was isolated. Complete elimination of the selection cassette was confirmed by nested PCR (data not shown). Finally, expression of GP-MARV-Musoke by recombinant MVA-mBN252B was confirmed by reverse-transcriptase PCR (RT-PCR; data not shown).

Construction of MVA-mBN226B (Multi-Antigen MVA-Filo)

For all transgenes expressed from MVA-mBN226B, the full-length DNA sequences of the naturally-occurring genes served as reference sequences. Those were synthesized by Geneart AG (Regensburg, Germany) with codon usage optimized for expression in humans and to minimize or prevent internal homologous recombination events. The codon optimization changed the wild-type DNA sequence without altering the amino acid sequence. MVA-mBN226B contains the following filoviral genes: GP-SEBOV (SEQ ID NO:30); NP-EBOV-Cdl (SEQ ID NO:28); GP-ZEBOV, Mayinga strain (GP-ZEBOV-Mayinga, SEQ ID NO:19) and GP-MARV-Musoke (SEQ ID NO:5). GP-SEBOV and GP-MARV-Musoke are expressed under the control of the PrS promoter (SEQ ID NO:23), NP-EBOV-Cdl is expressed under the control of the PrLE1 or modified PrLE1 promoter (SEQ ID NO:27 and SEQ ID NO:32), and GP-ZEBOV-Mayinga is expressed under the control of the Pr7.5 promoter (SEQ ID NO:25).

The PrS promoter is a synthetic promoter designed from early and late elements of Vaccinia virus promoters, which ensures transgene expression during both the early and late phases of gene expression. Similarly, the Pr7.5 promoter from the vaccinia virus 7.5 kDa gene is a strong early and late promoter, meaning transgenes under its control will also be expressed during both the early and late phases of gene expression (SEQ ID NO:25; see also M. A. Cochran et al., "In vitro mutagenesis of the promoter region for a vaccinia virus gene: evidence for tandem early and late regulatory signals", *J. Virol.* 54(1):30-37 (1985)). The promoter PrLE1 is a synthetic promoter consisting of the A-type inclusion body promoter of cowpox virus (ATI) fused to five optimized early elements derived from Pr7.5 (SEQ ID NO:27; see also K. Baur et al., "Immediate-Early Expression of a Recombinant Antigen by Modified Vaccinia Virus Ankara Breaks the Immunodominance of Strong Vector-Specific B8R Antigen in Acute and Memory CD8 T-Cell Responses", *J. Virol.* 84(17):8743-8752 (2010)). Consequently, NP-EBOV-Cdl will be expressed during both the early and late phases of expression. Moreover, PrLE1 was shown to induce especially strong cell-mediated immune responses. During passaging of MVA-mBN226B, one of the five early elements derived from Pr7.5 was lost, likely by homologous recombination; analysis showed sufficient expression levels of NP-EBOV-Cdl, however (data not shown), so the modified construct was used without replacing the modified PrLE1 promoter.

Figure 5B:
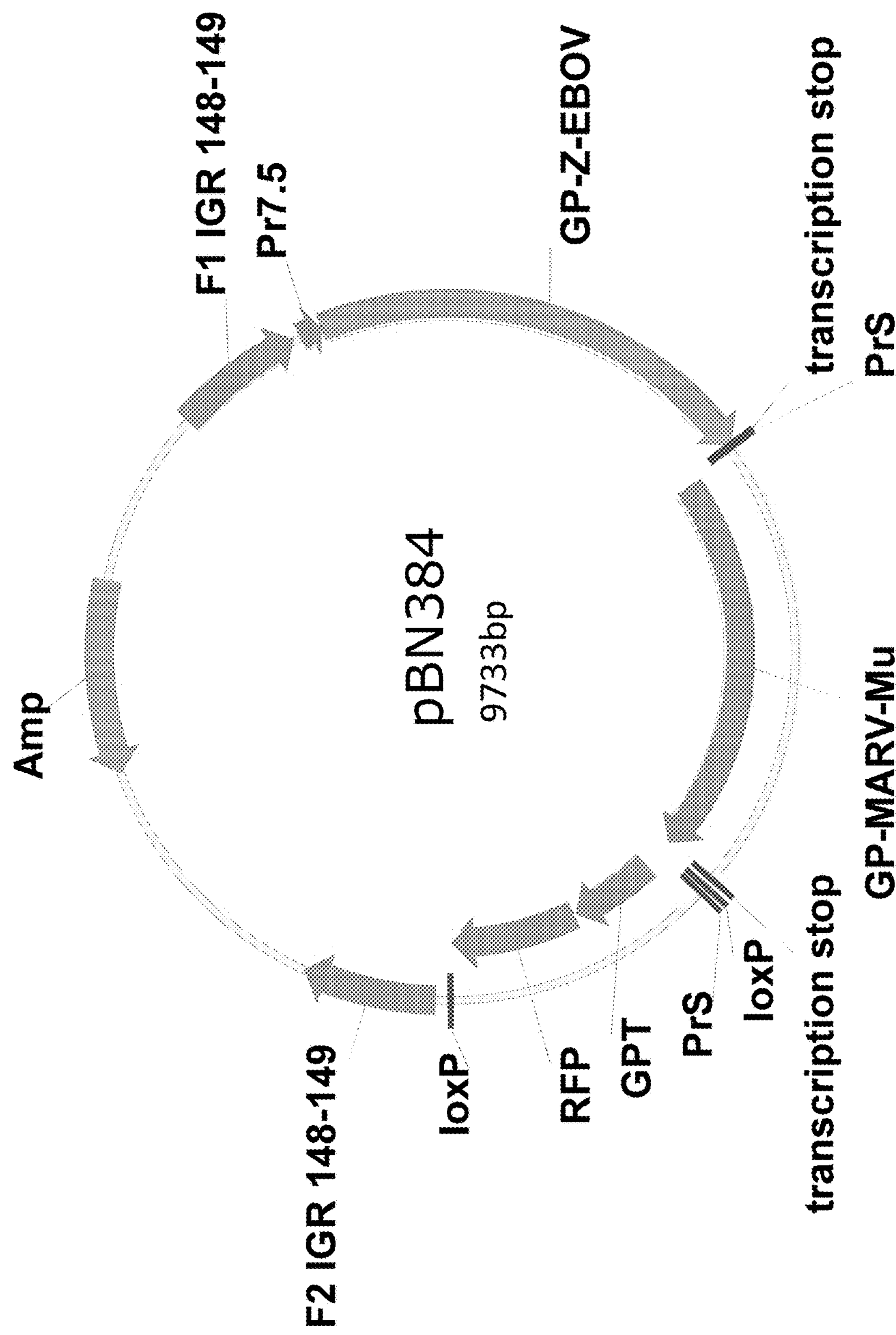
FIG. 5B shows the structure and genetic organization of plasmid pBN384. The glycoprotein genes of Ebola virus Zaire-Mayinga (GP-ZEBOV-Mayinga) and Marburg virus Musoke (GP-MARV-Musoke) were inserted under control of the promoters Pr7.5 and PrS into the MluI/NheI sites of pBNX197. In addition, the plasmid also contains MVA-BN DNA sequences flanking the IGR 148/149 of the MVA-BN genome and the loxP-flanked selection cassette. The loxP sites allow the later elimination of the selection cassette by CRE recombinase-mediated recombination.

For the insertion of foreign genes into the MVA-BN genome several recombination plasmids that target the different deletions and intergenic regions (IGR) of the MVA-BN genome were generated. To generate recombinant MVA-BN products, foreign sequences of interest can be inserted into any of these basic vectors, e.g., pBNX186 targeting IGR 88/89 (see FIG. 4A) or pBNX197 targeting IGR 148/149 (see FIG. 4B), using commonly available restriction enzymes and conventional molecular biology techniques. To produce recombinant MVA-BN isolates expressing the desired transgenes, CEF cells are then infected with MVA-BN and subsequently transfected with one or more recombination plasmids expressing the desired transgene or transgenes and including a selection cassette enabling positive selection for recombinant viruses. During homologous recombination, the plasmid flanking sequences recombine with the homologous sequences of the insertion site in the MVA-BN virus genome. This inserts the plasmid sequences into the site targeted by the basic vector used as starting material (e.g., IGR 148/149, IGR 88/89, etc.) in the MVA-BN genome. pBNX197 targets IGR 148/149 (FIG. 4B) and was used as starting plasmid for construction of the final recombination plasmid pBN384 (FIG. 5B). Plasmid pBN384 expresses GP-ZEBOV-Mayinga and GP-MARV-Musoke. pBNX 186 targets IGR 88/89 (FIG. 4A) and was used as starting plasmid for construction of the final recombination plasmid pBN385 (FIG. 5C). Plasmid pBN385 expresses GP-SEBOV and NP-EBOV-Cdl.

To insert the GP-SEBOV, NP-EBOV-Cdl, GP-ZEBOV-Mayinga, and GP-MARV-Musoke transgenes into MVA-BN, CEF cells were infected with MVA-BN and subsequently transfected with the recombination plasmids pBN384 and pBN385. After amplification and plaque purification (ten passages; three including plaque purification) under double selective conditions (mycophenolic acid/xanthine and hypoxanthine as well as Geneticin) the recombinant MVA-BN product designated MVA-mBN226A (Interim Premaster), containing the genes for three glycoproteins, one nucleoprotein and two selection cassettes, was obtained. Recombinant MVA-mBN226A PreMaster virus stock was examined for elimination of MVA-BN (parental virus; data not shown), for correct sequence of the inserted genes together with the insertion flanking regions (by gene-specific PCR using primers specific for the MVA-BN genomic sequences into which the foreign gene was inserted; data not shown), for absence of microbes (sterility test; data not shown), and for the presence and correct size of the inserts (by sequencing; data not shown). The titer of the MVA-mBN252A PreMaster virus stock was also determined.

After further amplification, removal of the selection cassettes and plaque purification under non-selective conditions (twenty passages; six including plaque purification) recombinant virus MVA-mBN226B devoid of selection cassettes was isolated. Complete elimination of the selection cassettes was confirmed by nested PCR (data not shown). Finally, transgene expression by recombinant MVA-mBN226B was confirmed by reverse-transcriptase PCR (RT-PCR; data not shown).

Construction of MVA-mBN254A (MVA-GP-ZEBOV)

For the GP-ZEBOV transgene expressed from MVA-mBN254A, the full-length DNA sequence of the naturally-occurring gene served as reference sequences. The GP-ZEBOV gene was synthesized by Geneart AG (Regensburg, Germany) with codon usage optimized for expression in humans and to minimize or prevent internal homologous recombination events as described above in "Construction of MVA-mBN226B". The codon optimization changed the wild-type DNA sequence without altering the amino acid sequence. GP-ZEBOV-Mayinga is expressed under the control of the PrS5E promoter (SEQ ID NO:24).

The PrS5E (SEQ ID NO:24) is a synthetic strong early and late promoter designed from the synthetic early and late promoter (Chakrabarti et al., 1997) followed by 5 early elements of the Pr7.5 promoter from the vaccinia virus 7.5 kDa gene (SEQ ID NO:25; see also M. A. Cochran et al., "In vitro mutagenesis of the promoter region for a vaccinia virus gene: evidence for tandem early and late regulatory signals", *J. Virol.* 54(1):30-37 (1985)). The PrS5E promoter is described in more detail in the patent application WO 2013/189611A1.

Figure 5D:
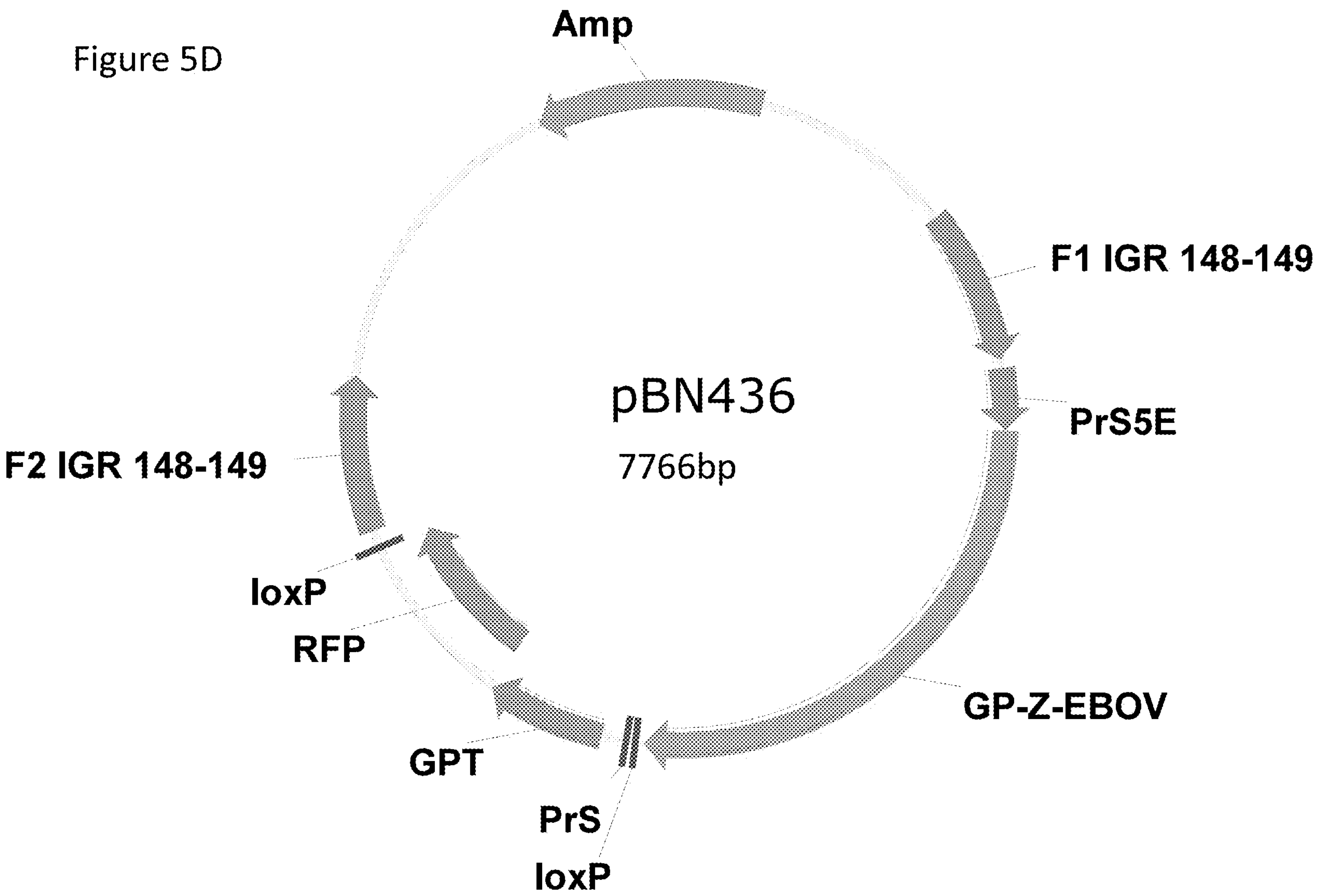
FIG. 5D shows the structure and genetic organization of plasmid pBN436. The glycoprotein gene of Ebola virus Zaire-Mayinga (GP-ZEBOV-Mayinga) was inserted into the BspEI/NotI sites of pBNX214 under control of the PrS5E promoter. In addition, the plasmid also contains MVA-BN DNA sequences flanking the IGR 148/149 of the MVA-BN genome and the loxP-flanked selection cassette. The loxP sites allow the later elimination of the selection cassette by Cre recombinase-mediated recombination.

For the insertion of foreign genes into the MVA-BN genome several recombination plasmids that target the different deletions and intergenic regions (IGR) of the MVA-BN genome were constructed. To generate recombinant MVA-BN products, foreign sequences of interest can be inserted into any of these basic vectors, e.g., pBNX197 targeting IGR 148/149 (see FIG. 4B), using commonly available restriction enzymes and conventional molecular biology techniques. To produce recombinant MVA-BN isolates expressing the desired transgenes, CEF cells are then infected with MVA-BN and subsequently transfected with one or more recombination plasmids expressing the desired transgene or transgenes and including a selection cassette enabling positive selection for recombinant viruses. During homologous recombination, the plasmid flanking sequences recombine with the homologous sequences of the insertion site in the MVA-BN virus genome. This inserts the target sequences into the site targeted by the basic vector used as starting material (e.g., IGR 148/149) in the MVA-BN genome. pBNX197 targets IGR 148/149 (FIG. 4B) and was used as starting plasmid for construction of the final recombination plasmid pBN436 (FIG. 5D). Plasmid pBN436 contains GP-ZEBOV-Mayinga.

Figure 3A:
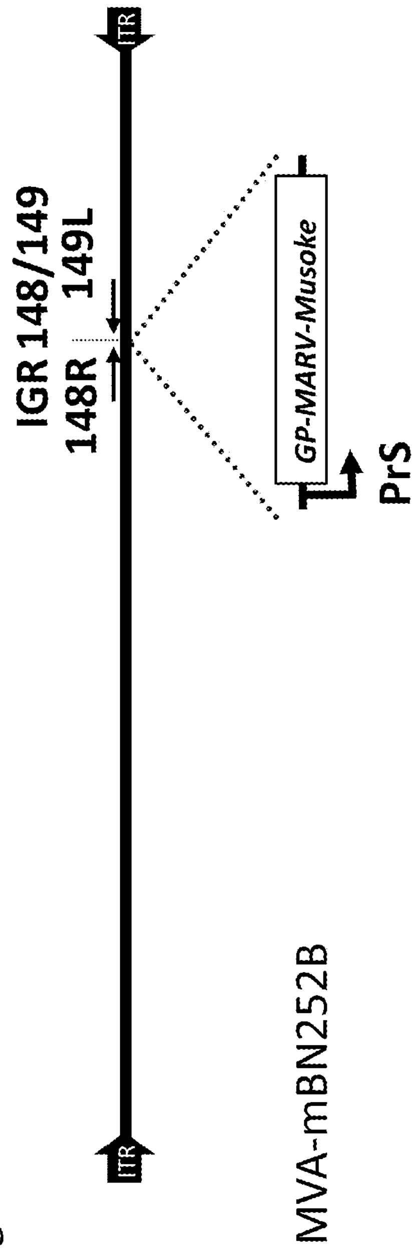
FIG. 3A shows the structure and genetic organization of MVA-mBN252B.
Figure 3B:
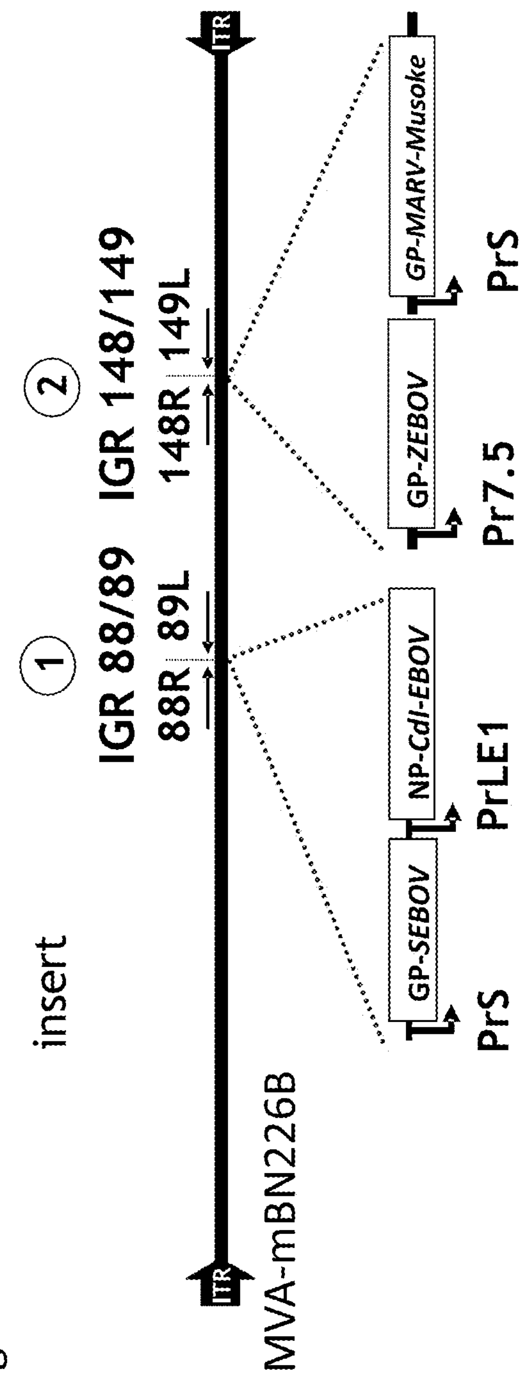
FIG. 3B shows the structure and genetic organization of MVA-mBN226B.

To insert the GP-ZEBOV-Mayinga transgene into MVA-BN, CEF cells were infected with MVA-BN and subsequently transfected with the recombination plasmid pBN436 (FIG. 5D). After amplification and plaque purification (nine passages; including three plaque purifications) under selective conditions (mycophenolic acid/xanthine and hypoxanthine) the recombinant MVA-BN product designated MVA-mBN254A (Premaster), containing the gene for GP-ZEBOV-Mayinga and the selection marker GPT-RFP fusion gene (FIG. 3C). Recombinant MVA-mBN254A PreMaster virus stock was examined for elimination of MVA-BN (parental virus; data not shown), for correct sequence of the inserted genes together with the insertion flanking regions (by gene-specific PCR using primers specific for the MVA-BN genomic sequences into which the foreign gene was inserted; data not shown), for absence of microbes (sterility test; data not shown), and for the presence and correct size of the inserts (by sequencing; data not shown). The titer of the MVA-mBN254A PreMaster virus stock was also determined. Finally, transgene expression by recombinant MVA-mBN254A was confirmed by reverse-transcriptase PCR (RT-PCR; data not shown).

Figure 13:
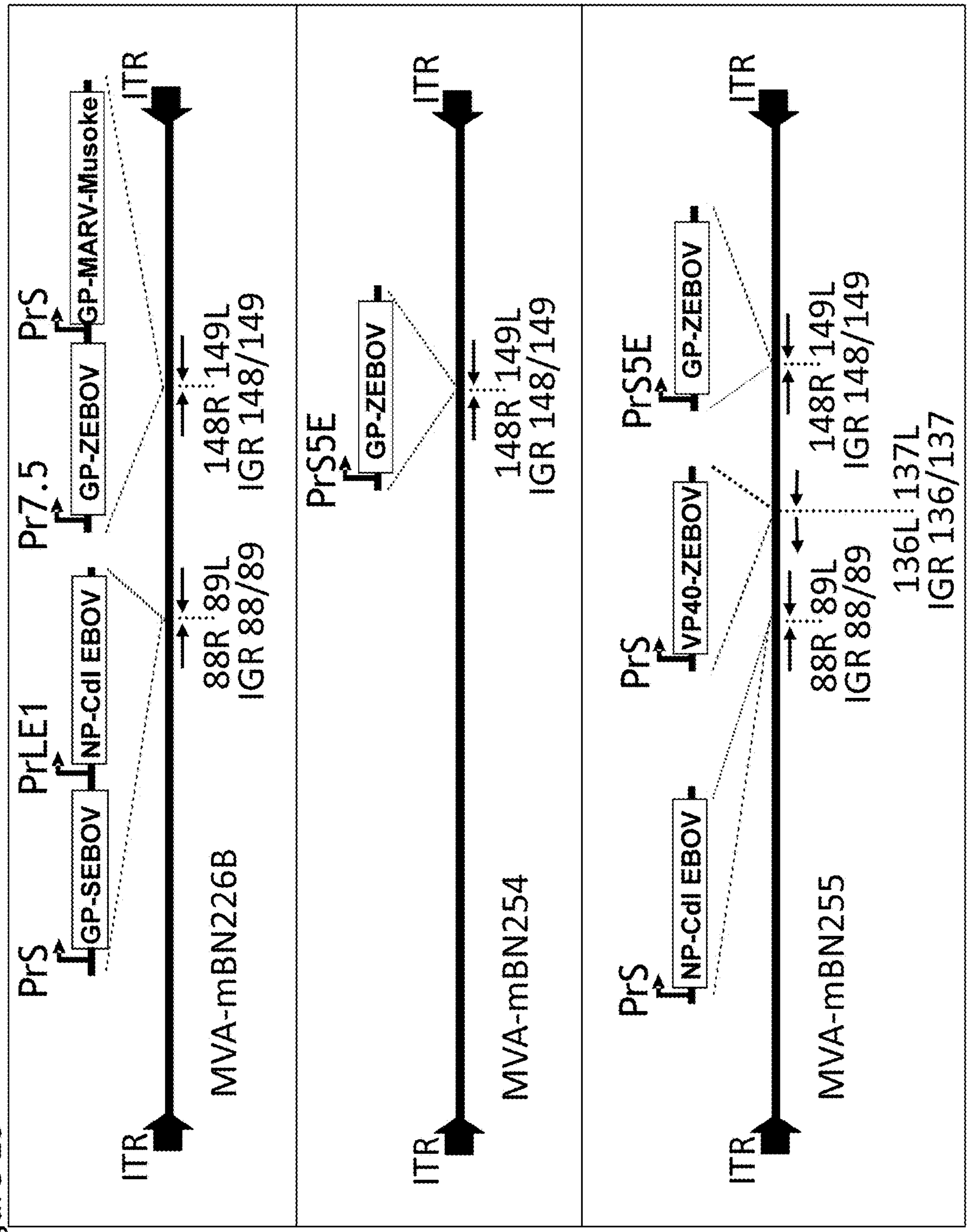
FIG. 13 shows the structure of certain recombinant MVA/FPV constructs.

Other constructs were generated accordingly. In particular, MVA-mBN255 expressed NP-EBOV-Cdl (SEQ ID NO:28) under the control of the PrS promoter integrated into the IGR 88/99, VP40 ZEBOV (SEQ ID NO:33) under control of the PrS promoter into the IGR 136/137 and GP-ZEBOV (SEQ ID NO:19) under control of the PrS5E promoter into the IGR 148/149 (FIG. 13).

Construction of FPV-mBN368A (FPV-GP-ZEBOV) and FPV-mBN391 (FPV-Multi-Filo)

For the GP-ZEBOV transgene expressed from FPV-mBN368A, the full-length DNA sequence of the naturally-occurring gene served as reference sequences. The GP-ZEBOV gene was synthesized by Geneart AG (Regensburg, Germany) with codon usage optimized for expression in humans as described in "Construction of MVA-mBN226B". The codon optimization changed the wild-type DNA sequence without altering the amino acid sequence. GP-ZEBOV-Mayinga is expressed under the control of the FPV-40K promoter (SEQ ID NO:26). The FPV-40K promoter is the FPV promoter sequence of the 40K protein coding sequence in FPV.

Figure 4D:
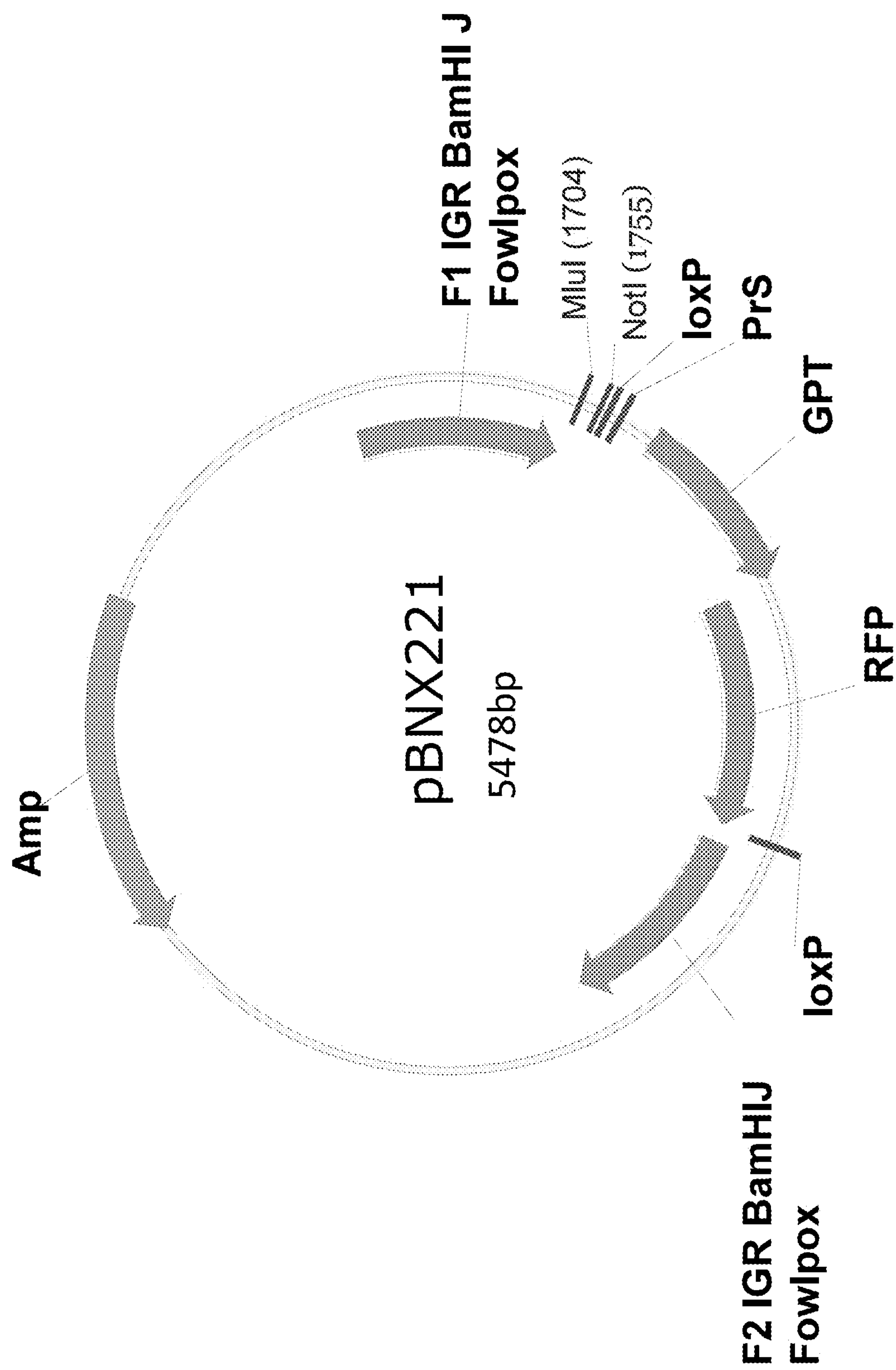
FIG. 4D shows the structure and genetic organization of plasmid pBNX221. Flank 1 (F1 IGR BamHI J FowlPox) and flank 2 (F2 IGR BamHIJ FowlPox) are sequences of FPV surrounding the insertion site BamHI J. F1 IGR BamHI J FowlPox and F2 IGR BamHI J FowlPox are used for insertion of the expression cassette and the selection cassette (GPT and RFP) into FPV in a homologous recombination event. The *E. coli* Guanine-Xanthine-Phosphoribosyl-Transferase drug selection gene (GPT) and a Red Fluorescence Protein gene (RFP) were inserted as a fusion gene under the control of a strong synthetic poxvirus promoter (PrS) in order to allow selection for recombinant viruses. LoxP sequences flank the selection cassette enabling the Cre recombinase-mediated removal of the selection cassette.
Figure 4E:
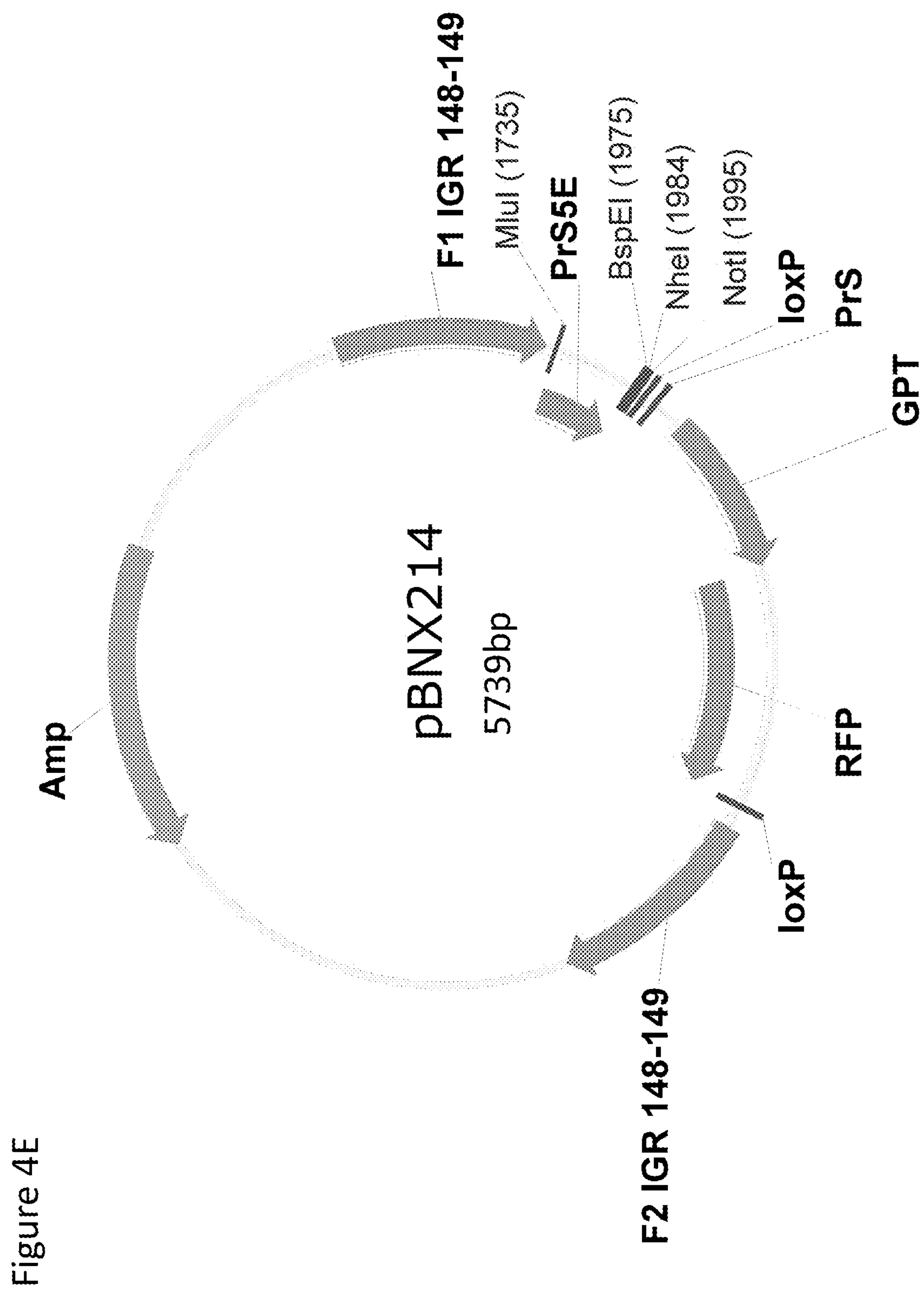
FIG. 4E shows the structure and genetic organization of plasmid pBNX214. Flank 1 (F1 IGR 148/149) and flank 2 (F2 IGR 148/149) are sequences of MVA-BN surrounding IGR 148/149. F1 IGR 148/149 and F2 IGR 148/149 are used for insertion of the expression cassette and the selection cassette (GPT and RFP) into MVA-BN in a homologous recombination event. pBNX214 already includes the PrS5E promoter for the expression of transgenes. The *E. coli* Guanine-Xanthine-Phosphoribosyl-Transferase drug selection gene (GPT) and a Red Fluorescence Protein gene (RFP) were inserted as a fusion gene under the control of a strong synthetic poxvirus promoter (PrS) in order to allow selection for recombinant viruses. LoxP sequences flank the selection cassette enabling the Cre recombinase-mediated removal of the selection cassette.
Figure 5E:
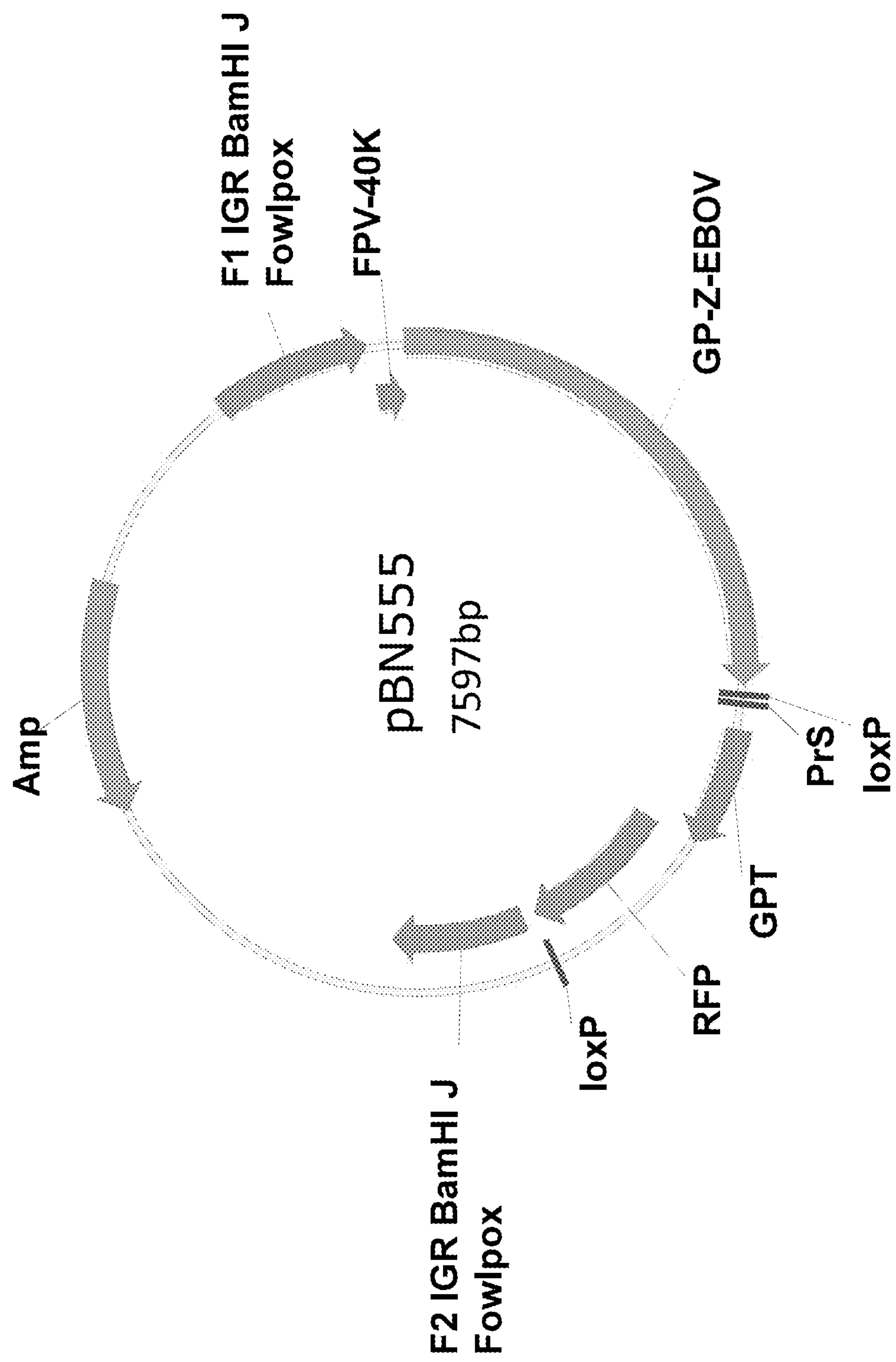
FIG. 5E shows the structure and genetic organization of plasmid pBN555. The glycoprotein gene of Ebola virus Zaire-Mayinga (GP-ZEBOV-Mayinga) under control of the FPV-40K promoter was inserted into the MluI/NotI sites of pBNX221. In addition, the plasmid also contains FPV DNA sequences flanking the Insertion site BamHI J of the FPV genome and the loxP-flanked selection cassette. The loxP sites allow the later elimination of the selection cassette by Cre recombinase-mediated recombination.

For the insertion of foreign genes into the FPV genome, several recombination plasmids that target the different integration sites into the FPV genome were constructed. To generate recombinant FPV products, foreign sequences of interest can be inserted into any of these basic vectors, e.g., pBNX221 targeting insertion site BamHI J (see FIG. 4D), using commonly available restriction enzymes and conventional molecular biology techniques. To produce recombinant FPV isolates expressing the desired transgenes, CEF cells are then infected with FPV and subsequently transfected with one or more recombination plasmids expressing the desired transgene or transgenes and including a selection cassette enabling positive selection for recombinant viruses. During homologous recombination, the plasmid flanking sequences recombine with the homologous sequences of the insertion site in the FPV virus genome. This inserts the target sequences into the site targeted by the basic vector used as starting material (e.g., insertion site BamHI J) in the FPV genome. pBNX221 targets insertion site BamHI J (FIG. 4D) and was used as starting plasmid for construction of the final recombination plasmid pBN555 (FIG. 5E). Plasmid pBN555 contains GP-ZEBOV-Mayinga under control of the FPV-40K promoter.

To insert the GP-ZEBOV-Mayinga transgene into FPV, CEF cells were infected with FPV and subsequently transfected with the recombination plasmid pBN555 (FIG. 5E). After amplification and plaque purification (13 passages; including four plaque purifications) under selective conditions (mycophenolic acid/xanthine and hypoxanthine) the recombinant MVA-BN product designated FPV-mBN368A (Premaster), containing the gene for GP-ZEBOV-Mayinga and the selection marker GPT-RFP fusion gene (FIG. 3D), was obtained. Recombinant FPV-mBN368A PreMaster virus stock was examined for elimination of FPV (parental virus; data not shown), for correct sequence of the inserted genes together with the insertion flanking regions (by gene-specific PCR using primers specific for the FPV genomic flanking sequences into which the foreign gene was inserted; data not shown), for absence of microbes (sterility test; data not shown), and for the presence and correct size of the inserts (by sequencing; data not shown). The titer of the FPV-mBN368A PreMaster virus stock was also determined. Finally, transgene expression by recombinant FPV-mBN368A was confirmed by reverse-transcriptase PCR (RT-PCR; data not shown).

Further fowlpox constructs were generated using FP14 (IGR 60/61) and the BamHI J region for integration according to the method as described above. FPV-mBN391 expressed GP-ZEBOV (SEQ ID NO:19 and 20) under the control of the FPV-40K promoter (SEQ ID NO:26), GP-MARV-Musoke (SEQ ID NO:5 and 6) under the PrS promoter (SEQ ID NO:23) both at the FP14 site and GP-MARV-Angola (SEQ ID NO:36 and 37) under the Pr13.5 long promoter (SEQ ID NO:35), GP-SEBOV (SEQ ID NO:30 and 31) under the FPV-40K promoter and NP-EBOV-Cdl (SEQ ID NO:28 and 29) under the control of the PrLE1 promoter (SEQ ID NO:27), all three inserted at the BamHI J region in the order mentioned.

Example 2: MVA-BN-Filo (MVA-mBN226B) in Non-Human Primates

Immunogenicity and protective efficacy of MVA-BN-Filo (MVA-mBN226B) was analyzed in an Ebola and Marburg challenge model in cynomolgus macaques. Monkeys were housed and fed in accord with the appropriate institutional guidelines for care and feeding of research animals.

The experimental design is set forth in Table 1 below.

TABLE 1

Vaccination protocol for MVA-BN-Filo in cynomolgus macaques.

| | | Test/Reference Item Administration | | | | Challenge Virus Administration | |
|---|---|---|---|---|---|---|---|
| Group | Group Size | Vaccination | Dose per Admin. | Route | Schedule (Days) | Virus | Schedule (Day) |
| 1 | 1 | Vehicle Control (TBS) | — | s.c. | 0 and 28 | EBOV | 42 |
| 2 | 1 | Vehicle Control (TBS) | — | s.c. | 0 and 28 | MARV | 42 |
| 3 | 3 | MVA-BN ®-Filo | $5 \times 10^8$ $TCID_{50}$ | s.c. | 0 and 28 | EBOV | 42 |
| 4 | 3 | MVA-BN ®-Filo | $5 \times 10^8$ $TCID_{50}$ | s.c. | 0 and 28 | MARV | 42 |

Intramuscular challenge (1,000 pfu) with either EBOV Zaire strain or MARV Musoke strain; surviving animals were euthanized on Day 63

Dose volume was 0.5 mL for both vehicle control and vaccination groups; all vaccinations were delivered by subcutaneous injection. First vaccination day is designated Day 0. All animals received a challenge dose of 1,000 pfu of ZEBOV (Groups 1 and 3) or MARV-Musoke (Groups 2 and 4) via intramuscular injection on Day 42. All surviving animals were euthanized on Day 63.

Figure 6:
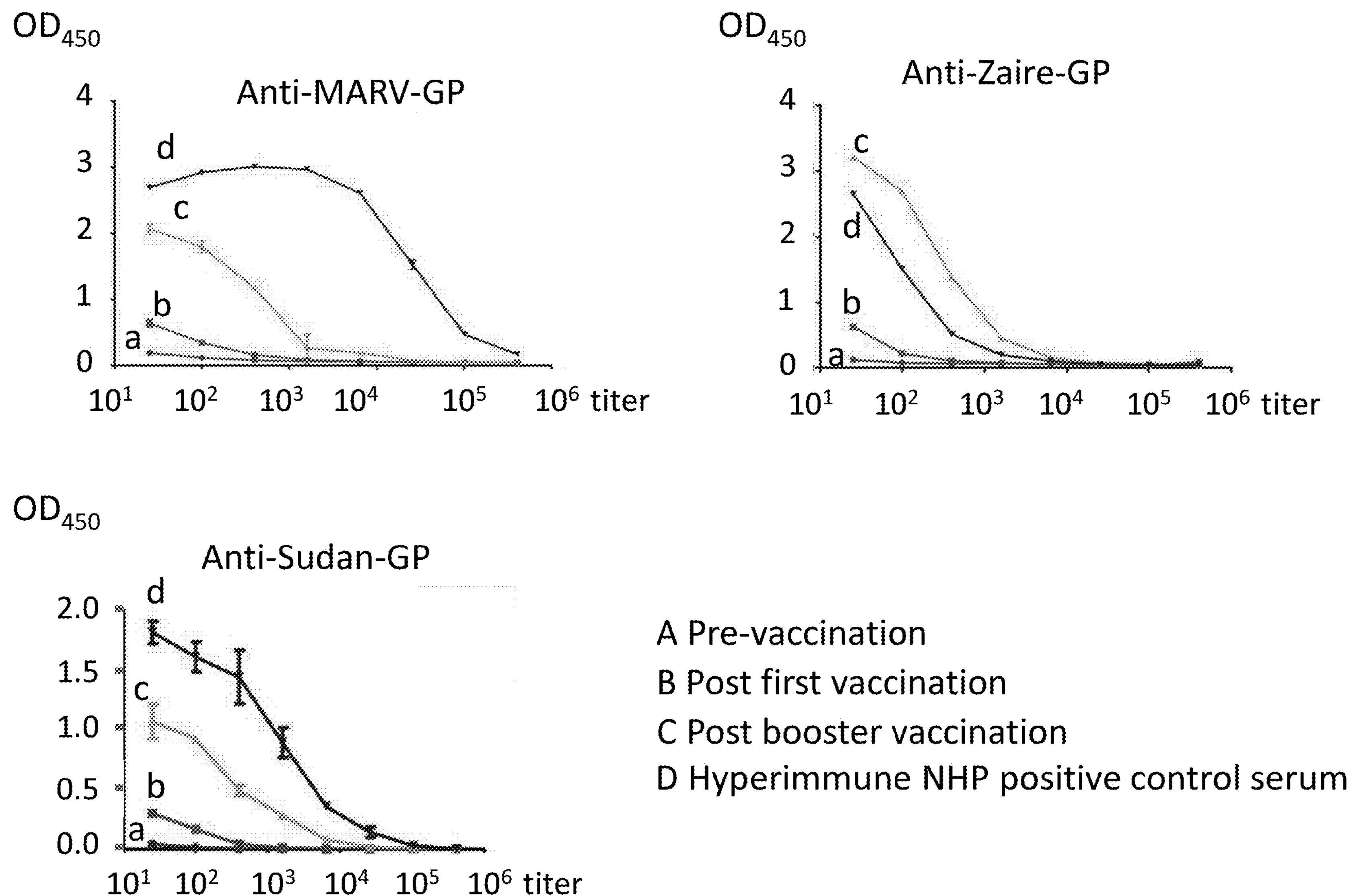
FIG. 6 shows the levels of antibodies against GP in cynomolgus macaques following vaccination with MVA-BN-Filo (MVA-mBN226B) as measured by ELISA. Animals were vaccinated twice four weeks apart with MVA-BN-Filo (on Day −42 and Day −14), and blood was drawn at intervals for analysis via ELISA: prior to vaccination (Day −42, red curve (1)), after the first but prior to the second vaccination (Day −14, green curve (2)), and after the second vaccination (Day −5, orange curve (3)). The graph on the left shows Marburg GP specific antibodies in serum, the graph in the middle shows Ebola Zaire GP specific antibodies in serum, and the graph on the right shows Ebola Sudan GP specific antibodies in serum. Hyperimmune serum from cynomolgus macaques immunized with either Marburg Angola GP (left graph), Ebola Zaire GP (middle graph), or Ebola Sudan GP (right graph) was used as positive control in each ELISA.

GP-specific antibodies were measured by ELISA. As expected, the non-vaccinated control animal challenged with MARV-Musoke had no detectable GP-MARV-specific antibodies at any time prior to challenge (i.e., on Day 0, Day 28, and Day 36 (data not shown) and succumbed to disease. In contrast, two of the three animals vaccinated with MVA-BN-Filo (animal numbers 30766 and 30768) had low GP-MARV antibody titers 28 days after the first vaccination (post first vaccination; see also FIG. 6) and all three vaccinated animals showed a clear boost response eight days after the second vaccination (post booster vaccination; see FIG. 6). All three animals survived the otherwise lethal intramuscular challenge with MARV-Musoke.

Similarly, the non-vaccinated control animal challenged with ZEBOV was negative for GP-ZEBOV-specific antibodies at all time-points tested (data not shown). The control animal, as well as all vaccinated animals succumbed to infection following challenge with ZEBOV by intramuscular injection. Surprisingly, all three vaccinated animals generated GP-ZEBOV-specific antibodies prior to challenge, at levels greater in magnitude than those measured in hyperimmune serum generated in non-human primates by vaccination with ZEBOV-GP. Complete necropsies were performed on tissue collected in 10% neutral buffered formalin at the time of death. Tissue sections were processed by routine methods, sectioned at 5 μm, and stained with hematoxylin and eosin for histological evaluation. Findings are summarized in Table 2 below.

TABLE 2

Histological evaluation of vaccinated and control animals.

| Animal # | 30763 | 30766 | 30765 | 30768 | 30764 | 30770 | 30769 | 30767 |
|---|---|---|---|---|---|---|---|---|
| Necropsy # | N11-05 | N11-04 | N11-06 | N11-10 | N11-07 | N11-08 | N11-09 | N11-03 |
| Challenge | Marburg | Marburg | Marburg | Marburg | Ebola | Ebola | Ebola | Ebola |
| Experimental group | control | vaccine | vaccine | vaccine | control | control | control | control |
| Survival | 9 d€ | 21 d | 21 d | 21 d | 5 d (E) | 7 d (SD) | 6 d (E) | 6 d(E) |
| Liver: | | | | | | | | |
| multifocal hepatic necrosis | ++ | − | − | − | + | ++ | ++ | − |
| vasculitis | + | ++* | − | ++* | − | − | − | − |
| Lung: | | | | | | | | |
| intra alveolar edema | + | − | − | − | + | + | + | − |
| septal edema | + | − | − | − | + | + | + | − |

TABLE 2-continued

Histological evaluation of vaccinated and control animals.

| Animal # | 30763 | 30766 | 30765 | 30768 | 30764 | 30770 | 30769 | 30767 |
|---|---|---|---|---|---|---|---|---|
| hemorrhage | + | − | − | − | + | + | − | − |
| interstitial pneumonitis | − | − | − | − | − | +++ | ++ | − |
| Spleen: | | | | | | | | |
| hyperplasia | − | ++ | +++ | +++ | − | − | − | − |
| lymphoid depletion | ++ | − | − | − | ++ | +++ | +++ | ++ |
| fibrin deposition red pulp | +++ | − | − | − | ++ | +++ | + | ++ |
| Splenic vasculitis | +++ | − | − | − | ++ | ++ | + | ++ |
| Inguinal lymph node: | | | | | | | | |
| macrophage infiltration | ++ | − | ++ | − | + | + | + | +++ |
| lymphoid depletion | +++ | − | − | − | +++ | +++ | ++ | − |
| Axillary lymph node: | | | | | | | | |
| Macrophage infiltration | − | − | − | − | − | − | − | − |
| lymphoid depletion | + | − | − | − | ++ | ++ | ++ | + |
| Mesenteric lymph node: | | | | | | | | |
| Macrophage infiltration | − | − | − | − | − | − | − | − |
| lymphoid depletion | ++ | − | − | − | ++ | ++ | ++ | + |
| Adrenal gland: | | | | | | | | |
| necrosis | − | − | − | − | +++ | ++ | − | − |

*vasculitis in animals 30766 and 30768 appears to be a pre-existing condition.
E—euthanized;
SD—spontaneous death Analysis confirmed typical symptoms of hemorrhagic fever in the MARV-Musoke-challenged, non-vaccinated control animals, as well as in all ZEBOV-challenged animals, while vaccinated animals challenged with MARV-Musoke showed few histological changes, except for splenic hyperplasia consistent with a post-challenge immune response and B-cell hyperplasia.

Example 3: MVA-BN-Filo in Non-Human Primates

This experiment tested MVA-BN-Filo in non-human primates under a similar study protocol as described in Example 2 but challenged with another Marburg virus strain, i.e., Marburg Angola instead of Marburg Musoke in Example 2.

TABLE 3

Study design and outcome for MVA-BN-Filo in non-human primates.

| | | Test/Control Article Administration | | | | |
|---|---|---|---|---|---|---|
| Group | N | Vaccination | Dose | Schedule | Challenge | Survival |
| 1 | 2 | MVA-BN ® Filo | $5\times10^8$ $TCID_{50}$ | 0, 28 | Marburg Angola Day 56 | 2/2 |
| 2 | 3 | MVA-BN ® MARV-IL15sushi | $1\times10^8$ $TCID_{50}$ | | | 2/3 |
| 3 | 3 | MVA-BN ®MARV-CD40L | $1\times10^8$ $TCID_{50}$ | | | 3/3 |
| 4 | 3 | MVA-BN ® MARV-TRICOM | $1\times10^8$ $TCID_{50}$ | | | 2/3 |
| 5 | 1 | TBS | n/a | | | 0/1 |

Intramuscular challenge (1,000 pfu) with MARV Angola strain; surviving animals were euthanized on Day 70.

Figure 7A:
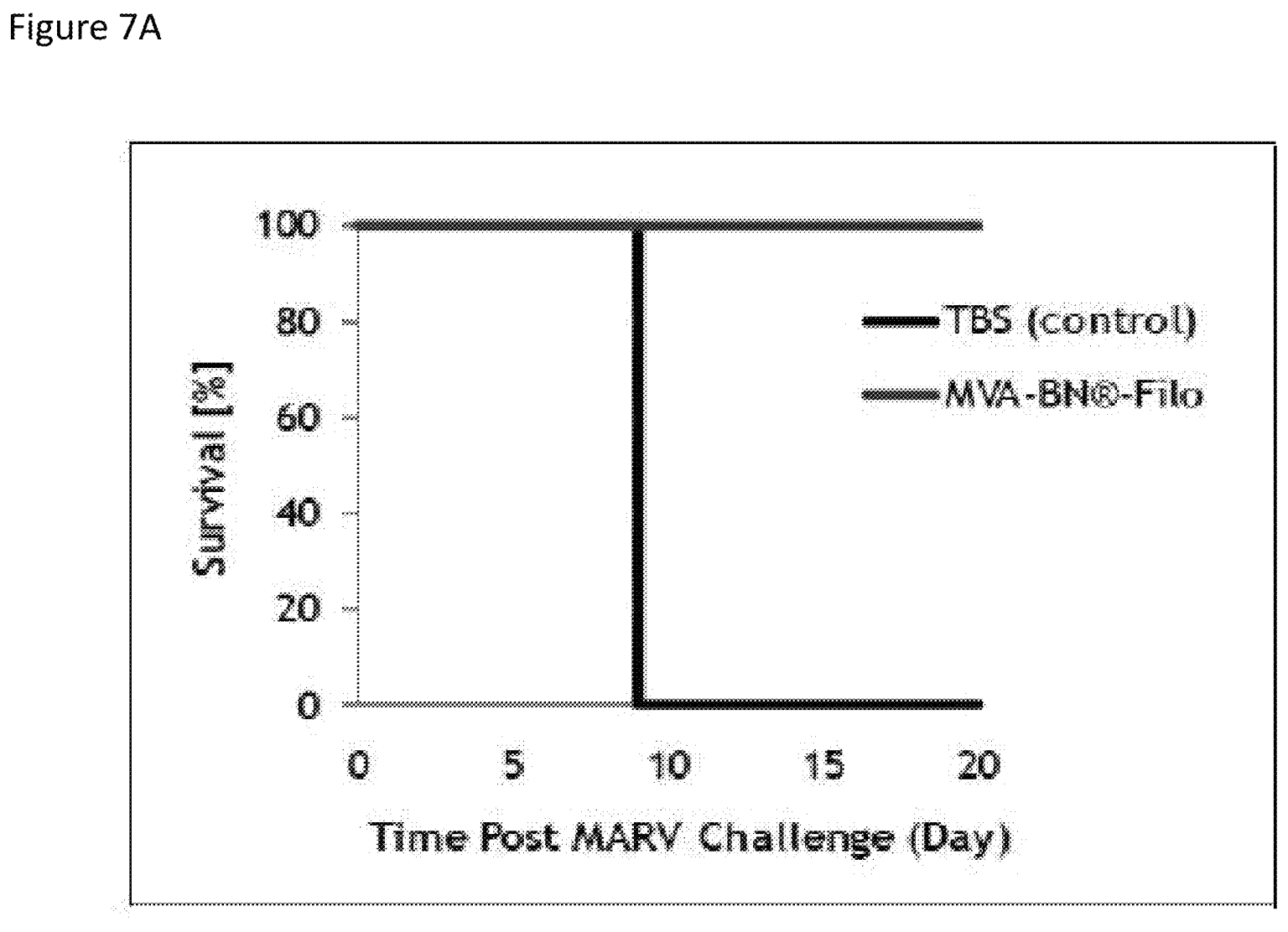

Results of the experiment are summarized in FIGS. 7A and 7B. FIG. 7A shows that vaccination with MVA-BN-Filo protected 100% of animals from challenge with MARV-Musoke. FIG. 7B shows clinical scores post-challenge; vaccinated animals challenged with MARV-Musoke showed no symptoms or histological changes associated with hemorrhagic fever and harbored no virus in liver, spleen, adrenal glands, lymph nodes, or lungs.

Table 3 shows that MVA-BN-Filo completely protects non-human primates against the Angola strain of Marburg virus. In contrast, the non-vaccinated animal in group 5 succumbed to infection. It also shows that protective efficacy is dose dependent, since a 5-fold lower dose using MVA-BN-MARV, encoding also GP of Marburg virus, is only partially protective, unless it co-expresses CD40L as co-stimulatory molecule. All vaccine candidates produce antibodies specific for the MVA vector (Vaccinia specific antibodies), as well as antibodies specific for the MARV GP insert, as outlined in Table 4.

TABLE 4

Antibodies induced by MVA-BN-Filo in non-human primates.

| Day 35 | MVA-Multi-valent | MVA-MARV IL-15 | MVA-MARV CD40L | MVA-MARV TRICOM |
|---|---|---|---|---|
| Vaccinia-Elisa | 21596 | 17838 | 6560 | 3246 |
| Vaccinia-PRNT | 1735 | 507 | 94 | 85 |
| MARV/GP-ELISA | 298959 | 285187 | 199132 | 409941 |

Example 4: Heterologous Prime/Boost

This experiment tested the combination of recombinant MVA and recombinant fowlpox FPV in prime/boost immunizations.

H-$2K^{k+}$ B6CBA F1 mice (Janvier Labs, France) were immunized subcutaneously (s.c.) with $5\times10^7$ $TCID_{50}$ MVA-ZEBOV-GP (MVA; MVA-mBN254A, FIG. 3C) or FPV-ZEBOV-GP (FPV; FPVmBN368A, FIG. 3D). The virus dose was injected at both flanks in a total volume of 100 μl/flank.

For the detection of ZEBOV-GP-specific IgG, 96-well plates (Corning, MA, USA) were coated with ZEBOV GP antigen (IBT Bioservices, MD, USA) at 4° C. over night. Duplicates of two-fold serum dilutions were added onto washed and blocked plates and a sheep anti-mouse IgG-HRP (AbD Serotec, UK) was used as detection antibody. TMB substrate was added for 30 minutes at RT and the reaction was stopped by the addition of 1M $H_2SO_4$. The absorbance was measured at 450 nm. The murine monoclonal antibody 13F6 was used as a standard in order to calculate the serum concentration of ZEBOV-GP IgG.

Mouse lymphocytes were freshly isolated from spleens by gently grinding and forcing the tissue through a 70 μm cell strainer (BD Bioscience, CA, USA). After erylysis, cells were incubated with 5 μg/ml ZEBOV-$GP_{577-584}$ peptide (TELRTFSI) (SEQ ID NO:20) (GenScript, NJ, USA) for 6 hours at 37° C. in complete RPMI in the presence of 10 μg/ml brefeldin A and CD107a-FITC. For live/dead discrimination, cells were stained using the Zombie Aqua™ Fixable Viability kit (BioLegend, CA, USA). Intracellular staining of IFN-' and TNF-α was performed after surface staining with CD4-BV605, CD8α-BV421 (BioLegend, CA, USA) and CD44-APC-eFluor780 (eBisocience, CA, USA) and fixation/permeabilization according to the manufacturers' instructions (BD Cytofix/Cytoperm, BD Biosciences). All cells were acquired using a digital flow cytometer (LSR II, BD Biosciences, CA, USA) and data were analyzed with FlowJo software (FlowJo, OR, USA).

The four possible combinations of recombinant MVA and FPV prime/boost immunizations were tested in H-$2K^{k+}$ CBAB6 F1 mice, because a strong CD8 T cell epitope from Zaire Ebola virus (ZEBOV) glycoprotein (GP) was described for this MHC class I haplotype, namely $GP_{577-584}$ (TELRTFSI) (SEQ ID NO:20) (Rao et al., *Vaccine* 17(23-24):2991-8 (1999)). The serum concentration of ZEBOV-GP-specific IgG was analyzed on day 21 and 41 after s.c. immunization on day 0 and 21. While on day 21 all MVA-immunized mice had robust IgG titers, only 20% of FPV-immunized mice had seroconverted. After the second immunization, all animals were seropositive for ZEBOV-GP-specific IgG. The lowest titers were observed after homologous immunization with FPV. Between the animals immunized twice with MVA and those primed with FPV and boosted with MVA no difference in the concentration of GP-specific IgG could be detected on day 41. The mice primed with MVA and boosted with FPV, however, had slightly higher titers than all other groups on day 41 (FIG. 8A).

Figure 8B:
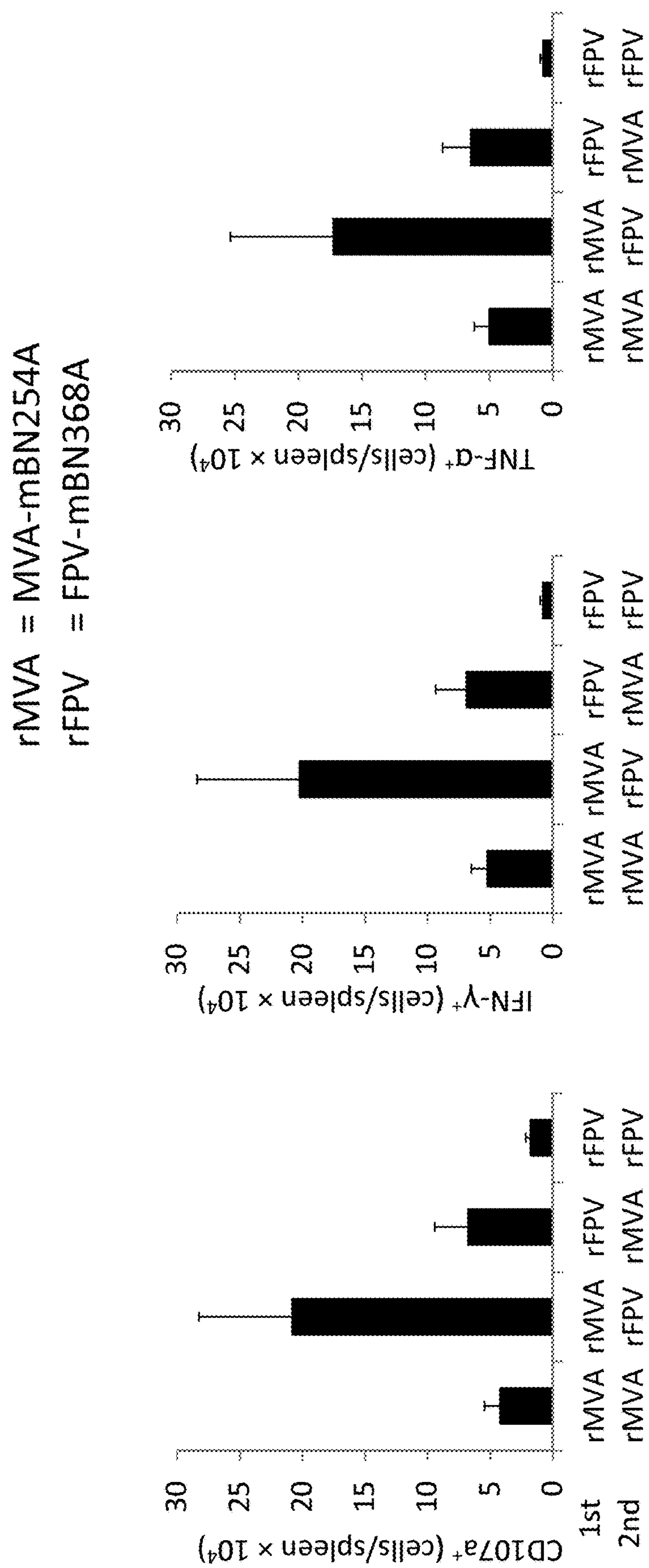
FIG. 8 shows the antibody and CD8 T cell response after heterologous MVA/FPV immunization. H-2K$^{k+}$ B6CBA F1 mice were immunized s.c. with $5\times10^7$ $TCID_{50}$ MVA-ZEBOV-GP (MVA; MVA-mBN354A, see FIG. 3C) or FPV-ZEBOV-GP (FPV; FPVmBN368A, see FIG. 3D) on day 0 and 21. A) Mice were bled on day 21 and 41 for antibody analysis. Shown is the mean concentration of ZEBOV-GP-specific antibodies +/− SEM. B) On day 41, mice were sacrificed and spleens were analyzed flow-cytometrically after re-stimulation with $GP_{577-584}$ peptide. Shown is the absolute number of CD107a$^+$, IFN-$\gamma^+$ and TNF-$\alpha^+$ CD8 T cells per spleen$\times10^4$+/− SEM. rMVA=recombinant MVA-ZEBOV-GP (MVA-mBN254); rFPV=recombinant FPV-ZEBOV-GP (FPV-mBN368).

Interestingly, the same combination that resulted in the strongest antibody response also induced the strongest CD8 T cell response. Again, homologous immunization with FPV resulted in the weakest CTL response, followed by MVA-MVA and FPV-MVA immunizations. Priming with MVA followed by a boost with FPV induced ~5-fold more cytotoxic CD8 T cells than the homologous combination of 2×MVA (FIG. 8B).

Taken together, these data imply that heterologous immunization with MVA first and FPV second induces the strongest ZEBOV-GP-specific antibody response and also the strongest CTL response, as shown by the presence of highly functional CD8 T cells.

Example 5: Enhanced ZEBOV-GP Specific CD8 T Cell Response

H-$2K^{k+}$ CBA mice were immunized s.c. with $5\times10^7$ $TCID_{50}$ MVA or FPV on day 0 and 21. Mice (5 each per group) were sacrificed on day 42 for T cell analysis by intracellular cytokine staining of splenocytes. The following prime/boost regimens were used: 1: MVA-ZEBOV-GP (mBN254)/FPV-ZEBOV-GP (mBN368), 2: MVA-multi-filo (MVA-mBN226)/FPV-ZEBOV-GP (mBN368), 3: MVA-ZEBOV-GP-VP40 (mBN255)/FPV-ZEBOV-GP (mBN368). Data are summarized in FIG. 9.

Figure 9:
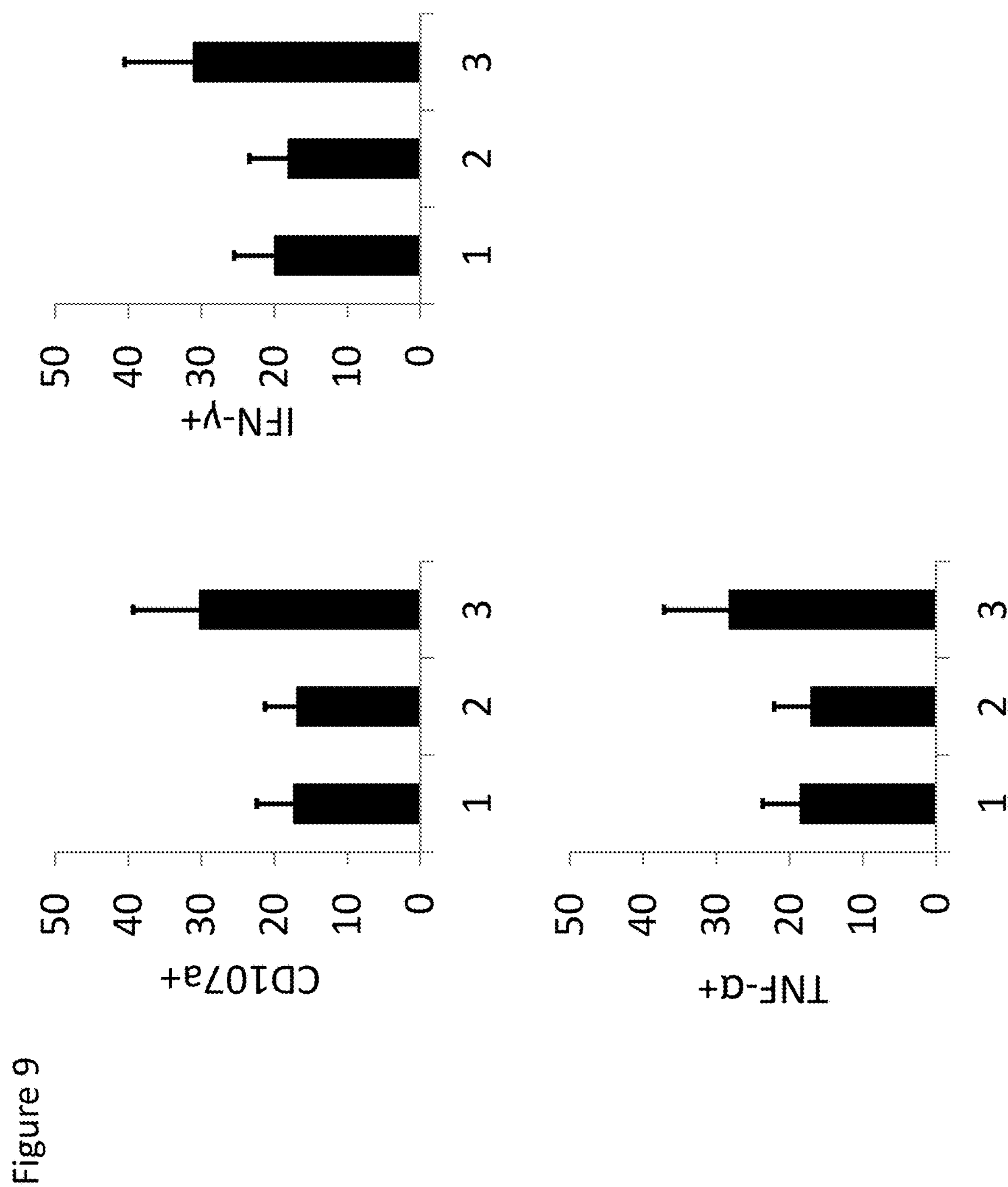
FIG. 9 shows the ZEBOV-GP specific CD8 T cell response after immunization (s.c) of mice with MVA/FPV. Shown is the absolute number of CD107a$^+$, IFN-$\gamma^+$ and TNF-$\alpha^+$ CD8 T cells per spleen x $10^4$+/− SEM. 1: MVA-mBN254/FPV-mBN368; 2: MVA-mBN226/FPV-mBN368, 3: MVA-mBN255/FPV-mBN368.

Splenic CD8 T cell responses were analysed on day 42 after standard 6 hour in vitro re-stimulation with 5 μg/ml ZEBOV-$GP_{577-584}$ peptide (TELRTFSI) (SEQ ID NO:20) in the presence of 10 μg/ml brefeldin A and anti-CD107a-FITC. Cells were surface stained with anti-CD4-BV605, anti-CD8-BV421, CD44-APC-eFluor780 and intracellularly with anti-IFN-γ-PECy7 and anti-TNF-α-PerCP-eFluor710. Live/dead discrimination was performed by LIVE/DEAD® Fixable Aqua Dead Cell Stain Kit according to the manufacturer's instruction (Life Technologies). Bar graphs show the total number of CD107a+, IFN-γ+ and TNF-α+CD8 T cells. Shown is the mean±SEM form 5 mice/group. The CD8 T cell response against the ZEBOV-GP-derived peptide TELFRTSI (SEQ ID NO: 20) was enhanced approximately 2-fold when MVA-BN-ZEBOV/GP-VP40 was used as the priming construct in a MVA-FPV heterologous prime-boost regimen compared to MVA-ZEBOV-GP (mBN254) or MVA-multi-filo (MVA-mBN226) as priming constructs (FIG. 9).

Example 6: Enhanced Protection of NHPs Against ZEBOV after Vaccination with MVA-GP-VP40

Cynomolgus macaques (*Macaca fascicularis*) were vaccinated twice (on Day 0 and 28) subcutaneously with a dose of $5\times10^8$ $TCID_{50}$ with either MVA-BN-ZEBOV/GP (n=3), MVA-BN-ZEBOV/GP-VP40 (n=3), or received Tris-buffered saline (TBS) as negative control (placebo group, n=2). Prior to immunization and weekly before challenge (Days 7, 14, 21, 28, 35 and 40) serum was collected for analysis by Ebola virus Zaire glycoprotein (GP)-specific and MVA-backbone-specific ELISA. Four weeks after the booster vaccination, animals were challenged with Ebola virus Zaire (Kikwit strain) by intramuscular administration of approximately 1000 pfu.

TABLE 5

| Study design: | | | | | | |
|---|---|---|---|---|---|---|
| | Vaccination | | | Challenge | | |
| Group | Vaccine | Dose | Schedule (Route) | Virus | Schedule | Survival |
| 1 | MVA-BN-ZEBOV/GP | 5 × $10^8$ $TCID_{50}$ | Day 0 + 28 (s.c.) | ZEBOV Kikwit Approx. 1000 pfu i.m. | 4 weeks post last vaccination | 0/3 |
| 2 | MVA-BN-ZEBOV/GP-VP40 | 5 × $10^8$ $TCID_{50}$ | Day 0 + 28 (s.c.) | | | 2/3 |
| 3 | TBS control | n/a | Day 0 + 28 (s.c.) | | | 0/2 |

Zaire Ebola Virus (ZEBOV)-Specific ELISA

An ELISA was performed determining ZEBOV/GP-specific antibodies immobilized by recombinant ZEBOV/GP and detected by a horse radish peroxidase (HRP)-conjugated antibody against NHP IgG. The amount of bound HRP-labeled antibody was read out after a substrate reaction as optical density (OD) value at 450 nm. The antibody concentration was calculated according to the Four Parameter regression analysis and based on a standard curve using monoclonal mouse antibody.

ELISA results are depicted in FIG. 10. All animals vaccinated with the MVA-BN-ZEBOV/GP or MVA-BN-ZEBOV/GP-VP40 construct had detectable backbone- and ZEBOV-specific antibodies already after the prime vaccination and antibody responses were boosted by a second vaccination.

In a second study cynomolgus macaques (*Macaca fascicularis*) were vaccinated three times (on Day 0, 28 and 56) subcutaneously with a dose of 5×$10^8$ $TCID_{50}$ of either MVA-BN-multi-filo (MVA-mBN226, n=2), with MVA-BN-ZEBOV/GP-VP40 (MVA-mBN255, n=2), or received Tris-buffered saline (TBS) as negative control (placebo group, n=2). Prior to immunization and weekly before challenge (Days 0, 27, 41 55, 35 and 67) serum was collected for analysis by Ebola virus Zaire glycoprotein (GP)-specific neutralizing assay (FIG. 11). Four weeks after the last vaccination, animals were challenged with Ebola virus Zaire (Kikwit strain) by intramuscular administration of approximately 100 pfu.

TABLE 6

| Study design: | | | | | | |
|---|---|---|---|---|---|---|
| | Vaccination | | | Challenge | | |
| Group | Vaccine | Dose | Schedule | Virus | Schedule | Survival |
| 1 | Negative control | n/a | Day 0 + 56 | ZEBOV Kikwit approx. 100 pfu IM | 4 weeks post last vaccination | 0/2 |
| 2 | MVA-BN-multi-filo | 5 × $10^8$ $TCID_{50}$ | Day 0 + 28 + 56 | | | 0/2 |
| 3 | MVA-BN-ZEBOV/GP-VP40 | 5 × $10^8$ $TCID_{50}$ | Day 0 + 28 + 56 | | | 2/2 |

Vaccination with MVA-BN-ZEBOV/GP-VP40 resulted in neutralizing antibodies detectable already after the prime vaccination, while MVA-BN-multi-filo did not induce detectable levels of neutralizing antibodies after prime at day 27 (FIG. 11). Animals vaccinated with MVA-BN-ZEBOV/GP-VP40 had higher neutralizing antibody titers than MVA-BN-multi-filo vaccinated animals throughout all time points of analysis. After ZEBOV challenge MVA-BN-multi-filo succumbed by day 7 post challenge whereas MVA-BN-ZEBOV/GP-VP40 vaccinated animals survived with no symptoms or a transient fever episode.

Example 7: VLP Formation and Protein Expression of GP and VP40

HeLa cells were infected with the indicated viruses at a MOI of 10. After 2 days of infection, supernatants were harvested and VLPs in the cleared supernatants (SNs) were then pelleted through a 20% sucrose cushion by ultracentrifugation (UC-SN). Cellular lysates were prepared by direct lysis of cells in 1× Laemmli buffer. Cell lysates were diluted 1:5 prior to separation by SDS-PAGE for immunoblot analysis. UC-SN was not diluted prior to SDS-PAGE. ZEBOV-GP was detected using a monoclonal mouse antibody (clone 6D8) from USAMRIID, and ZEBOV-VP40 was detected using a purified rabbit polyclonal antibody from IBT Bioservices.

Figure 12:
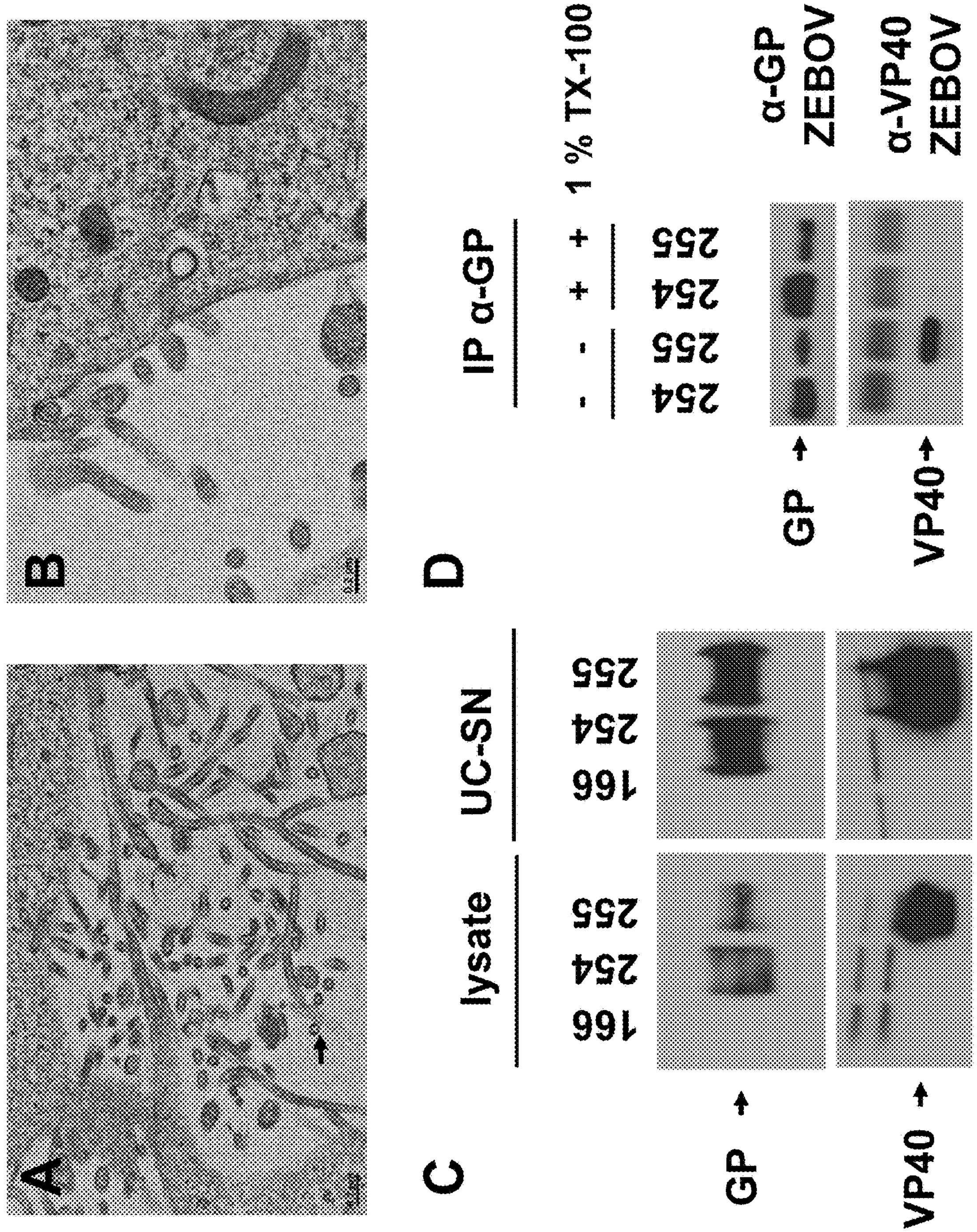
FIGS. 12 A) and B) shows the formation of filovirus-like particles in HeLa cells infected with MVA-BN-ZEBOV/GP-VP40 (MVA-mBN255). A, B) Transmission electron microscopy (TEM) analysis of MVA-BN-ZEBOV/GP-VP40 (VLP) and MVA wt infected HeLa cells. HeLa cells were infected with MVA-BN-ZEBOV/GP-VP40 (A) or BAC-derived MVA-wt (B) at an MOI of 10 and thin sections were generated and processed for TEM. Arrow: Transverse section of VLP generated by MVA-BN-ZEBOV/GP-VP40. C) Shows an immunoblot analysis of (co-)expression of GP and VP40 in Hela cells. D) Shows an immunoblot of immunoprecipitates from the supernatants of HeLa cells (aliquots of the same supernatants as shown in C) infected with MVA-BN-ZEBOV/GP-VP40 at an MOI of 10 for 2 days. VP40 and GP can only be co-precipitated if present in intact VLPs but not after disruption of VLPs with Triton-X-100 (1%). 166: MVA-mBN166, 254: MVA-mBN254, 255: MVA-mBN255.

Expression of GP and VP40 was confirmed in the fresh preparations by immunoblot. Both proteins were present in cellular lysates and were also enriched in the UC-SN (FIG. 12C). Expression of the matrix protein VP40 is known to be sufficient for the formation of VLPs and no direct interaction of VP40 and GP protein has been reported. To show that GP is indeed incorporated into VLPs together with VP40 GP was immunoprecipitated from the SN of infected cells. For this purpose, HeLa cells were infected with MVA-ZEBOV/GP-VP40 and control cells with MVA-ZEBOV/GP and BAC-derived MVA wt. BAC-derived MVA wt has been described previously in Meisinger-Henschel et al (Meisinger-Henschel et al. (2010), *J Virol.* 84(19):9907-9919). The SNs from infected cells were subjected to immunoprecipitation (IP) using an anti-GP-specific antibody. Aliquots of SNs were treated with 1% Triton X-100 (TX-100) for 30 minutes prior to immunoprecipitation, which was previously shown to disrupt the majority of mature enveloped VLPs of the murine leukemia virus (Davidoff et al. (2012), *Virology* 433(2):401-409).

The IP-complexes were then analyzed by immunoblot for the presence of GP and of co-precipitated VP40. For immunoprecipitation (IP), cleared SNs were incubated with anti-ZEBOV-GP (clone 6D8, USAMRIID) antibody together with Protein G-Agarose (10 μl) at 4° C. overnight. Immunoblots of the immunoprecipitates were then incubated with antibodies against ZEBOV-GP (monoclonal antibody 6D8) and ZEBOV-VP40 (from IBT). GP protein was immunoprecipitated efficiently from the SN of cells expressing only GP (FIG. 12D, top panel) which was independent of the presence of VP40. Importantly, VP40 co-immunoprecipitated with GP from supernatants of MVA-ZEBOV/GP-VP40 infected cells only in the absence of TX-100 (FIG. 12D, bottom panel, lane 2), indicating that GP had indeed been incorporated into VLPs. Since TX-100 is supposed to disrupt VLPs and since no direct GP-VP40 interaction exists, no VP40 could be co-precipitated in the TX-100 treated samples (FIG. 12D, bottom panel, lane 4). Thus, it was shown that indeed GP presenting VLP were produced upon infection with recombinant MVA.

Example 8: VLP Formation in 293T/17

To possibly get higher VLP concentrations after infection of cells, 293T/17 cells for the preparation of fresh VLPs. Protein contents of preparations were analyzed for GP and VP40 by Western Blot.

293T/17 cells in T175 culture dishes were infected with the indicated viruses at a MOI of 10. Supernatants were collected 24 h post infection and either directly mixed with 3× loading buffer (crude SN) or concentrated over a 20% sucrose cushion (UZ-prep). Cellular lysates (CL) were prepared in 1× loading buffer. Proteins were separated according to size by denaturing SDS-PAGE. Immunoblots were incubated with anti-GP antibody (clone 6D8, 1:2500, USAMRIID) or anti-VP40 antibody (polyclonal, 1:1000, IBT) and were developed using a chemiluminescence substrate.

Expression of EBOV glycoprotein (GP) was readily detectable after infection of cells with MVA-ZEBOV/GP and MVA-ZEBOV/GP-VP40 (MVA-filo-VLP), VP40 after infection of MVA-filo-VLP, both in cellular lysate (CL) and supernatant (SN) from infected cells. Surprisingly, MVA-ZEBOV/GP-infected cells seem to express more GP when compared to cells infected with MVA-filo-VLP, whereas with MVA-filo-VLP more GP was found in the SN. This possibly reflects the fact that with MVA-filo-VLP, the co-expression of GP and VP40 enhances GP release (in form of VLP) from infected cells. Both, GP and VP40 proteins were present in the UZ-preps, indicating that GP and VP40 were collected by UZ. Some GP and also VP40 was still present in SN after UZ, although less when compared to crude SN, especially true for VP40. Thus, VP40—mainly present in form of VLPs, together with GP—is largely depleted from SN, whereas parts of the GP pool (possibly in form of pleomorphic particles) remain in the SN after UZ.

Transmission electron microscopy (TEM) and immuno-electron microscopy analysis of VLPs from 293T/17 cells showed that MVA-filo-VLPs produced by the respective MVA recombinant were densely decorated with GP, GP spikes lining the entire surface of a filo-VLP. Additionally, preparations from cells infected with MVA-wt or MVA-ZEBOV/GP were analyzed by immuno-EM; no VLPs were detected in these samples.

Example 9: Immunogenicity of Heterologous Prime-Boost Immunization in NHP

Four cynomolgus macaques were vaccinated (s.c.) on Days 0 and 28. Two animals received as prime $5\times10^8$ $TCID_{50}$ MVA-mBN226 Day 0 and as boost $1\times10^9$ $TCID_{50}$ FPV-mBN368 Day 28. One animal received as prime $1\times10^9$ $TCID_{50}$ FPV-mBN368 Day 0 and as boost $5\times10^8$ $TCID_{50}$ MVA-mBN226. One control animal only received TBS. On Days 0, 7, 28, 35 and 49 PBMC were isolated. Blood was collected at Day 0, 28 and 49 for hematology, clinical chemistry, coagulation parameters, isolation of PBMCs or serum for analysis of T cell and antibody responses, respectively, and for viral load analysis. Serum samples were analyzed for Ebola specific humoral responses by ELISA and FRNT. GP- and Vaccinia-specific T cells were analyzed by in vitro re-stimulation of PBMC with a ZEBOV/GP peptide library with Vaccinia Wyeth, followed by detection of IFN-γ secreting cells by ELISPOT. All animals received an intramuscular (i.m.) challenge (100 pfu) of EBOV Kikwit-9510621 on Day 56. All three animals who received heterologous prime boost with MVA and FPV survived. Full seroconversion was already obtained after prime which was further improved by the boost.

Description of the Sequence Listing

SEQ ID NO:1 [DNA sequence encoding GP-SEBOV-Maleo (GenBank Accession No. U23069.1)]

SEQ ID NO:2 [amino acid sequence of GP-SEBOV-Maleo (GenBank Accession No. U23069.1)]

SEQ ID NO:3 [DNA sequence encoding NP-SEBOV-Boniface (GenBank Accession No. AF173836.1)]

SEQ ID NO:4 [amino acid sequence of NP-SEBOV-Boniface (GenBank Accession No. AF173836)]

SEQ ID NO:5 [codon-optimized DNA sequence encoding GP-MARV-Musoke (GenBank Accession No. ABA87127.1 for protein sequence)]

SEQ ID NO:6 [amino acid sequence of GP-MARV-Musoke (GenBank Accession No. ABA87127.1)]

SEQ ID NO:7 [DNA sequence encoding TTC]

SEQ ID NO:8 [amino acid sequence of TTC]

SEQ ID NO:9 [DNA sequence encoding hCD40L]

SEQ ID NO:10 [amino acid sequence of hCD40L]

SEQ ID NO:11 [DNA sequence encoding hIL15R-Sushi]

SEQ ID NO:12 [amino acid sequence of hIL15R-Sushi]

SEQ ID NO:13 [DNA sequence encoding human LFA-3/CD58 (EMBL-CDS Accession No. CAA75083.1)]

SEQ ID NO:14 [amino acid sequence of human LFA-3/CD58 (UniProtKB/SwissProt Accession No. P19256)]

SEQ ID NO:15 [DNA sequence encoding human ICAM-1/CD54 (GenBank Accession No. BT006854)]

SEQ ID NO:16 [amino acid sequence of human ICAM-1/CD54 (UniProtKB/SwissProt Accession No. P05362)]

SEQ ID NO:17 [DNA sequence encoding human B7.1/CD80 (EMBL-CDS Accession No. AAA58390.1)]

SEQ ID NO:18 [amino acid sequence of human B7.1/CD80 (UniProtKB/SwissProt Accession No. P33681)]

SEQ ID NO:19 [codon-optimized DNA encoding GP-ZEBOV-Mayinga (GenBank Accession No. ABX75367.1)]

SEQ ID NO:20 [amino acid sequence of GP-ZEBOV-Mayinga (GenBank Accession No. ABX75367.1)]

SEQ ID NO:21 [DNA sequence encoding W B5R anchor]

SEQ ID NO:22 [amino acid sequence of W B5R anchor]

SEQ ID NO:23 [DNA sequence of PrS promoter]

SEQ ID NO:24 [DNA sequence of PrS5E promoter: 1× (PrS)+5× (Pr7.5e)]

SEQ ID NO:25 [DNA sequence of Pr7.5 promoter]

SEQ ID NO:26 [DNA sequence of the FPV-40K promoter of FPV

SEQ ID NO:27 [DNA sequence of PrLE1 promoter—1× (ATI)+5× (Pr7.5e)]

SEQ ID NO:28 [codon-optimized DNA sequence encoding NP-EBOV-Cdl (GenBank Accession No. ACI28629.1)]

SEQ ID NO:29 [amino acid sequence of NP-EBOV-Cdl (GenBank Accession No. ACI28629.1)]

SEQ ID NO:30 [codon optimized DNA sequence encoding GP-SEBOV-Gulu (GenBank Accession No. AAU43887.1)]

SEQ ID NO:31 [amino acid sequence of GP-SEBOV-Gulu (GenBank Accession No. AAU43887.1)]

SEQ ID NO:32 [DNA sequence of PrLE1 promoter—1× (ATI)+4× (Pr7.5e)]

SEQ ID NO:33 [codon optimized DNA sequence DNA sequence encoding VP40-ZEBOV-Mayinga sequence]

SEQ ID NO:34 [amino acid sequence of VP40-ZEBOV-Mayinga sequence]

SEQ ID NO:35 [Pr13.5 promoter sequence]

SEQ ID NO:36 [codon optimized DNA sequence DNA sequence encoding GP-MARV-Angola]

SEQ ID NO:37 [amino acid sequence of GP-MARV-Angola]

The invention claimed is:

1. A recombinant MVA vector comprising a first nucleic acid encoding at least one immunogenic protein of a MARV envelope glycoprotein (GP); a second nucleic acid encoding an immunogenic protein of Zaire Ebola virus (ZEBOV) envelope glycoprotein; a third nucleic acid encoding an immunogenic protein of Sudan Ebola virus (SEBOV) envelope glycoprotein; and a fourth nucleic acid encoding an immunogenic protein of Ebola virus Ivory Coast nucleoprotein.

2. The recombinant MVA vector of claim 1, wherein the MARV envelope glycoprotein is full-length MARV-Musoke envelope glycoprotein.

3. The recombinant MVA vector of claim 1, wherein the first nucleic acid encodes an immunogenic protein comprising the sequence set forth in SEQ ID NO:6.

4. The recombinant MVA vector of claim 3, wherein the first nucleic acid comprises the sequence set forth in SEQ ID NO:5.

5. The recombinant MVA vector of claim 1 that comprises a nucleic acid encoding an immunogenic protein having a sequence selected from the group consisting of: SEQ ID NO:2, SEQ ID NO:4, SEQ ID NO:6, SEQ ID NO:20, SEQ ID NO:29, SEQ ID NO:31, and SEQ ID NO:37.

6. The recombinant MVA vector of claim 1 that comprises a nucleic acid encoding an immunogenic protein comprising the sequence set forth in SEQ ID NO:6, SEQ ID NO:20, SEQ ID NO:29, or SEQ ID NO:31.

7. The recombinant MVA vector of claim 6, wherein said nucleic acid comprises the sequence set forth in SEQ ID NO:5, SEQ ID NO:19, SEQ ID NO:28, or SEQ ID NO:30.

8. The recombinant MVA vector of claim 1, wherein the administration provides protective immunity or a protective immune response in the subject.

9. The recombinant MVA vector of claim 1, wherein the recombinant MVA vector comprises at least one nucleic acid encoding the sequences set forth in SEQ ID NO:6, SEQ ID NO:20, SEQ ID NO:29, and SEQ ID NO:31.

10. The recombinant MVA vector of claim 1 further comprising a nucleic acid encoding CD40L.

11. The recombinant MVA vector of claim 10, wherein the CD40L comprises the amino acid sequence set forth in SEQ ID NO:10.

12. The recombinant MVA vector of claim 11, wherein the nucleic acid encoding CD40L comprises the sequence set forth in SEQ ID NO:9.

* * * * *

SEQUENCE LISTING

```
<160> NUMBER OF SEQ ID NOS: 37

<210> SEQ ID NO 1
<211> LENGTH: 2362
<212> TYPE: DNA
<213> ORGANISM: Artificial sequence
<220> FEATURE:
<223> OTHER INFORMATION: DNA sequence encoding GP-SEBOV-Maleo (GenBank
      Accession No. U23069.1)

<400> SEQUENCE: 1

atttgatgaa gattaagcct gattaaggcc caaccttcat ctttttacca taatcttgtt     60

ctcaatacca tttaataggg gtatacttgc caaagcgccc ccatcttcag gatctcgcaa    120

tggagggtct tagcctactc caattgccca gagataaatt tcgaaaaagc tctttctttg    180

tttgggtcat catcttattt caaaaggcct tttccatgcc tttgggtgtt gtgaccaaca    240

gcactttaga agtaacagag attgaccagc tagtctgcaa ggatcatctt gcatcaactg    300

accagctgaa atcagttggt ctcaacctcg aggggagcgg agtatctact gatatcccat    360

ctgcgacaaa gcgttggggc ttcagatctg gtgtgcctcc ccaagtggtc agctatgaag    420

caggagaatg ggctgaaaat tgctacaatc ttgaaataaa gaaaccggac gggagcgaat    480

gcttaccccc accgccggat ggtgtcagag gctttccaag gtgccgctat gttcacaaag    540

cccaaggaac cgggccctgc ccgggtgact atgcctttca caaggatgga gctttcttcc    600

tctatgacag gctggcttca actgtaattt acagaggagt caattttgct gagggggtaa    660

tcgcattctt gatattggct aaaccaaagg aaacgttcct tcaatcaccc cccattcgag    720

aggcagcaaa ctacactgaa aatacatcaa gttactatgc cacatcctac ttggagtacg    780

aaatcgaaaa ttttggtgct caacactcca cgaccctttt caaaattaac aataatactt    840

ttgttcttct ggacaggccc cacacgcctc agttcctttt ccagctgaat gataccattc    900

aacttcacca acagttgagc aacacaactg ggaaactaat ttggacacta gatgctaata    960

tcaatgctga tattggtgaa tgggcttttt gggaaaataa aaaaatctct ccgaacaact   1020

acgtggagaa gagctgtctt tcgaaacttt atcgctcaac gagacagaag acgatgatgc   1080

gacatcgtcg agaactacaa agggaagaat ctccgaccgg gccaccagga agtattcgga   1140

cctggttcca aaggattccc ctgggatggt ttcattgcac gtaccagaag gggaaacaac   1200

attgccgtct cagaattcga cagaaggtcg aagagtagat gtgaatactc aggaaactat   1260

cacagagaca actgcaacaa tcataggcac taacggtaac aacatgcaga tctccaccat   1320

cgggacagga ctgagctcca gccaaatcct gagttcctca ccgaccatgg caccaagccc   1380
```

```
tgagactcag acctccacaa cctacacacc aaaactacca gtgatgacca ccgaggaacc   1440

aacaacacca ccgagaaact ctcctggctc aacaacagaa gcacccactc tcaccacccc   1500

agagaatata acaacagcgg ttaaaactgt ttgggcacaa gagtccacaa gcaacggtct   1560

aataacttca acagtaacag gtattcttgg gagccttgga cttcgaaaac gcagcagaag   1620

acaagttaac accagggcca cgggtaaatg caatcccaac ttacactact ggactgcaca   1680

agaacaacat aatgctgctg ggattgcctg gatcccgtac tttggaccgg gtgcagaagg   1740

catatacact gaaggcctta tgcacaacca aaatgcctta gtctgtggac tcagacaact   1800

tgcaaatgaa acaactcaag ctctgcagct tttcttaagg gccacgacgg agctgcggac   1860

atataccata ctcaatagga aggccataga tttccttctg cgacgatggg gcgggacatg   1920

taggatcctg ggaccagatt gttgcattga gccacatgat tggaccaaaa acatcactga   1980

taaaatcaac caaatcatcc atgatttcat cgacaaccct ttacccaatc aggataatga   2040

tgataattgg tggacgggct ggagacagtg gatccctgca ggaataggca ttactggaat   2100

tattattgca atcattgctc ttctttgcgt ctgcaagctg ctttgttgaa tatcaacttg   2160

aatcattaat ttaaagttga tacatttcta acattataaa ttataatctg atattaatac   2220

ttgaaaataa ggctaatgcc aaattctgtg ccaaacttga aagtaggttt accaaaatcc   2280

tttgaactgg aatgctttaa tgctctttct caatactata taagttcctt cccaaaataa   2340

tattgatgaa gattaagaaa aa                                            2362
```

<210> SEQ ID NO 2
<211> LENGTH: 676
<212> TYPE: PRT
<213> ORGANISM: SEBOV-MALEO

<400> SEQUENCE: 2

```
Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Gln Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Ala Asn Tyr Thr Glu Asn
```

-continued

```
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asn Asn Asn Thr
225                 230                 235                 240

Phe Val Leu Leu Asp Arg Pro His Thr Pro Gln Phe Leu Phe Gln Leu
                245                 250                 255

Asn Asp Thr Ile Gln Leu His Gln Gln Leu Ser Asn Thr Thr Gly Lys
            260                 265                 270

Leu Ile Trp Thr Leu Asp Ala Asn Ile Asn Ala Asp Ile Gly Glu Trp
        275                 280                 285

Ala Phe Trp Glu Asn Lys Lys Asn Leu Ser Glu Gln Leu Arg Gly Glu
    290                 295                 300

Glu Leu Ser Phe Glu Thr Leu Ser Leu Asn Glu Thr Glu Asp Asp Asp
305                 310                 315                 320

Ala Thr Ser Ser Arg Thr Thr Lys Gly Arg Ile Ser Asp Arg Ala Thr
                325                 330                 335

Arg Lys Tyr Ser Asp Leu Val Pro Lys Asp Ser Pro Gly Met Val Ser
            340                 345                 350

Leu His Val Pro Glu Gly Glu Thr Thr Leu Pro Ser Gln Asn Ser Thr
        355                 360                 365

Glu Gly Arg Arg Val Asp Val Asn Thr Gln Glu Thr Ile Thr Glu Thr
    370                 375                 380

Thr Ala Thr Ile Ile Gly Thr Asn Gly Asn Asn Met Gln Ile Ser Thr
385                 390                 395                 400

Ile Gly Thr Gly Leu Ser Ser Ser Gln Ile Leu Ser Ser Ser Pro Thr
                405                 410                 415

Met Ala Pro Ser Pro Glu Thr Gln Thr Ser Thr Thr Tyr Thr Pro Lys
            420                 425                 430

Leu Pro Val Met Thr Thr Glu Glu Pro Thr Thr Pro Pro Arg Asn Ser
        435                 440                 445

Pro Gly Ser Thr Thr Glu Ala Pro Thr Leu Thr Thr Pro Glu Asn Ile
    450                 455                 460

Thr Thr Ala Val Lys Thr Val Trp Ala Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Val Asn Thr Arg Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
    530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620
```

```
Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
        675
```

<210> SEQ ID NO 3
<211> LENGTH: 2926
<212> TYPE: DNA
<213> ORGANISM: Artificial sequence
<220> FEATURE:
<223> OTHER INFORMATION: DNA sequence encoding NP-SEBOV-Boniface (GenBank Accession No. AF173836.1)

<400> SEQUENCE: 3

```
ctcaaactca aactaatatt gacattgaga ttgatctcat catttaccaa ttggagacaa     60

tttaactagt taatccccca tttgggggca ttcctaaagt gttgcgaagg tatgtgggtc    120

gtattgcttg gccttttcct aacctggctc ctcctacaat tctaaccttc ttgataagtg    180

tggttaccag agtaatagac taaatttgtc ctggtagtta gcattttcta gtaagaccga    240

tactatccca agtctcaaga gagggtgaga ggagggcccc gaggtatccc tttagtccac    300

aaaatctagc caattttagc taagtggact gattaccttc atcacacgct atctactaag    360

ggtttacctg agagcctaca acatggataa acgggtgaga ggttcatggg ccctgggagg    420

acaatctgag gttgatcttg actaccacaa gatattaaca gccgggcttt cagtccaaca    480

ggggattgtg cgacagagag tcatcccggt atatgtcgtg aatgatcttg agggtatttg    540

tcaacatatc attcaggctt ttgaagcagg tgtagatttc caggataatg ctgatagctt    600

ccttttactt ttatgtttac atcatgccta ccaaggagat cataggctct tcctcaaaag    660

tgatgcagtt caatatttag agggccatgg cttcaggttt gaggtccgag aaaaggagaa    720

tgtgcaccgt ctggatgaat tgttgcccaa tgttaccggt ggaaaaaatc tcaggagaac    780

attggctgct atgcccgaag aggagacaac ggaagctaat gctggtcagt ttctatcctt    840

tgccagtttg tttctaccca aacttgtcgt tggggagaaa gcgtgcctgg aaaaagtaca    900

aaggcaaatt caggtccatg cagaacaagg gctcattcaa tatccaactt cctggcaatc    960

agttggacac atgatggtga tcttccgttt gatgaggaca aactttttaa tcaagtttct   1020

actaatacat caagggatgc acatggttgc aggtcatgat gcgaatgaca cagtaatatc   1080

taattctgtt gcccaggcaa ggttctctgg tcttctgatt gtaaagactg ttctggatca   1140

catcctacaa aaaacagatc tcggagtacg acttcatcca ctggccagga cagcaaaagt   1200

gaagaatgag gtcagttcat tcaaggcggc tcttggttca cttgccaagc atggagaata   1260

tgctccgttt gcacgtctcc ttaatctttc tggagtcaac aacttggaac atgggcttta   1320

tccacaactt tcagccatcg ctttgggtgt tgcaactgcc cacgggagta cgcttgctgg   1380

tgtgaatgta ggggagcaat atcagcaact gcgtgaggct gctactgagg ctgaaaagca   1440

actccaacaa tatgctgaaa cacgtgagtt ggataacctt gggcttgatg aacaggagaa   1500

gaagattctc atgagcttcc accagaagaa gaatgagatc agcttccagc agactaatgc   1560

aatggtaacc ttaaggaaag aacggctggc taaattgacc gaagccatca cgactgcatc   1620

gaagatcaag gttggagacc gttatcctga tgacaatgat attccatttc ccgggccgat   1680
```

```
ctatgatgac actcacccca atccctctga tgacaatcct gatgattcac gtgatacaac   1740

tattccaggt ggtgttgttg acccgtatga tgatgagagt aataattatc ctgactacga   1800

ggattcggct gaaggcacca caggagatct tgatctcttc aatttggacg acgacgatga   1860

tgacagccga ccaggaccac cagacagggg gcagaacaag gagagggcgg cccggacata   1920

tggcctccaa gatccgacct tggacggagc gaaaaaggtg ccggagttga ccccaggttc   1980

ccatcaacca ggcaacctcc acatcaccaa gtcgggttca aacaccaacc aaccacaagg   2040

caatatgtca tctactctcc atagtatgac ccctatacag gaagaatcag agcccgatga   2100

tcaaaaagat aatgatgacg agagtctcac atcccttgac tctgaaggtg acgaagatgg   2160

tgagagcatc tctgaggaga acaccccaac tgtagctcca ccagcaccag tctacaaaga   2220

cactggagta gacactaatc agcagaatgg accaagcagt actgtagata gtcaaggttc   2280

tgaaagtgaa gctctcccaa tcaactctaa aaagagttcc gcactagaag aaacatatta   2340

tcatctccta aaaacacagg gtccatttga ggcaatcaat tattatcacc taatgagtga   2400

tgaacccatt gcttttagca ctgaaagtgg caaggaatat atctttccag actcccttga   2460

agaagcctac ccgccgtggt tgagtgagaa ggaggcctta gagaaggaaa atcgttatct   2520

ggtcattgat ggccagcaat tcctctggcc ggtaatgagc ctacgggaca agttccttgc   2580

cgttcttcaa catgactgag gacctatgat tggtggatct tgtttattcc gagcctgatt   2640

ataattgttc tgataattca agtataagca cctaccccga aatataaacc ctatcttagt   2700

tataaggaaa ttaaataaat aacctgtaag ttataggact acgaagagct gcttgtgtca   2760

atttatcatg ggttgatacc cgtaccgcaa gaatcattat ttagtagttt tggtcagctt   2820

ctgatatgta ccaataagaa aacattatag cattaaaaca taaggtatct ttcaatgagc   2880

ttaggaggat aatatcctga taaattctat agaacttaag attaag                  2926
```

<210> SEQ ID NO 4
<211> LENGTH: 738
<212> TYPE: PRT
<213> ORGANISM: SEBOV-Boniface

<400> SEQUENCE: 4

```
Met Asp Lys Arg Val Arg Gly Ser Trp Ala Leu Gly Gly Gln Ser Glu
1               5                   10                  15

Val Asp Leu Asp Tyr His Lys Ile Leu Thr Ala Gly Leu Ser Val Gln
            20                  25                  30

Gln Gly Ile Val Arg Gln Arg Val Ile Pro Val Tyr Val Val Asn Asp
        35                  40                  45

Leu Glu Gly Ile Cys Gln His Ile Ile Gln Ala Phe Glu Ala Gly Val
    50                  55                  60

Asp Phe Gln Asp Asn Ala Asp Ser Phe Leu Leu Leu Leu Cys Leu His
65                  70                  75                  80

His Ala Tyr Gln Gly Asp His Arg Leu Phe Leu Lys Ser Asp Ala Val
                85                  90                  95

Gln Tyr Leu Glu Gly His Gly Phe Arg Phe Glu Val Arg Glu Lys Glu
            100                 105                 110

Asn Val His Arg Leu Asp Glu Leu Leu Pro Asn Val Thr Gly Gly Lys
        115                 120                 125

Asn Leu Arg Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
```

```
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ser Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Thr Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Asp Leu Gly Val Arg Leu His Pro Leu Ala Arg Thr Ala Lys
            260                 265                 270

Val Lys Asn Glu Val Ser Ser Phe Lys Ala Ala Leu Gly Ser Leu Ala
        275                 280                 285

Lys His Gly Glu Tyr Ala Pro Phe Ala Arg Leu Leu Asn Leu Ser Gly
    290                 295                 300

Val Asn Asn Leu Glu His Gly Leu Tyr Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Thr Arg Glu Leu Asp Asn Leu Gly Leu
        355                 360                 365

Asp Glu Gln Glu Lys Lys Ile Leu Met Ser Phe His Gln Lys Lys Asn
    370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Thr Ala Ser Lys Ile Lys
                405                 410                 415

Val Gly Asp Arg Tyr Pro Asp Asp Asn Asp Ile Pro Phe Pro Gly Pro
            420                 425                 430

Ile Tyr Asp Asp Thr His Pro Asn Pro Ser Asp Asp Asn Pro Asp Asp
        435                 440                 445

Ser Arg Asp Thr Thr Ile Pro Gly Gly Val Val Asp Pro Tyr Asp Asp
    450                 455                 460

Glu Ser Asn Asn Tyr Pro Asp Tyr Glu Asp Ser Ala Glu Gly Thr Thr
465                 470                 475                 480

Gly Asp Leu Asp Leu Phe Asn Leu Asp Asp Asp Asp Asp Asp Ser Arg
                485                 490                 495

Pro Gly Pro Pro Asp Arg Gly Gln Asn Lys Glu Arg Ala Ala Arg Thr
            500                 505                 510

Tyr Gly Leu Gln Asp Pro Thr Leu Asp Gly Ala Lys Lys Val Pro Glu
        515                 520                 525

Leu Thr Pro Gly Ser His Gln Pro Gly Asn Leu His Ile Thr Lys Ser
    530                 535                 540

Gly Ser Asn Thr Asn Gln Pro Gln Gly Asn Met Ser Ser Thr Leu His
545                 550                 555                 560

Ser Met Thr Pro Ile Gln Glu Glu Ser Glu Pro Asp Asp Gln Lys Asp
                565                 570                 575
```

```
Asn Asp Asp Glu Ser Leu Thr Ser Leu Asp Ser Glu Gly Asp Glu Asp
            580                 585                 590

Gly Glu Ser Ile Ser Glu Glu Asn Thr Pro Thr Val Ala Pro Pro Ala
        595                 600                 605

Pro Val Tyr Lys Asp Thr Gly Val Asp Thr Asn Gln Gln Asn Gly Pro
    610                 615                 620

Ser Ser Thr Val Asp Ser Gln Gly Ser Glu Ser Glu Ala Leu Pro Ile
625                 630                 635                 640

Asn Ser Lys Lys Ser Ser Ala Leu Glu Glu Thr Tyr Tyr His Leu Leu
                645                 650                 655

Lys Thr Gln Gly Pro Phe Glu Ala Ile Asn Tyr Tyr His Leu Met Ser
            660                 665                 670

Asp Glu Pro Ile Ala Phe Ser Thr Glu Ser Gly Lys Glu Tyr Ile Phe
        675                 680                 685

Pro Asp Ser Leu Glu Glu Ala Tyr Pro Pro Trp Leu Ser Glu Lys Glu
    690                 695                 700

Ala Leu Glu Lys Glu Asn Arg Tyr Leu Val Ile Asp Gly Gln Gln Phe
705                 710                 715                 720

Leu Trp Pro Val Met Ser Leu Arg Asp Lys Phe Leu Ala Val Leu Gln
                725                 730                 735

His Asp
```

<210> SEQ ID NO 5
<211> LENGTH: 2046
<212> TYPE: DNA
<213> ORGANISM: Artificial sequence
<220> FEATURE:
<223> OTHER INFORMATION: codon-optimized DNA sequence encoding GP-MARV-Musoke (GenBank Accession No. ABA87127.1 for protein sequence)

<400> SEQUENCE: 5

```
atgaaaacaa cctgcttcct gatcagcctg atcctgatcc agggcaccaa gaacctgccc     60

atcctggaaa tcgccagcaa caaccagccc cagaacgtgg atagcgtgtg cagcggcacc    120

ctgcagaaaa ccgaggacgt gcacctgatg ggcttcacac tgagcggcca gaaggtggcc    180

gatagccccc tggaagccag caagcgctgg gccttcagaa caggggtgcc acctaagaac    240

gtggagtaca cagagggcga ggaagccaag acctgctaca acatcagcgt gaccgacccc    300

agcggcaagt ccctgctgct ggaccccccct accaacatca gagactaccc taagtgcaag    360

accatccacc acatccaggg ccagaatcct cacgctcagg gcattgctct gcacctgtgg    420

ggcgcattct tcctgtatga cagaatcgcc tccaccacca tgtaccgggg caaggtgttc    480

acagagggca atatcgccgc catgatcgtg aacaagaccg tgcacaagat gatcttcagc    540

agacagggcc agggctaccg gcacatgaac ctgaccagca ccaacaagta ctggaccagc    600

agcaacggca cccagaccaa cgacaccggc tgctttggcg ccctgcagga atacaacagc    660

accaagaatc agacctgcgc ccccagcaag atccctcctc ccctgcctac cgccagaccc    720

gagatcaagc tgacaagcac ccccaccgac gccaccaagc tgaacaccac cgacccctcc    780

agcgacgatg aggacctggc aactagtggt agcggcagcg gagagagaga gccccacacc    840

acctccgatg ccgtgaccaa gcagggcctg agcagcacaa tgccccctac ccccagccct    900

cagcctagca caccccagca gggcggcaat aacaccaacc actcccagga cgccgtgacc    960

gagctggaca agaacaatac caccgcccag cctagcatgc ccccccacaa cactactacc   1020

atctccacca acaataccag caagcacaac ttcagcaccc tgagcgcccc tctgcagaac   1080
```

```
accaccaacg acaacaccca gagcaccatc acagagaacg agcagaccag cgccccttcc   1140

atcaccaccc tgccccccac cggcaatcct accaccgcca agagcaccag ctccaagaag   1200

ggtcctgcaa ctaccgcccc caacacaacc aacgagcact tcaccagccc tcccccaacc   1260

cctagctcca cagcccagca cctggtgtac ttccggcgga agcggtccat cctgtggcgg   1320

gagggcgaca tgttcccctt tctggacggc ctgattaacg cccccatcga cttcgacccc   1380

gtgcccaata ccaagaccat cttcgacgag agtagttcat caggtgcatc agccgaagag   1440

gatcagcacg ccagccccaa catctccctg accctgagct acttccccaa catcaatgag   1500

aacaccgcct acagcggcga gaacgagaac gactgcgacg ccgagctgag aatttggagc   1560

gtgcaggaag atgacctggc cgctggcctg agttggatac cattcttcgg cccaggcatc   1620

gagggtctgt acaccgccgt gctgatcaag aaccagaaca acctcgtgtg cagactgcgg   1680

agactggcca accagaccgc caagtccctg gaactgctgc tgagagtgac caccgaagag   1740

agaaccttct ccctgatcaa ccggcacgcc attgattttc tgctgacccg ctggggcgga   1800

acatgcaagg tcctgggtcc agactgttgt atcggcatcg aggacctcag caagaacatc   1860

agcgaacaga ttgaccagat caagaaggac gagcagaaag agggcacagg ctggggcctg   1920

ggcggcaagt ggtggaccag cgactggggc gtgctgacaa acctgggcat cctgctgctg   1980

ctgtctatcg ctgtgctgat tgccctgagc tgcatctgtc ggatcttcac caagtacatc   2040

ggctga                                                              2046
```

<210> SEQ ID NO 6
<211> LENGTH: 681
<212> TYPE: PRT
<213> ORGANISM: MARV-Musoke

<400> SEQUENCE: 6

```
Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190
```

```
Ser Thr Asn Lys Tyr Trp Thr Ser Ser Asn Gly Thr Gln Thr Asn Asp
        195                 200                 205

Thr Gly Cys Phe Gly Ala Leu Gln Glu Tyr Asn Ser Thr Lys Asn Gln
    210                 215                 220

Thr Cys Ala Pro Ser Lys Ile Pro Pro Pro Leu Pro Thr Ala Arg Pro
225                 230                 235                 240

Glu Ile Lys Leu Thr Ser Thr Pro Thr Asp Ala Thr Lys Leu Asn Thr
                245                 250                 255

Thr Asp Pro Ser Ser Asp Asp Glu Asp Leu Ala Thr Ser Gly Ser Gly
            260                 265                 270

Ser Gly Glu Arg Glu Pro His Thr Thr Ser Asp Ala Val Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Asp Ala Val Thr
305                 310                 315                 320

Glu Leu Asp Lys Asn Asn Thr Thr Ala Gln Pro Ser Met Pro Pro His
                325                 330                 335

Asn Thr Thr Thr Ile Ser Thr Asn Asn Thr Ser Lys His Asn Phe Ser
            340                 345                 350

Thr Leu Ser Ala Pro Leu Gln Asn Thr Thr Asn Asp Asn Thr Gln Ser
        355                 360                 365

Thr Ile Thr Glu Asn Glu Gln Thr Ser Ala Pro Ser Ile Thr Thr Leu
    370                 375                 380

Pro Pro Thr Gly Asn Pro Thr Thr Ala Lys Ser Thr Ser Ser Lys Lys
385                 390                 395                 400

Gly Pro Ala Thr Thr Ala Pro Asn Thr Thr Asn Glu His Phe Thr Ser
                405                 410                 415

Pro Pro Pro Thr Pro Ser Ser Thr Ala Gln His Leu Val Tyr Phe Arg
            420                 425                 430

Arg Lys Arg Ser Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Asn Ile Asn Glu Asn Thr Ala Tyr Ser Gly Glu Asn Glu Asn Asp Cys
            500                 505                 510

Asp Ala Glu Leu Arg Ile Trp Ser Val Gln Glu Asp Asp Leu Ala Ala
        515                 520                 525

Gly Leu Ser Trp Ile Pro Phe Phe Gly Pro Gly Ile Glu Gly Leu Tyr
    530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
        595                 600                 605

Cys Cys Ile Gly Ile Glu Asp Leu Ser Lys Asn Ile Ser Glu Gln Ile
```

```
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680
```

<210> SEQ ID NO 7
<211> LENGTH: 3642
<212> TYPE: DNA
<213> ORGANISM: Artificial sequence
<220> FEATURE:
<223> OTHER INFORMATION: DNA sequence encoding TTC

<400> SEQUENCE: 7

```
atggagaccg acaccctgct gctgtgggtc ctgctcctgt gggtgcccgg cagcaccggc     60

gacgaagtga agcaggaaaa ccggctgctg aacgagagcg agagcagcag ccagggcctg    120

ctgggctact acttcagcga cctgaacttc caggccccca tggtggtgac cagcagcacc    180

accggcgacc tgagcatccc cagcagcgag ctggaaaaca tccccagcga gaaccagtac    240

ttccagagcg ccatttggag cggcttcatc aaagtgaaga agtccgacga gtacaccttc    300

gccacctccg ccgacaacca cgtgaccatg tgggtggacg accaggaagt gatcaacaag    360

gccagcaaca gcaacaagat ccggctggaa aagggccggc tgtaccagat caagatccag    420

taccagagag agaaccccac cgagaagggc ctggacttca agctgtactg gaccgacagc    480

cagaacaaga aagaagtgat cagcagcgac aacctgcagc tgcccgagct gaagcagaag    540

tccagcaact cccggaagaa gcggagcacc agcgccggac ccaccgtgcc cgaccgggac    600

aacgacggca tccccgacag cctggaagtg gagggctaca ccgtggacgt gaagaacaag    660

cggaccttcc tgagcccctg gatcagcaac atccacgaga agaaggggct gaccaagtac    720

aagagcagcc ccgagaagtg gagcaccgcc agcgacccct acagcgactt cgagaaagtg    780

accggccgga tcgacaagaa cgtgtccccc gaggccagac accctctggt ggccgcctac    840

cccatcgtgc acgtggacat ggaaaatatc atcctgagca agaacgagga ccagagcacc    900

cagaacaccg actcccagac ccggaccatc agcaagaaca ccagcaccag cagaacccac    960

acaagcgaag tgcacggcaa cgccgaagtg cacgccagct tttcgacat cggagggagc    1020

gtgtccgccg gcttcagcaa ctccaacagc agcaccgtgg ccatcgacca cagcctgagc    1080

ctggccggcg agagaacctg ggccgagaca atgggcctga acaccgccga caccgccaga    1140

ctgaacgcca acatccgcta cgtgaacacc ggcaccgccc ccatctacaa cgtgctgccc    1200

accacctccc tggtgctggg caagaaccag accctggcca ccatcaaggc caaagagaac    1260

cagctgtccc agatcctggc ccccaacaac tactacccca gcaagaacct ggcccctatc    1320

gccctgaacg cccaggacga cttctcttct acccccatca ccatgaacta caaccagttt    1380

ctggaactgg aaaagaccaa gcagctgcgg ctggacaccg accaggtgta cggcaatatc    1440

gccacctaca acttcgagaa cggcagagtg cgcgtggaca ccggcagcaa ttggagcgag    1500

gtgctgcctc agatccagga aaccaccgcc cggatcatct tcaacggcaa ggacctgaac    1560

ctggtggagc ggcggatcgc cgccgtgaac cctccgacc ccctggaaac caccaagccc    1620

gacatgaccc tgaaagaggc cctgaagatc gccttcggct tcaacgagcc caacggcaac    1680
```

```
ctgcagtacc agggcaagga catcaccgag ttcgacttca acttcgacca gcagacctcc   1740
cagaacatca agaatcagct ggccgaactg aacgtgacca acatctacac agtgctggac   1800
aagatcaagc tgaatgccaa gatgaacatc ctgatccggg acaagcggtt ccactacgac   1860
cggaacaata tcgccgtggg cgccgacgag agcgtggtga aagaagccca ccgggaagtc   1920
attaacagct ccaccgaggg gctgctgctg aacatcgaca aggacatccg caagatcctg   1980
agcggctaca tcgtggagat cgaggacacc gagggcctga aagaagtcat taacgaccgc   2040
tacgacatgc tgaatatcag cagcctgcgg caggacggca agaccttcat cgacttcaag   2100
aagtacaacg acaagctgcc cctgtacatc agcaacccca actacaaagt gaacgtgtac   2160
gccgtgacca aagagaatac catcatcaac cctagcgaga acggcgacac ctccaccaac   2220
ggcatcaaga agatcctgat cttcagcaag aagggctacg agatcggcgg acccggccct   2280
aagaacctgg actgctgggt ggacaacgaa gaggacatcg acgtgatcct gaagaagtct   2340
accatcctga atctggacat caacaacgac atcatcagcg acatctccgg cttcaacagc   2400
agcgtgatca cctaccccga cgcccagctg gtgcctggca tcaatggcaa ggccatccac   2460
ctggtgaaca acgagagcag cgaagtgatc gtgcacaagg ccatggacat cgagtacaac   2520
gatatgttca acaacttcac cgtgtccttt tggctgcggg tgcccaaggt gtccgccagc   2580
cacctggaac agtacggcac caacgagtac agcatcatca gcagcatgaa gaagcacagc   2640
ctgtccatcg gcagcgggtg gagcgtgtcc ctgaagggca acaacctgat ctggaccctg   2700
aaggactctg ccggcgaagt gcggcagatc accttccgcg acctgcccga caagttcaac   2760
gcctacctgg ccaataagtg ggtgttcatc accatcacca acgacagact gtccagcgcc   2820
aacctgtata tcaacggcgt gctgatgggc agcgccgaga tcacaggcct gggcgccatc   2880
cgggaggaca acaacatcac cctgaagctg gaccggtgca acaacaacaa ccagtacgtg   2940
tccatcgaca agttccgcat cttctgcaag gccctgaatc ccaaagagat cgagaagctg   3000
tacaccagct acctgtccat cacctttctg cgggatttct ggggcaaccc tctgagatac   3060
gacaccgagt actacctgat ccccgtggcc agcagctcca aggacgtgca gctgaagaac   3120
atcaccgact acatgtacct gaccaacgcc cccagctaca ccaatggcaa gctgaacatc   3180
tactaccggc ggctgtacaa cggcctgaag ttcatcatca agcggtacac ccccaacaat   3240
gagatcgaca gcttcgtgaa gtccggcgac ttcatcaagc tgtatgtgtc ctacaacaac   3300
aatgagcaca tcgtgggcta ccccaaggac gggaacgcct tcaacaacct ggaccggatc   3360
ctgagagtgg gctacaacgc ccctggcatc cccctgtaca agaaaatgga agccgtgaag   3420
ctgcgggacc tgaaaaccta ctctgtgcag ctgaaactgt acgacgacaa gaacgccagc   3480
ctgggcctgg tggggaccca caacggccag atcggcaacg accccaaccg ggatatcctg   3540
atcgccagca actggtactt caaccacctg aaggacaaga tcctgggctg cgattggtac   3600
ttcgtgccca ccgacgaggg ctggaccaac gacaagcttt ga                      3642
```

<210> SEQ ID NO 8
<211> LENGTH: 1213
<212> TYPE: PRT
<213> ORGANISM: Homo sapiens

<400> SEQUENCE: 8

```
Met Glu Thr Asp Thr Leu Leu Leu Trp Val Leu Leu Leu Trp Val Pro
1               5                   10                  15

Gly Ser Thr Gly Asp Glu Val Lys Gln Glu Asn Arg Leu Leu Asn Glu
```

```
            20                  25                  30

Ser Glu Ser Ser Ser Gln Gly Leu Leu Gly Tyr Tyr Phe Ser Asp Leu
        35                  40                  45

Asn Phe Gln Ala Pro Met Val Val Thr Ser Ser Thr Thr Gly Asp Leu
    50                  55                  60

Ser Ile Pro Ser Ser Glu Leu Glu Asn Ile Pro Ser Glu Asn Gln Tyr
65                  70                  75                  80

Phe Gln Ser Ala Ile Trp Ser Gly Phe Ile Lys Val Lys Lys Ser Asp
                85                  90                  95

Glu Tyr Thr Phe Ala Thr Ser Ala Asp Asn His Val Thr Met Trp Val
            100                 105                 110

Asp Asp Gln Glu Val Ile Asn Lys Ala Ser Asn Ser Asn Lys Ile Arg
        115                 120                 125

Leu Glu Lys Gly Arg Leu Tyr Gln Ile Lys Ile Gln Tyr Gln Arg Glu
    130                 135                 140

Asn Pro Thr Glu Lys Gly Leu Asp Phe Lys Leu Tyr Trp Thr Asp Ser
145                 150                 155                 160

Gln Asn Lys Lys Glu Val Ile Ser Ser Asp Asn Leu Gln Leu Pro Glu
                165                 170                 175

Leu Lys Gln Lys Ser Ser Asn Ser Arg Lys Lys Arg Ser Thr Ser Ala
            180                 185                 190

Gly Pro Thr Val Pro Asp Arg Asp Asn Asp Gly Ile Pro Asp Ser Leu
        195                 200                 205

Glu Val Glu Gly Tyr Thr Val Asp Val Lys Asn Lys Arg Thr Phe Leu
    210                 215                 220

Ser Pro Trp Ile Ser Asn Ile His Glu Lys Lys Gly Leu Thr Lys Tyr
225                 230                 235                 240

Lys Ser Ser Pro Glu Lys Trp Ser Thr Ala Ser Asp Pro Tyr Ser Asp
                245                 250                 255

Phe Glu Lys Val Thr Gly Arg Ile Asp Lys Asn Val Ser Pro Glu Ala
            260                 265                 270

Arg His Pro Leu Val Ala Ala Tyr Pro Ile Val His Val Asp Met Glu
        275                 280                 285

Asn Ile Ile Leu Ser Lys Asn Glu Asp Gln Ser Thr Gln Asn Thr Asp
    290                 295                 300

Ser Gln Thr Arg Thr Ile Ser Lys Asn Thr Ser Thr Ser Arg Thr His
305                 310                 315                 320

Thr Ser Glu Val His Gly Asn Ala Glu Val His Ala Ser Phe Phe Asp
                325                 330                 335

Ile Gly Gly Ser Val Ser Ala Gly Phe Ser Asn Ser Asn Ser Ser Thr
            340                 345                 350

Val Ala Ile Asp His Ser Leu Ser Leu Ala Gly Glu Arg Thr Trp Ala
        355                 360                 365

Glu Thr Met Gly Leu Asn Thr Ala Asp Thr Ala Arg Leu Asn Ala Asn
    370                 375                 380

Ile Arg Tyr Val Asn Thr Gly Thr Ala Pro Ile Tyr Asn Val Leu Pro
385                 390                 395                 400

Thr Thr Ser Leu Val Leu Gly Lys Asn Gln Thr Leu Ala Thr Ile Lys
                405                 410                 415

Ala Lys Glu Asn Gln Leu Ser Gln Ile Leu Ala Pro Asn Asn Tyr Tyr
            420                 425                 430

Pro Ser Lys Asn Leu Ala Pro Ile Ala Leu Asn Ala Gln Asp Asp Phe
        435                 440                 445
```

```
Ser Ser Thr Pro Ile Thr Met Asn Tyr Asn Gln Phe Leu Glu Leu Glu
    450                 455                 460

Lys Thr Lys Gln Leu Arg Leu Asp Thr Asp Gln Val Tyr Gly Asn Ile
465                 470                 475                 480

Ala Thr Tyr Asn Phe Glu Asn Gly Arg Val Arg Val Asp Thr Gly Ser
                485                 490                 495

Asn Trp Ser Glu Val Leu Pro Gln Ile Gln Glu Thr Thr Ala Arg Ile
            500                 505                 510

Ile Phe Asn Gly Lys Asp Leu Asn Leu Val Glu Arg Arg Ile Ala Ala
        515                 520                 525

Val Asn Pro Ser Asp Pro Leu Glu Thr Thr Lys Pro Asp Met Thr Leu
    530                 535                 540

Lys Glu Ala Leu Lys Ile Ala Phe Gly Phe Asn Glu Pro Asn Gly Asn
545                 550                 555                 560

Leu Gln Tyr Gln Gly Lys Asp Ile Thr Glu Phe Asp Phe Asn Phe Asp
                565                 570                 575

Gln Gln Thr Ser Gln Asn Ile Lys Asn Gln Leu Ala Glu Leu Asn Val
            580                 585                 590

Thr Asn Ile Tyr Thr Val Leu Asp Lys Ile Lys Leu Asn Ala Lys Met
        595                 600                 605

Asn Ile Leu Ile Arg Asp Lys Arg Phe His Tyr Asp Arg Asn Asn Ile
    610                 615                 620

Ala Val Gly Ala Asp Glu Ser Val Val Lys Glu Ala His Arg Glu Val
625                 630                 635                 640

Ile Asn Ser Ser Thr Glu Gly Leu Leu Leu Asn Ile Asp Lys Asp Ile
                645                 650                 655

Arg Lys Ile Leu Ser Gly Tyr Ile Val Glu Ile Glu Asp Thr Glu Gly
            660                 665                 670

Leu Lys Glu Val Ile Asn Asp Arg Tyr Asp Met Leu Asn Ile Ser Ser
        675                 680                 685

Leu Arg Gln Asp Gly Lys Thr Phe Ile Asp Phe Lys Lys Tyr Asn Asp
    690                 695                 700

Lys Leu Pro Leu Tyr Ile Ser Asn Pro Asn Tyr Lys Val Asn Val Tyr
705                 710                 715                 720

Ala Val Thr Lys Glu Asn Thr Ile Ile Asn Pro Ser Glu Asn Gly Asp
                725                 730                 735

Thr Ser Thr Asn Gly Ile Lys Lys Ile Leu Ile Phe Ser Lys Lys Gly
            740                 745                 750

Tyr Glu Ile Gly Gly Pro Gly Pro Lys Asn Leu Asp Cys Trp Val Asp
        755                 760                 765

Asn Glu Glu Asp Ile Asp Val Ile Leu Lys Lys Ser Thr Ile Leu Asn
    770                 775                 780

Leu Asp Ile Asn Asn Asp Ile Ile Ser Asp Ile Ser Gly Phe Asn Ser
785                 790                 795                 800

Ser Val Ile Thr Tyr Pro Asp Ala Gln Leu Val Pro Gly Ile Asn Gly
                805                 810                 815

Lys Ala Ile His Leu Val Asn Asn Glu Ser Ser Glu Val Ile Val His
            820                 825                 830

Lys Ala Met Asp Ile Glu Tyr Asn Asp Met Phe Asn Asn Phe Thr Val
        835                 840                 845

Ser Phe Trp Leu Arg Val Pro Lys Val Ser Ala Ser His Leu Glu Gln
    850                 855                 860
```

```
Tyr Gly Thr Asn Glu Tyr Ser Ile Ile Ser Ser Met Lys Lys His Ser
865                 870                 875                 880

Leu Ser Ile Gly Ser Gly Trp Ser Val Ser Leu Lys Gly Asn Asn Leu
                885                 890                 895

Ile Trp Thr Leu Lys Asp Ser Ala Gly Glu Val Arg Gln Ile Thr Phe
            900                 905                 910

Arg Asp Leu Pro Asp Lys Phe Asn Ala Tyr Leu Ala Asn Lys Trp Val
        915                 920                 925

Phe Ile Thr Ile Thr Asn Asp Arg Leu Ser Ser Ala Asn Leu Tyr Ile
    930                 935                 940

Asn Gly Val Leu Met Gly Ser Ala Glu Ile Thr Gly Leu Gly Ala Ile
945                 950                 955                 960

Arg Glu Asp Asn Asn Ile Thr Leu Lys Leu Asp Arg Cys Asn Asn Asn
                965                 970                 975

Asn Gln Tyr Val Ser Ile Asp Lys Phe Arg Ile Phe Cys Lys Ala Leu
            980                 985                 990

Asn Pro Lys Glu Ile Glu Lys Leu  Tyr Thr Ser Tyr Leu  Ser Ile Thr
        995                 1000                1005

Phe Leu  Arg Asp Phe Trp Gly  Asn Pro Leu Arg Tyr  Asp Thr Glu
    1010                1015                1020

Tyr Tyr  Leu Ile Pro Val Ala  Ser Ser Ser Lys Asp  Val Gln Leu
    1025                1030                1035

Lys Asn  Ile Thr Asp Tyr Met  Tyr Leu Thr Asn Ala  Pro Ser Tyr
    1040                1045                1050

Thr Asn  Gly Lys Leu Asn Ile  Tyr Tyr Arg Arg Leu  Tyr Asn Gly
    1055                1060                1065

Leu Lys  Phe Ile Ile Lys Arg  Tyr Thr Pro Asn Asn  Glu Ile Asp
    1070                1075                1080

Ser Phe  Val Lys Ser Gly Asp  Phe Ile Lys Leu Tyr  Val Ser Tyr
    1085                1090                1095

Asn Asn  Asn Glu His Ile Val  Gly Tyr Pro Lys Asp  Gly Asn Ala
    1100                1105                1110

Phe Asn  Asn Leu Asp Arg Ile  Leu Arg Val Gly Tyr  Asn Ala Pro
    1115                1120                1125

Gly Ile  Pro Leu Tyr Lys Lys  Met Glu Ala Val Lys  Leu Arg Asp
    1130                1135                1140

Leu Lys  Thr Tyr Ser Val Gln  Leu Lys Leu Tyr Asp  Asp Lys Asn
    1145                1150                1155

Ala Ser  Leu Gly Leu Val Gly  Thr His Asn Gly Gln  Ile Gly Asn
    1160                1165                1170

Asp Pro  Asn Arg Asp Ile Leu  Ile Ala Ser Asn Trp  Tyr Phe Asn
    1175                1180                1185

His Leu  Lys Asp Lys Ile Leu  Gly Cys Asp Trp Tyr  Phe Val Pro
    1190                1195                1200

Thr Asp  Glu Gly Trp Thr Asn  Asp Lys Leu
    1205                1210
```

<210> SEQ ID NO 9
<211> LENGTH: 786
<212> TYPE: DNA
<213> ORGANISM: Artificial sequence
<220> FEATURE:
<223> OTHER INFORMATION: DNA sequence encoding hCD40L

<400> SEQUENCE: 9

```
atgatcgaaa catacaacca aacttctccc cgatctgcgg ccactggact gcccatcagc     60

atgaaaattt tcatgtattt acttactgtc tttcttatca cccagatgat tgggtcagca    120

ctttttgctg tgtatcttca tagaaggttg gacaagatag aagatgaaag gaatcttcat    180

gaagattttg tattcatgaa aacgatacag agatgcaaca caggagaaag atccttatcc    240

ttactgaact gtgaggagat taaaagccag tttgaaggct ttgtgaagga tataatgtta    300

aacaaagagg agacgaagaa agaaaacagc tttgaaatgc aaaaaggtga tcagaatcct    360

caaattgcgg cacatgtcat aagtgaggcc agcagtaaaa caacatctgt gttacagtgg    420

gctgaaaaag gatactacac catgagcaac aacttggtaa ccctggaaaa tgggaaacag    480

ctgaccgtta aaagacaagg actctattat atctatgccc aagtcacctt ctgttccaat    540

cgggaagctt cgagtcaagc tccatttata gccagcctct gcctaaagtc tcccggtaga    600

ttcgagagaa tcttactcag agctgcaaat acccacagtt ccgccaaacc ttgcgggcaa    660

caatccattc acttgggagg agtatttgaa ttgcaaccag gtgcttcggt gtttgtcaat    720

gtgactgatc caagccaagt gagccatggc actggcttca cgtcctttgg cttactcaaa    780

ctctga                                                                786


<210> SEQ ID NO 10
<211> LENGTH: 261
<212> TYPE: PRT
<213> ORGANISM: Homo sapiens

<400> SEQUENCE: 10

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
```

```
225                 230                 235                 240

Val Thr Asp Pro Ser Gln Val Ser His Gly Thr Gly Phe Thr Ser Phe
                245                 250                 255

Gly Leu Leu Lys Leu
            260


<210> SEQ ID NO 11
<211> LENGTH: 726
<212> TYPE: DNA
<213> ORGANISM: Artificial sequence
<220> FEATURE:
<223> OTHER INFORMATION: DNA sequence encoding hIL15R-Sushi

<400> SEQUENCE: 11

atggccccca gacgggccag aggctgtaga accctgggac tgcctgccct gctgctgctc      60

ctcctgctga ggcctcctgc cacccggggc atcacctgtc ccccacccat gagcgtggaa     120

cacgccgaca tctgggtcaa gagctacagc ctgtacagca gagagcggta catctgcaac     180

agcggcttca agcggaaggc cggcaccagc agcctgaccg agtgcgtgct gaacaaggcc     240

accaacgtgg cccactggac cacccccagc ctgaagtgca tcagggaccc cgccctggtg     300

catcagaggc ctgctcctcc aagcggcgga tctggcggcg gaggaagtgg cggaggatca     360

ggcggaggcg gcagcctgca gaactgggtc aacgtgatca gcgacctgaa gaagatcgag     420

gacctgatcc agagcatgca catcgacgcc accctgtaca ccgagagcga cgtgcacccc     480

agctgcaaag tgaccgccat gaagtgcttt ctgctggaac tgcaggtcat cagcctggaa     540

agcggcgacg ccagcatcca cgacaccgtg gaaaacctga tcatcctggc caacaacagc     600

ctgagcagca acggcaacgt gaccgagagc ggctgcaaag agtgcgagga actggaagag     660

aagaatatca aagagttcct gcagagcttc gtgcacatcg tgcagatgtt catcaacacc     720

agctga                                                                726


<210> SEQ ID NO 12
<211> LENGTH: 241
<212> TYPE: PRT
<213> ORGANISM: Homo sapiens

<400> SEQUENCE: 12

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Gly Gly Ser Gly
            100                 105                 110

Gly Gly Gly Ser Gly Gly Gly Ser Gly Gly Gly Gly Ser Leu Gln Asn
        115                 120                 125

Trp Val Asn Val Ile Ser Asp Leu Lys Lys Ile Glu Asp Leu Ile Gln
    130                 135                 140
```

```
Ser Met His Ile Asp Ala Thr Leu Tyr Thr Glu Ser Asp Val His Pro
145                 150                 155                 160

Ser Cys Lys Val Thr Ala Met Lys Cys Phe Leu Leu Glu Leu Gln Val
                165                 170                 175

Ile Ser Leu Glu Ser Gly Asp Ala Ser Ile His Asp Thr Val Glu Asn
            180                 185                 190

Leu Ile Ile Leu Ala Asn Asn Ser Leu Ser Ser Asn Gly Asn Val Thr
        195                 200                 205

Glu Ser Gly Cys Lys Glu Cys Glu Glu Leu Glu Glu Lys Asn Ile Lys
    210                 215                 220

Glu Phe Leu Gln Ser Phe Val His Ile Val Gln Met Phe Ile Asn Thr
225                 230                 235                 240

Ser


<210> SEQ ID NO 13
<211> LENGTH: 753
<212> TYPE: DNA
<213> ORGANISM: Homo sapiens

<400> SEQUENCE: 13

atggttgctg ggagcgacgc ggggcgggcc ctgggggtcc tcagcgtggt ctgcctgctg     60

cactgctttg gtttcatcag ctgtttttcc caacaaatat atggtgttgt gtatgggaat    120

gtaactttcc atgtaccaag caatgtgcct ttaaaagagg tcctatggaa aaaacaaaag    180

gataaagttg cagaactgga aaattctgaa ttcagagctt tctcatcttt taaaaatagg    240

gtttatttag acactgtgtc aggtagcctc actatctaca acttaacatc atcagatgaa    300

gatgagtatg aaatggaatc gccaaatatt actgatacca tgaagttctt tctttatgtg    360

cttgagtctc ttccatctcc cacactaact tgtgcattga ctaatggaag cattgaagtc    420

caatgcatga taccagagca ttacaacagc catcgaggac ttataatgta ctcatgggat    480

tgtcctatgg agcaatgtaa acgtaactca accagtatat attttaagat ggaaaatgat    540

cttccacaaa aaatacagtg tactcttagc aatccattat ttaatacaac atcatcaatc    600

attttgacaa cctgtatccc aagcagcggt cattcaagac acagatatgc acttataccc    660

ataccattag cagtaattac aacatgtatt gtgctgtata tgaatggtat tctgaaatgt    720

gacagaaaac cagacagaac caactccaat tga                                 753


<210> SEQ ID NO 14
<211> LENGTH: 250
<212> TYPE: PRT
<213> ORGANISM: Homo sapiens

<400> SEQUENCE: 14

Met Val Ala Gly Ser Asp Ala Gly Arg Ala Leu Gly Val Leu Ser Val
1               5                   10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
        35                  40                  45

Val Pro Leu Lys Glu Val Leu Trp Lys Lys Gln Lys Asp Lys Val Ala
    50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95
```

```
Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
    130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
    210                 215                 220

Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250
```

```
<210> SEQ ID NO 15
<211> LENGTH: 1599
<212> TYPE: DNA
<213> ORGANISM: Homo sapiens

<400> SEQUENCE: 15

atggctccca gcagcccccg gcccgcgctg cccgcactcc tggtcctgct cggggctctg     60

ttcccaggac ctggcaatgc ccagacatct gtgtccccct caaaagtcat cctgccccgg    120

ggaggctccg tgctggtgac atgcagcacc tcctgtgacc agcccaagtt gttgggcata    180

gagaccccgt tgcctaaaaa ggagttgctc ctgcctggga acaaccggaa ggtgtatgaa    240

ctgagcaatg tgcaagaaga tagccaacca atgtgctatt caaactgccc tgatgggcag    300

tcaacagcta aaaccttcct caccgtgtac tggactccag aacgggtgga actggcaccc    360

ctcccctctt ggcagccagt gggcaagaac cttaccctac gctgccaggt ggagggtggg    420

gcaccccggg ccaacctcac cgtggtgctg ctccgtgggg agaaggagct gaaacgggag    480

ccagctgtgg gggagcccgc tgaggtcacg accacggtgc tggtgaggag agatcaccat    540

ggagccaatt tctcgtgccg cactgaactg gacctgcggc cccaagggct ggagctgttt    600

gagaacacct cggcccccta ccagctccag acctttgtcc tgccagcgac tcccccacaa    660

cttgtcagcc cccgggtcct agaggtggac acgcagggga ccgtggtctg ttccctggac    720

gggctgttcc cagtctcgga ggcccaggtc cacctggcac tgggggacca gaggttgaac    780

cccacagtca cctatggcaa cgactccttc tcggccaagg cctcagtcag tgtgaccgca    840

gaggacgagg gcacccagcg gctgacgtgt gcagtaatac tggggaacca gagccaggag    900

acactgcaga cagtgaccat ctacagcttt ccggcgccca acgtgattct gacgaagcca    960

gaggtctcag aagggaccga ggtgacagtg aagtgtgagg cccaccctag agccaaggtg   1020

acgctgaatg gggttccagc ccagccactg ggcccgaggg cccagctcct gctgaaggcc   1080

accccagagg acaacgggcg cagcttctcc tgctctgcaa ccctggaggt ggccggccag   1140

cttatacaca agaaccagac ccgggagctt cgtgtcctgt atggcccccg actggacgag   1200
```

```
agggattgtc cgggaaactg gacgtggcca gaaaattccc agcagactcc aatgtgccag   1260

gcttggggga acccattgcc cgagctcaag tgtctaaagg atggcacttt cccactgccc   1320

atcggggaat cagtgactgt cactcgagat cttgagggca cctacctctg tcgggccagg   1380

agcactcaag gggaggtcac ccgcaaggtg accgtgaatg tgctctcccc ccggtatgag   1440

attgtcatca tcactgtggt agcagccgca gtcataatgg gcactgcagg cctcagcacg   1500

tacctctata accgccagcg gaagatcaag aaatacagac tacaacaggc ccaaaaaggg   1560

acccccatga aaccgaacac acaagccacg cctccctag                          1599
```

<210> SEQ ID NO 16
<211> LENGTH: 532
<212> TYPE: PRT
<213> ORGANISM: Homo sapiens

<400> SEQUENCE: 16

```
Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300
```

```
Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
    530
```

```
<210> SEQ ID NO 17
<211> LENGTH: 867
<212> TYPE: DNA
<213> ORGANISM: Homo sapiens

<400> SEQUENCE: 17

atgggccaca cacggaggca gggaacatca ccatccaagt gtccatacct caatttcttt     60

cagctcttgg tgctggctgg tctttctcac ttctgttcag gtgttatcca cgtgaccaag    120

gaagtgaaag aagtggcaac gctgtcctgt ggtcacaatg tttctgttga agagctggca    180

caaactcgca tctactggca aaaggagaag aaaatggtgc tgactatgat gtctggggac    240

atgaatatat ggcccgagta caagaaccgg accatctttg atatcactaa taacctctcc    300

attgtgatcc tggctctgcg cccatctgac gagggcacat acgagtgtgt tgttctgaag    360

tatgaaaaag acgctttcaa gcgggaacac ctggctgaag tgacgttatc agtcaaagct    420

gacttcccta cacctagtat atctgacttt gaaattccaa cttctaatat tagaaggata    480

atttgctcaa cctctggagg ttttccagag cctcacctct cctggttgga aaatggagaa    540

gaattaaatg ccatcaacac aacagtttcc caagatcctg aaactgagct ctatgctgtt    600

agcagcaaac tggatttcaa tatgacaacc aaccacagct tcatgtgtct catcaagtat    660

ggacatttaa gagtgaatca gaccttcaac tggaatacaa ccaagcaaga gcattttcct    720

gataacctgc tcccatcctg ggccattacc ttaatctcag taaatggaat tttgtgata    780
```

```
tgctgcctga cctactgctt tgccccaaga tgcagagaga gaaggaggaa tgagagattg     840

agaagggaaa gtgtacgccc tgtataa                                         867


<210> SEQ ID NO 18
<211> LENGTH: 288
<212> TYPE: PRT
<213> ORGANISM: Homo sapiens

<400> SEQUENCE: 18

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285


<210> SEQ ID NO 19
<211> LENGTH: 2031
<212> TYPE: DNA
<213> ORGANISM: Artificial sequence
<220> FEATURE:
<223> OTHER INFORMATION: codon-optimized DNA encoding GP-ZEBOV-Mayinga
      (GenBank Accession No. ABX75367.1)

<400> SEQUENCE: 19

atgggcgtga caggcattct gcagctcccc agagacagat tcaagcggac ctcctttttc      60
```

```
ctctgggtca tcattctgtt tcagcggacc ttctccatcc ctctgggcgt gatccacaat    120

agcaccctcc aggtgtccga cgtggacaag ctcgtgtgcc gggacaagct gtcctccacc    180

aaccagctga gaagcgtggg gctgaatctc gagggcaatg gcgtggccac agacgtgccc    240

tccgccacaa agcgctgggg ctttcggagc ggcgtccctc ctaaagtcgt gaactacgag    300

gcaggggaat gggctgaaaa ttgttacaat ctcgagatca aaaaaccaga tggctctgag    360

tgcctgcctg ccgcaccaga cggcatcagg ggcttcccta gatgccgcta tgtgcacaag    420

gtgagtggta caggcccttg tgccggcgat tttgcctttc acaaagaggg ggctttcttt    480

ctgtacgaca ggctcgccag tacagtgata taccgaggta ctaccttcgc cgaaggcgtg    540

gtggcctttc tgattctgcc ccaggccaag aaggacttct tcagcagcca cccccctgaga    600

gaacccgtga acgccacaga ggaccccagc agcggctact acagcaccac aatcagatac    660

caggccacag gcttcggcac caatgagaca gagtacctgt tcgaggtgga caacctgacc    720

tacgtgcagc tggaaagccg gtttacccct cagttcctcc tgcagctcaa cgagacaatc    780

tacacctccg gcaagcggag caacacaaca ggcaagctca tctggaaagt gaaccccgag    840

atcgatacca ctatagggga gtgggctttc tgggaaacta agaagaacct cacccggaag    900

atcagatccg aggaactgtc cttcaccgtg gtgtccaacg gcgccaagaa catttcagga    960

cagagccccg ccagaacaag cagcgacccc ggcaccaaca ccacaaccga ggaccacaag   1020

atcatggcca gcgagaactc cagcgccatg gtgcaggtcc acagccaggg aagagaagcc   1080

gccgtgagcc acctgaccac actggccacc atcagcacca gcccccagag cctgaccacc   1140

aagcctggcc ccgacaacag cacacacaac acccccgtgt acaagctgga catcagcgag   1200

gccacccagg tggagcagca ccacagacgg accgacaacg acagcaccgc cagcgatacc   1260

ccttctgcca ccacagccgc cggacccccct aaggccgaga ataccaacac cagcaagagc   1320

accgactttc tggatccagc caccaccacc agtccacaga accacagcga aaccgccggc   1380

aacaacaata cccaccacca ggacaccggc gaggaaagcg ccagctctgg caagctgggc   1440

ctgattacca acacaatcgc cggcgtggcc ggactgatca ccggcggcag acggaccaga   1500

cgggaggcca tcgtgaacgc ccagcccaaa tgtaatccta atctccacta ttggaccaca   1560

caggacgagg gcgctgccat cggactggca tggattcctt acttcggacc agccgctgaa   1620

gggatctata tcgaggggct catgcataac caggatggtc tgatttgtgg tctccggcag   1680

ctggctaatg agacaacaca ggctctccag ctgtttctga gagccacaac agagctgaga   1740

accttcagca ttctcaaccg caaggctatt gacttcctgc tccaacgatg gggaggcaca   1800

tgccacatcc tggggcctga ttgttgtatc gaacctcacg attggacaaa gaacattaca   1860

gataagatcg atcagattat ccatgacttt gtggacaaga ccctgcccga tcagggcgac   1920

aacgataatt ggtggacagg gtggagacag tggattccag ccgggattgg cgtgaccggc   1980

gtgattatcg ccgtgatcgc cctgttctgc atctgcaagt tcgtgttctg a             2031
```

<210> SEQ ID NO 20
<211> LENGTH: 676
<212> TYPE: PRT
<213> ORGANISM: ZEBOV-Mayinga

<400> SEQUENCE: 20

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30
```

```
Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445
```

```
Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675


<210> SEQ ID NO 21
<211> LENGTH: 159
<212> TYPE: DNA
<213> ORGANISM: Artificial sequence
<220> FEATURE:
<223> OTHER INFORMATION: DNA sequence encoding VV B5R anchor

<400> SEQUENCE: 21

cctaagcctt ctacacctcc tggcagcagc gccacctacc acatcatcat cgtggccctg      60

acaattatgg gcgtgatctt cctgatcagc gtgatcgtgc tcgtgtgcag ctgcgacaag     120

aacaacgacc agtacaagtt ccacaagctg ctgccctga                            159


<210> SEQ ID NO 22
<211> LENGTH: 42
<212> TYPE: PRT
<213> ORGANISM: Vaccinia Virus

<400> SEQUENCE: 22

Ala Thr Tyr His Ile Ile Ile Val Ala Leu Thr Ile Met Gly Val Ile
1               5                   10                  15

Phe Leu Ile Ser Val Ile Val Leu Val Cys Ser Cys Asp Lys Asn Asn
            20                  25                  30

Asp Gln Tyr Lys Phe His Lys Leu Leu Pro
        35                  40
```

<210> SEQ ID NO 23
<211> LENGTH: 40
<212> TYPE: DNA
<213> ORGANISM: Artificial sequence
<220> FEATURE:
<223> OTHER INFORMATION: promoter sequence

<400> SEQUENCE: 23
aaaaattgaa attttatttt ttttttttgg aatataaata 40

<210> SEQ ID NO 24
<211> LENGTH: 234
<212> TYPE: DNA
<213> ORGANISM: Artificial sequence
<220> FEATURE:
<223> OTHER INFORMATION: promoter sequence

<400> SEQUENCE: 24
aaaaattgaa attttatttt ttttttttgg aatataaata aaaaattgaa aaactattct 60
aatttattgc acggtccggt aaaaattgaa aaactattct aatttattgc acggtccggt 120
aaaaattgaa aaactattct aatttattgc acggtccggt aaaaattgaa aaactattct 180
aatttattgc acggtccggt aaaaattgaa aaactattct aatttattgc acgg 234

<210> SEQ ID NO 25
<211> LENGTH: 104
<212> TYPE: DNA
<213> ORGANISM: Artificial sequence
<220> FEATURE:
<223> OTHER INFORMATION: promoter sequence

<400> SEQUENCE: 25
tccaaaccca cccgcttttt atagtaagtt tttcacccat aaataataaa tacaataatt 60
aatttctcgt aaaagtagaa aatatattct aatttattgc acgg 104

<210> SEQ ID NO 26
<211> LENGTH: 119
<212> TYPE: DNA
<213> ORGANISM: Fowlpox virus

<400> SEQUENCE: 26
ttaatgtata gaactaattt ataataaaca tagtaaatat gggtaacttc ttaatagcca 60
taattaaaat tgaaaaaaaa atatcattat aaaacgtaaa cgaacaaaaa acattaatt 119

<210> SEQ ID NO 27
<211> LENGTH: 227
<212> TYPE: DNA
<213> ORGANISM: Artificial sequence
<220> FEATURE:
<223> OTHER INFORMATION: promoter sequence

<400> SEQUENCE: 27
gttttgaaaa ttttttttata ataaatatcc ggtaaaaatt gaaaaactat tctaatttat 60
tgcacggtcc ggtaaaaatt gaaaaactat tctaatttat tgcacggtcc ggtaaaaatt 120
gaaaaactat tctaatttat tgcacggtcc ggtaaaaatt gaaaaactat tctaatttat 180
tgcacggtcc ggtaaaaatt gaaaaactat tctaatttat tgcacgg 227

<210> SEQ ID NO 28
<211> LENGTH: 2220
<212> TYPE: DNA
<213> ORGANISM: Artificial sequence
<220> FEATURE:

<223> OTHER INFORMATION: codon-optimized DNA sequence encoding NP-EBOV-
      CdI (GenBank Accession No. ACI28629.1)

<400> SEQUENCE: 28

```
atggaaagca gggcccacaa ggcctggatg acacacaccg ccagcggctt cgagacagac     60

taccacaaga tcctgacagc cggcctgtct gtgcagcagg gcatcgtgcg gcagcgcgtg    120

atccaggtgc accaggtgac caacctggaa gagatctgcc agctgatcat ccaggccttc    180

gaggccggcg tggacttcca ggaaagcgcc gacagcttcc tgctgatgct gtgcctgcac    240

cacgcctacc agggcgacta caagcagttc ctggaaagca acgccgtgaa gtacctggaa    300

gggcacggct tcagattcga agtgcggaag aaagaaggcg tgaagcggct ggaagaactg    360

ctgcctgccg ccagctccgg caagagcatc agacgcaccc tggccgccat gcccgaggaa    420

gagacaaccg aggccaacgc tggccagttc ctgagcttcg ccagcctgtt cctgcctaag    480

ctggtggtgg gcgagaaggc ctgcctggaa aaggtgcagc ggcagattca ggtgcacagc    540

gagcagggcc tgatccagta ccctaccgcc tggcagagcg tgggccacat gatggtgatc    600

ttccggctga tgcggaccaa cttcctgatc aagtttctgc tgatccacca gggaatgcac    660

atggtggctg gccacgacgc caatgacgcc gtgatcgcca atagcgtggc ccaggccaga    720

ttcagcggcc tgctgatcgt gaaaacagtg ctggaccaca tcctgcagaa aaccgagcac    780

ggcgtgagac tgcaccctct ggcccggacc gccaaagtga agaacgaagt gaacagcttc    840

aaggccgccc tgtctagcct ggcccagcac ggcgagtacg cccctttcgc ccggctgctg    900

aacctgagcg gcgtgaacaa tctggaacac ggactgttcc cccagctgag cgccattgcc    960

ctgggagtgg ccacagccca cggctctaca ctggccggcg tgaacgtggg cgagcagtac   1020

cagcagctga gagaggccgc cacagaggcc gagaagcagc tgcagaagta cgccgagagc   1080

cgggagctgg atcacctggg cctggacgac caggaaaaga agatcctgaa ggacttccac   1140

cagaagaaga acgagatcag cttccagcag accaccgcca tggtgaccct gcggaaagag   1200

cggctggcca agctgaccga ggccatcacc tccaccagcc tgctgaaaac cggcaagcag   1260

tacgacgacg acaatgacat ccccttccct ggccccatca acgacaacga gaactccgag   1320

cagcaggacg atgaccccac cgatagccag gataccacca tccccgacat catcgtggac   1380

cccgacgacg gccggtacaa caactacggc gactacccca gcgagacagc caatgccccc   1440

gaggacctgg tgctgttcga cctggaagat ggcgacgagg acgaccacag acccagcagc   1500

tccagcgaga acaacaacaa gcacagcctg accggcaccg acagcaacaa gaccagcaac   1560

tggaaccgga accccaccaa catgcccaag aaggacagca cccagaacaa cgacaacccc   1620

gcccagagag cccaggaata cgcccgggac aacatccagg acacccctac ccctcacaga   1680

gccctgaccc ccatcagcga ggaaaccggc tccaacggcc acaacgagga cgatatcgac   1740

agcatccccc ccctggaatc cgacgaggaa aacaacaccg aaaccaccat caccaccaca   1800

aagaacacca ccgcccctcc cgcccctgtg taccggtcca acagcgagaa agagcccctg   1860

cctcaggaaa agagccagaa acagcccaat caggtgtccg gcagcgagaa taccgacaac   1920

aagccccaca gcgaacagag cgtggaggaa atgtaccggc acattctgca gacccagggc   1980

cccttcgacg ccatcctgta ctactacatg atgacagagg aacccatcgt gttcagcacc   2040

tccgacggca aagaatacgt gtaccccgac agcctggaag gcgagcaccc tccctggctg   2100

agcgaaaaag aggccctgaa cgaggacaac cggttcatca ccatggacga tcagcagttc   2160

tactggcccg tgatgaacca ccggaacaag ttcatggcca tcctgcagca ccacaagtga   2220
```

<210> SEQ ID NO 29
<211> LENGTH: 739
<212> TYPE: PRT
<213> ORGANISM: EBOV-CdI

<400> SEQUENCE: 29

```
Met Glu Ser Arg Ala His Lys Ala Trp Met Thr His Thr Ala Ser Gly
1               5                   10                  15

Phe Glu Thr Asp Tyr His Lys Ile Leu Thr Ala Gly Leu Ser Val Gln
            20                  25                  30

Gln Gly Ile Val Arg Gln Arg Val Ile Gln Val His Gln Val Thr Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Gln Phe Leu Glu Ser Asn Ala Val
                85                  90                  95

Lys Tyr Leu Glu Gly His Gly Phe Arg Phe Glu Val Arg Lys Lys Glu
            100                 105                 110

Gly Val Lys Arg Leu Glu Glu Leu Leu Pro Ala Ala Ser Ser Gly Lys
        115                 120                 125

Ser Ile Arg Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ser Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu His Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Gln His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Lys Tyr Ala Glu Ser Arg Glu Leu Asp His Leu Gly Leu
        355                 360                 365

Asp Asp Gln Glu Lys Lys Ile Leu Lys Asp Phe His Gln Lys Lys Asn
    370                 375                 380
```

```
Glu Ile Ser Phe Gln Gln Thr Thr Ala Met Val Thr Leu Arg Lys Glu
385                 390                 395                 400

Arg Leu Ala Lys Leu Thr Glu Ala Ile Thr Ser Thr Ser Leu Leu Lys
                405                 410                 415

Thr Gly Lys Gln Tyr Asp Asp Asp Asn Asp Ile Pro Phe Pro Gly Pro
            420                 425                 430

Ile Asn Asp Asn Glu Asn Ser Glu Gln Gln Asp Asp Asp Pro Thr Asp
        435                 440                 445

Ser Gln Asp Thr Thr Ile Pro Asp Ile Ile Val Asp Pro Asp Asp Gly
    450                 455                 460

Arg Tyr Asn Asn Tyr Gly Asp Tyr Pro Ser Glu Thr Ala Asn Ala Pro
465                 470                 475                 480

Glu Asp Leu Val Leu Phe Asp Leu Glu Asp Gly Asp Glu Asp Asp His
                485                 490                 495

Arg Pro Ser Ser Ser Ser Glu Asn Asn Asn Lys His Ser Leu Thr Gly
            500                 505                 510

Thr Asp Ser Asn Lys Thr Ser Asn Trp Asn Arg Asn Pro Thr Asn Met
        515                 520                 525

Pro Lys Lys Asp Ser Thr Gln Asn Asn Asp Asn Pro Ala Gln Arg Ala
    530                 535                 540

Gln Glu Tyr Ala Arg Asp Asn Ile Gln Asp Thr Pro Thr Pro His Arg
545                 550                 555                 560

Ala Leu Thr Pro Ile Ser Glu Glu Thr Gly Ser Asn Gly His Asn Glu
                565                 570                 575

Asp Asp Ile Asp Ser Ile Pro Pro Leu Glu Ser Asp Glu Glu Asn Asn
            580                 585                 590

Thr Glu Thr Thr Ile Thr Thr Thr Lys Asn Thr Thr Ala Pro Pro Ala
        595                 600                 605

Pro Val Tyr Arg Ser Asn Ser Glu Lys Glu Pro Leu Pro Gln Glu Lys
    610                 615                 620

Ser Gln Lys Gln Pro Asn Gln Val Ser Gly Ser Glu Asn Thr Asp Asn
625                 630                 635                 640

Lys Pro His Ser Glu Gln Ser Val Glu Glu Met Tyr Arg His Ile Leu
                645                 650                 655

Gln Thr Gln Gly Pro Phe Asp Ala Ile Leu Tyr Tyr Tyr Met Met Thr
            660                 665                 670

Glu Glu Pro Ile Val Phe Ser Thr Ser Asp Gly Lys Glu Tyr Val Tyr
        675                 680                 685

Pro Asp Ser Leu Glu Gly Glu His Pro Pro Trp Leu Ser Glu Lys Glu
    690                 695                 700

Ala Leu Asn Glu Asp Asn Arg Phe Ile Thr Met Asp Asp Gln Gln Phe
705                 710                 715                 720

Tyr Trp Pro Val Met Asn His Arg Asn Lys Phe Met Ala Ile Leu Gln
                725                 730                 735

His His Lys
```

<210> SEQ ID NO 30
<211> LENGTH: 2031
<212> TYPE: DNA
<213> ORGANISM: Artificial sequence
<220> FEATURE:
<223> OTHER INFORMATION: Codon optimized DNA sequence encoding GP-SEBOV-Gulu (GenBank Accession No. AAU43887.1)

<400> SEQUENCE: 30

```
atgggcggcc tgagcctgct gcagctgccc cgggacaagt tccggaagtc cagcttcttc     60
gtgtgggtga tcatcctgtt ccagaaagcc ttcagcatgc cctgggcgt ggtgaccaac     120
agcaccctgg aagtgaccga gatcgaccag ctggtgtgca aggaccacct ggccagcacc    180
gatcagctga agtccgtggg cctgaacctg gaaggcagcg gcgtgagcac cgacatcccc    240
agcgccacca agagatgggg cttcagatcc ggcgtgcccc ccaaggtggt gtcttatgag    300
gccggcgagt gggccgagaa ctgctacaac ctggaaatca agaagcccga cggcagcgag    360
tgtctgcctc cccctcccga tggcgtgaga ggcttccccc ggtgcagata cgtgcacaag    420
gcacaaggca ccggtccatg cccaggcgac tacgccttcc acaaggacgg cgcctttttc    480
ctgtacgacc ggctggcctc caccgtgatc taccggggcg tgaactttgc cgagggcgtg    540
atcgccttcc tgatcctggc caagcccaaa gagacattcc tgcagagccc ccccatccgg    600
gaggccgtga actacaccga gaacaccagc agctactacg ccacctccta cctggaatac    660
gagatcgaga acttcggcgc ccagcacagc accaccctgt tcaagatcga caacaacacc    720
ttcgtgcggc tggacagacc ccacaccccc cagtttctgt tccagctgaa cgacaccatc    780
catctgcatc agcagctgtc caacaccacc ggcagactga tctggaccct ggacgccaac    840
atcaacgccg acatcggtga atgggctttt tgggagaaca agaagaatct gagcgagcag    900
ctgcggggcg aagaactcag cttcgaggcc ctgagcctga acgagacaga ggacgacgac    960
gccgccagca gccggatcac caagggccgg atcagcgacc gggccaccag aaagtacagc   1020
gacctggtgc ccaagaacag ccccggcatg gtgcctctgc acatccccga gggcgagaca   1080
actctcccta gtcagaatag caccgagggc agacgggtgg gcgtgaacac ccaggaaacc   1140
atcaccgaga cagccgccac catcattggt actaacggca accacatgca gatcagcacc   1200
atcggcatcc ggcccagcag cagccagatc ccaagtagta gtcctaccac agcccctagc   1260
cctgaggccc agacccctac cacacacacc agcggcccta gcgtgatggc caccgaggaa   1320
cctaccaccc ctcctggcag cagcccaggt ccaactaccg aggcaccaac cctgaccacc   1380
cccgagaaca tcaccaccgc cgtgaaaacc gtgctgcccc aggaaagcac cagcaacggc   1440
ctgatcacca gcaccgtgac cggcatcctg ggcagcctgg gcctgcggaa gcggagcaga   1500
cggcagacca acaccaaggc caccggcaag tgcaaccccca acctgcacta ctggaccgcc  1560
caggaacagc acaacgccgc tgggatcgcc tggatcccct actttggtcc tggtgctgag   1620
ggaatataca ccgagggcct gatgcacaac cagaacgccc tggtgtgcgg cctgagacag   1680
ctggccaacg aaaccactca ggcactgcag ctgttcctgc gggccaccac cgagctgcgg   1740
acctacacca tcctgaacag gaaggccatc gactttctgc tgcggagatg gggcggcacc   1800
tgtagaatcc tgggccccga ctgctgcatc gagccccacg actggaccaa gaatatcacc   1860
gacaagatca accagatcat ccacgacttc atcgacaacc ccctgcccaa ccaggacaac   1920
gacgacaact ggtggactgg ttggcgacag tggatccctg ccggcatcgg catcaccggc   1980
atcatcattg ccattatcgc tctcctctgc gtgtgcaagc tcctctgctg a            2031
```

<210> SEQ ID NO 31
<211> LENGTH: 676
<212> TYPE: PRT
<213> ORGANISM: SEBOV-Gulu

<400> SEQUENCE: 31

```
Met Gly Gly Leu Ser Leu Leu Gln Leu Pro Arg Asp Lys Phe Arg Lys
1               5                   10                  15
```

```
Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
                245                 250                 255

Asn Asp Thr Ile His Leu His Gln Gln Leu Ser Asn Thr Thr Gly Arg
            260                 265                 270

Leu Ile Trp Thr Leu Asp Ala Asn Ile Asn Ala Asp Ile Gly Glu Trp
        275                 280                 285

Ala Phe Trp Glu Asn Lys Lys Asn Leu Ser Glu Gln Leu Arg Gly Glu
    290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
                325                 330                 335

Arg Lys Tyr Ser Asp Leu Val Pro Lys Asn Ser Pro Gly Met Val Pro
            340                 345                 350

Leu His Ile Pro Glu Gly Glu Thr Thr Leu Pro Ser Gln Asn Ser Thr
        355                 360                 365

Glu Gly Arg Arg Val Gly Val Asn Thr Gln Glu Thr Ile Thr Glu Thr
    370                 375                 380

Ala Ala Thr Ile Ile Gly Thr Asn Gly Asn His Met Gln Ile Ser Thr
385                 390                 395                 400

Ile Gly Ile Arg Pro Ser Ser Ser Gln Ile Pro Ser Ser Ser Pro Thr
                405                 410                 415

Thr Ala Pro Ser Pro Glu Ala Gln Thr Pro Thr Thr His Thr Ser Gly
            420                 425                 430
```

```
Pro Ser Val Met Ala Thr Glu Glu Pro Thr Thr Pro Pro Gly Ser Ser
        435                 440                 445

Pro Gly Pro Thr Thr Glu Ala Pro Thr Leu Thr Thr Pro Glu Asn Ile
    450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Thr Asn Thr Lys Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
    530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
        675
```

<210> SEQ ID NO 32
<211> LENGTH: 187
<212> TYPE: DNA
<213> ORGANISM: Artificial sequence
<220> FEATURE:
<223> OTHER INFORMATION: promoter sequence

<400> SEQUENCE: 32

```
gttttgaaaa ttttttata ataaatatcc ggtaaaaatt gaaaaactat tctaatttat     60

tgcacggtcc ggtaaaaatt gaaaaactat tctaatttat tgcacggtcc ggtaaaaatt    120

gaaaaactat tctaatttat tgcacggtcc ggtaaaaatt gaaaaactat tctaatttat    180

tgcacgg                                                              187
```

<210> SEQ ID NO 33
<211> LENGTH: 984
<212> TYPE: DNA
<213> ORGANISM: Artificial sequence
<220> FEATURE:
<223> OTHER INFORMATION: codon-optimized VP40 sequence

<400> SEQUENCE: 33

```
atgcggcgcg tgatcctgcc caccgcccct ccagagtaca tggaagccat ctaccccgtg     60

cggagcaaca gcacaatcgc cagaggcggc aacagcaata ccggcttcct gacccccgag    120
```

```
agcgtgaacg gcgacacccc cagcaacccc ctgaggccta tcgccgacga caccatcgac    180

cacgccagcc acacccctgg cagcgtgtcc agcgccttca tcctggaagc catggtgaac    240

gtgatcagcg gccccaaggt gctgatgaag cagatcccca tctggctgcc cctgggcgtg    300

gccgaccaga aaacctacag cttcgacagc accaccgccg ccatcatgct ggccagctac    360

accatcaccc acttcggcaa ggccaccaac cccctggtgc gcgtgaacag actgggccct    420

ggcatccccg accacccct gagactgctg cggatcggca accaggcctt cctgcaggaa    480

ttcgtgctgc cccccgtgca gctgccccag tacttcacct tcgacctgac cgccctgaag    540

ctgatcaccc agcctctgcc tgccgccacc tggaccgatg atacccccac aggcagcaac    600

ggcgccctga ggcccggcat cagcttccac cccaagctga ggcccatcct gctgcccaac    660

aagagcggca agaagggcaa cagcgccgac ctgacctccc ccgagaagat ccaggccatc    720

atgaccagcc tgcaggactt caagatcgtg cccatcgacc ccaccaagaa catcatgggc    780

atcgaggtgc ccgagacact ggtgcacaag ctgaccggca agaaagtgac cagcaagaac    840

ggccagccca tcatccctgt gctgctgcct aagtacatcg gcctggaccc cgtggcccct    900

ggcgacctga ccatggtgat cacacaggac tgcgatacct gccacagccc cgccagcctg    960

cccgccgtga ttgagaagta atag                                            984
```

```
<210> SEQ ID NO 34
<211> LENGTH: 326
<212> TYPE: PRT
<213> ORGANISM: ZEBOV-Mayinga

<400> SEQUENCE: 34

Met Arg Arg Val Ile Leu Pro Thr Ala Pro Pro Glu Tyr Met Glu Ala
1               5                   10                  15

Ile Tyr Pro Val Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
        195                 200                 205

Phe His Pro Lys Leu Arg Pro Ile Leu Leu Pro Asn Lys Ser Gly Lys
```

```
    210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
        275                 280                 285

Leu Pro Lys Tyr Ile Gly Leu Asp Pro Val Ala Pro Gly Asp Leu Thr
    290                 295                 300

Met Val Ile Thr Gln Asp Cys Asp Thr Cys His Ser Pro Ala Ser Leu
305                 310                 315                 320

Pro Ala Val Ile Glu Lys
                325
```

<210> SEQ ID NO 35
<211> LENGTH: 124
<212> TYPE: DNA
<213> ORGANISM: Artificial sequence
<220> FEATURE:
<223> OTHER INFORMATION: promoter sequence

<400> SEQUENCE: 35

```
taaaaataga aactataatc atataatagt gtaggttggt agtattgctc ttgtgactag     60

agactttagt taaggtactg taaaaataga aactataatc atataatagt gtaggttggt    120

agta                                                                 124
```

<210> SEQ ID NO 36
<211> LENGTH: 2046
<212> TYPE: DNA
<213> ORGANISM: Artificial sequence
<220> FEATURE:
<223> OTHER INFORMATION: codon-optimzed DNA sequence GP-MARV-Angola

<400> SEQUENCE: 36

```
atgaagacga cctgcctgct gatctcgctg attctgattc agggagtgaa aacccttccc     60

attctcgaga ttgcctctaa tatccagcca caaaatgtcg acagtgtgtg ttccggaacc    120

ctccagaaga cagaggatgt tcacctcatg ggattcactc tgtctggaca gaaagtcgca    180

gactctcctc tcgaggctag caaaagatgg gctttccggg caggtgtccc accaaaaaac    240

gtcgagtata ctgaaggcga agaagctaag acttgttata acatttccgt caccgatccc    300

agtggaaaat ccctccttct ggatccacca actaacatta gggattaccc gaaatgtaag    360

acaattcatc acattcaagg acagaaccct catgcccaag ggattgccct ccatctctgg    420

ggtgcattct ttctgtacga caggatcgca tctacaacaa tgtatagagg caaagtcttc    480

acggaaggga acatagctgc tatgatagtt aacaaaaacag ttcacaaaat gattttcagt    540

cggcaagggc agggataccg ccatatgaat ttgacctcga ctaacaaata ctggacatcc    600

tcgaacggaa cccaaacaaa cgatactggc tgtttcggga cactccagga gtacaactct    660

acaaagaacc aaacgtgcgc tccctctaag aagccactgc ctcttcccac cgcccaccct    720

gaagtgaagc tcacatctac cagcacagat gccactaagc tcaacacgac agaccctaat    780

tctgatgacg aggatctcac cacatccggc tccgggagcg gcgagcaaga accctacacc    840

acatctgacg cagccacaaa gcaagggctg tccagcacta tgccacctac tcctagccca    900
```

caacccagta cacctcaaca gggagggaac aatacaaatc attctcaggg cgtggtcaca 960
gagcccggca agaccaacac aactgctcag ccttctatgc ctcctcacaa taccacaacg 1020
atttcgacga ataacacgag caaacacaat ctgagcacac ccagcgtgcc catccagaac 1080
gccacaaatt acaatacaca gtctacagct ccagagaatg aacagacatc cgctcccagc 1140
aagaccacgc tgctgcctac cgagaatcca acaaccgcta aatccaccaa tagcaccaag 1200
tctcccacca ccaccgtgcc taacaccaca aacaagtaca gcacctctcc cagccctaca 1260
cctaactcca ccgctcagca tctcgtgtat tttcgccgca agagaaacat cctctggaga 1320
gagggagata tgtttccatt tctcgacggg ctcattaatg cgcctatcga ttttgatccg 1380
gttccgaaca caaagacgat ctttgatgag tctagctcta gcggagcctc agcagaggaa 1440
gaccaacatg ctagtcctaa tatttccctc accctgtcct atttccctaa agtgaatgaa 1500
aataccgctc actctggaga aaacgaaaat gactgtgacg ctgaactccg gatttggtcc 1560
gttcaggagg atgatctcgc cgcaggactc tcttggattc ccttctttgg accagggatc 1620
gaaggactgt atacagctgg actcatcaaa aatcagaaca atctcgtgtg tcggctcagg 1680
cggctcgcta accaaactgc caaaagcctt gagctccttc tgcgggtcac cacagaggaa 1740
agaacatttt ctctgattaa tcgccacgct atagactttc ttctcgctcg gtggggtgga 1800
acctgcaaag tcctcggacc tgattgctgt atcggaattg aagatctgtc gcggaatatc 1860
tccgagcaaa tcgatcagat taagaaagat gagcaaaagg aaggtacagg gtggggattg 1920
ggtggaaaat ggtggacttc cgattggggt gtcctcacta atctcgggat cctcctcctg 1980
ctctccattg ccgtcctgat cgctctgtca tgtatttgca gaatctttac aaagtatatt 2040
gggtga 2046

<210> SEQ ID NO 37
<211> LENGTH: 681
<212> TYPE: PRT
<213> ORGANISM: MARV-Angola

<400> SEQUENCE: 37

Met Lys Thr Thr Cys Leu Leu Ile Ser Leu Ile Leu Ile Gln Gly Val
1 5 10 15

Lys Thr Leu Pro Ile Leu Glu Ile Ala Ser Asn Ile Gln Pro Gln Asn
20 25 30

Val Asp Ser Val Cys Ser Gly Thr Leu Gln Lys Thr Glu Asp Val His
35 40 45

Leu Met Gly Phe Thr Leu Ser Gly Gln Lys Val Ala Asp Ser Pro Leu
50 55 60

Glu Ala Ser Lys Arg Trp Ala Phe Arg Ala Gly Val Pro Pro Lys Asn
65 70 75 80

Val Glu Tyr Thr Glu Gly Glu Glu Ala Lys Thr Cys Tyr Asn Ile Ser
85 90 95

Val Thr Asp Pro Ser Gly Lys Ser Leu Leu Leu Asp Pro Pro Thr Asn
100 105 110

Ile Arg Asp Tyr Pro Lys Cys Lys Thr Ile His His Ile Gln Gly Gln
115 120 125

Asn Pro His Ala Gln Gly Ile Ala Leu His Leu Trp Gly Ala Phe Phe
130 135 140

Leu Tyr Asp Arg Ile Ala Ser Thr Thr Met Tyr Arg Gly Lys Val Phe
145 150 155 160

Thr Glu Gly Asn Ile Ala Ala Met Ile Val Asn Lys Thr Val His Lys

```
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Thr Leu Gln Glu Tyr Asn Ser Thr Lys Asn Gln
    210                 215                 220

Thr Cys Ala Pro Ser Lys Lys Pro Leu Pro Leu Pro Thr Ala His Pro
225                 230                 235                 240

Glu Val Lys Leu Thr Ser Thr Ser Thr Asp Ala Thr Lys Leu Asn Thr
                245                 250                 255

Thr Asp Pro Asn Ser Asp Asp Glu Asp Leu Thr Thr Ser Gly Ser Gly
            260                 265                 270

Ser Gly Glu Gln Glu Pro Tyr Thr Thr Ser Asp Ala Ala Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Gly Val Val Thr
305                 310                 315                 320

Glu Pro Gly Lys Thr Asn Thr Thr Ala Gln Pro Ser Met Pro Pro His
                325                 330                 335

Asn Thr Thr Thr Ile Ser Thr Asn Asn Thr Ser Lys His Asn Leu Ser
            340                 345                 350

Thr Pro Ser Val Pro Ile Gln Asn Ala Thr Asn Tyr Asn Thr Gln Ser
        355                 360                 365

Thr Ala Pro Glu Asn Glu Gln Thr Ser Ala Pro Ser Lys Thr Thr Leu
    370                 375                 380

Leu Pro Thr Glu Asn Pro Thr Thr Ala Lys Ser Thr Asn Ser Thr Lys
385                 390                 395                 400

Ser Pro Thr Thr Thr Val Pro Asn Thr Thr Asn Lys Tyr Ser Thr Ser
                405                 410                 415

Pro Ser Pro Thr Pro Asn Ser Thr Ala Gln His Leu Val Tyr Phe Arg
            420                 425                 430

Arg Lys Arg Asn Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Lys Val Asn Glu Asn Thr Ala His Ser Gly Glu Asn Glu Asn Asp Cys
            500                 505                 510

Asp Ala Glu Leu Arg Ile Trp Ser Val Gln Glu Asp Asp Leu Ala Ala
        515                 520                 525

Gly Leu Ser Trp Ile Pro Phe Phe Gly Pro Gly Ile Glu Gly Leu Tyr
    530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
            580                 585                 590
```

-continued

```
Phe Leu Leu Ala Arg Trp Gly Gly Thr Cys Lys Val Leu Gly Pro Asp
        595                 600                 605

Cys Cys Ile Gly Ile Glu Asp Leu Ser Arg Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680
```